United States Patent [19]

Högberg et al.

[11] 3,963,707

[45] June 15, 1976

[54] NOVEL N-NITROSO COMPOUNDS, COMPOSITIONS CONTAINING SUCH COMPOUNDS, PROCESSES FOR THEIR PREPARATION AND METHODS OF TREATMENT THEREWITH, AND NOVEL INTERMEDIATES

[75] Inventors: Knut Bertil Högberg; Hans Jacob Fex, both of Helsingborg; Imre Konyves, Hittarp; Anders Robert Stamvik, Helsingborg, all of Sweden

[73] Assignee: Aktiebolaget Leo, Helsingborg, Sweden

[22] Filed: Feb. 25, 1974

[21] Appl. No.: 445,572

[30] Foreign Application Priority Data

Mar. 5, 1973 United Kingdom............... 10613/73

[52] U.S. Cl.................... 260/239.55 D; 260/397.2; 260/397.4; 260/397.45; 260/397.47; 260/397.5; 424/243
[51] Int. Cl.$^2$........................................... C07J 1/00
[58] Field of Search ...................................
/Machine Searched Steroids

*Primary Examiner*—Elbert L. Roberts
*Attorney, Agent, or Firm*—Gordon W. Hueschen

[57] ABSTRACT

This invention relates to novel N-halogenoalkyl-N-nitroso carbamates and N$^4$halogenalkyl-N$^4$-nitroso allophanates of steroid compounds, having an anti-tumor activity, and to the preparation thereof. The invention is also concerned with pharmaceutical compositions containing the said compounds, and methods of treatment therewith.

62 Claims, No Drawings

NOVEL N-NITROSO COMPOUNDS, COMPOSITIONS CONTAINING SUCH COMPOUNDS, PROCESSES FOR THEIR PREPARATION AND METHODS OF TREATMENT THEREWITH, AND NOVEL INTERMEDIATES

This invention relates to novel N-halogenoalkyl-N-nitroso carbamates and $N^4$-halogenoalkyl-$N^4$-nitroso allophanates of steroid compounds, having an antitumor activity, and to the preparation thereof. The invention is also concerned with pharmaceutical compositions containing the said compounds, and methods of treatment therewith.

BACKGROUND OF THE INVENTION

Similarities in physiological effects observed with lower aliphatic N-(2-chloroethyl)-N-nitroso carbamates and mustard gas have been the background for investigations of such carbamates as antitumor agents. The results reported are summarized in Table 1 and show that the compounds investigated are highly toxic and have no activities against any of the tumors against which they have been examined.

Table 1

Toxicity and lack of antitumor activity reported for N-chloroethyl-N-nitroso carbamates.

$$ClCH_2CH_2N(NO)-COOR$$

| R | LD50 mg/kg[a] |
|---|---|
| $C_2H_5-$ | 2[b] |
| $(CH_3)_2CHCH_2-$ | 7[c] |
| $CH_3(CH_2)_2CH_2-$ | 11 – 15[d] |
| Phenyl | 3 – 7[d] |
| β-Naphthyl | 42[d] |

[a]Acute intraperitoneal toxicity in mice.
[b]Reported by K. A. Hyde et al. in J. Med. and Pharm. Chem. 5 (1962) 1. This compound was found to be inactive against the tumors investigated: lymphoid leukemia (L 1210), Sarcoma 180 and Adenocarcinoma 755.
[c]Reported by W. C. J. Ross in J. Med. Chem. 10 (1967) 108. This compound was found to be inactive against the tumors investigated: Walker 256 and lymphoid leukemia (L 1210).
[d]Reported by S. P. Kramer et al. in Cancer 12 (1959) 446.

It has now, surprisingly, been found that N-halogenoalkyl-N-nitroso carbamates of steroid compounds have a low toxicity and also are highly active against animal tumors. It has also been found that $N^4$-halogenoalkyl-$N^4$-nitroso allophanates of steroid compounds have the same valuable properties.

Depending on the nature of steroid, these compounds also show such pharmacological activities which derive from the steroids themselves, e.g., estrogenic, androgenic, anabolic, gestogenic, and corticoid activities. As many steroids are used in connection with treatment of cancer diseases, the steroid part of the molecule can be selected with relation to the kind of tumor which is to be treated.

It is well-known that the effect of steroids can be changed, e.g. prolonged, by esterification and etherification of suitable hydroxy groups in their molecules and also steroids can be made water soluble in the form of salts of acid esters of such hydroxy groups. When the N-halogenoalkyl-N-nitroso carbamates and $N^4$-halogenoalkyl-$N^4$-nitroso allophanates of a steroid according to the invention have one or more remaining free hydroxy groups suitable for esterifications and etherifications, such hydroxy groups can therefore also be present in the compounds of the invention in the form of inorganic or organic esters and organic ethers thereby to confer upon the N-halogenoalkyl-N-nitroso carbamates and $N^4$-halogenoalkyl-$N_4$-nitroso allophanates of such steroids such properties as mentioned above.

SUMMARY OF INVENTION

The new N-halogenoalkyl-N-nitroso carbamates and $N^4$-halogenoalkyl-$N^4$-nitroso allophanates of the present invention correspond to the general formula (I) as defined below.

The compounds of the invention have shown effect in inhibiting the growth of several tumors, e.g., Ehrlich ascites, Hepatoma AH 130, lymphocytic leukemia (L 1210), and Walker carcinoma 256 according to the procedures set by Cancer Chemotherapy National Service Center (see: Cancer Chemotherapy Reports, December 1962 and September 1972).

The compounds of the invention can be employed in disorders responsive to treatment with anticancer agents and with immunosuppressive agents as such or combined with either solid or liquid carriers or diluents and made available in varying amounts in such pharmaceutical forms as, e.g., tablets, pills, capsules, pelletts, powders, ointments, suppositories and aqueous or non-aqueous suspensions and solutions.

Accordingly, one object of the invention is to provide new compounds, having the general formula (I), having the aforesaid activity, preferably also with a relatively low degree of toxicity.

A second object is to provide such type of compounds, which can be employed in disorders responsive to treatment with anticancer agents and with immunosuppressive agents for the amelioration or palliation thereof.

Another object of the invention is to provide processes for preparing the new compounds having the general formula (I).

A further object is to provide novel intermediates having the general formula (III) as defined below.

Still another object of the invention is to provide novel intermediates having the general formula (II) as defined below and wherein m is one, from which the new compounds, having the general formula (I) with m equal to one, can be prepared, as well as processes for the preparation of said intermediates. Further additional compounds within the scope of the general formula (II) are novel and are so useful.

A further object of the invention is to provide a method of treating a living animal body suffering from disorders responsive to treatment with "anticancer agents" and with immunosuppressive agents, which comprises the step of administering to said living animal body an effective amount of a compound having the general formula (I), said compound being administered in an amount sufficient to at least militate said disorders.

Yet another object of the invention is to provide compositions containing as an active ingredient one or more of the compounds, having the general formula (I), preferably together with a pharmaceutically acceptable carrier and, if desired, other pharmacologically active agents.

According to the invention there are provided novel compounds having the general formula:

$$AR_n \quad (I)$$

or functional derivatives thereof,
wherein
R is $$-O-(C-N)_m - C - N - NO$$
$$\phantom{-O-(}\| \phantom{C-N)_m-}\| \phantom{C-}|$$
$$\phantom{-O-(C-N)_m-C-}R^2 \phantom{-C-}R^1$$

where
  $R^1$ is a $\beta$- or $\gamma$-halogen substituted alkyl group having 2 to 4 carbon atoms, inclusive, the halogen or $R^1$ being fluorine, chlorine or bromine,
where
  m is an integer selected from the group consisting of zero and one;
where
  $R^2$, when m is one, is selected from the group consisting of $R^1$, hydrogen, lower alkyl, 5- or 6-membered cycloalkyl, substituted 5- or 6-membered cycloalkyl, phenyl and substituted phenyl, any such ring substitution being at most a disubstitution based on substituents selected from the group consisting of halogen, for instance fluorine or chlorine, lower alkyl and lower alkoxy,
wherein
  n is one or two; and
wherein
  A is a residue of a steroid selected from the group consisting of estrogens, androgens, gestogens, corticoids and sterols, and where any hydroxy group when present in the steroid molecule is either free; esterified with an acid selected from the group consisting of aliphatic mono- and di-carboxylic acids, alicyclic acids, arylaliphatic acids, aromatic mono- and di-carboxylic acids, mono lower alkyl and mono phenyl phosphoric acids and inorganic polybasic acids; or esterified with an alcohol selected from the group consisting of aliphatic and alicyclic alcohols. When esterified with a polybasic acid resulting in one or more acid esters such acid esters may be in the form of free acids or salts thereof. Any esterifying or etherifying group preferably contains a maximum of 15 carbon atoms, any etherifying group especially a maximum of 6 carbon atoms.

Thus A can be the radical of a steroid having a cyclopentanophenanthrene carbon-carbon skeleton containing up to a maximum of 40 carbon atoms, inclusive of substituents, said carbon-carbon skeleton including a nucleus selected from the group consisting of saturated and unsaturated gonane nuclei having up to a maximum of four (4) double bonds, said steroid radical being attached to R in at least one and not more than two of the 3-, 11-, 16-, 17- and 21-positions thereof, said positions being identified according to steroid nomenclature.

Said radical of a steroid as defined above has a carbon-carbon skeleton preferably selected from the group consisting of: estra-1,3,5(10)-triene, estra-1,3,5(10), 16-tetraene, androstane, androst-4-ene, androst-5-ene, estr-4-ene, estr-5(10)-ene, pregn-4-ene, pregna-4,6-diene, pregn-5-ene, pregna-1,4-diene, cholestan, cholest-5-ene, cholesta-5,22-diene and cholesta-5,7,22-triene carbon-carbon skeletons.

The foregoing mentioned carbon-carbon skeletons are respectively related to biological activity as follows:
  Estrogens; estra-1,3,5(10)-triene and estra-1,3,5(10),16-tetraene.
  Androgens: androstane, androst-4-ene, androst-5-ene and estr-4-ene.
  Gestogens: estr-4-ene, estr-5(10)-ene, pregn-4-ene and pregna-4,6-diene.
  Corticoids: pregn-4-ene, pregn-5-ene and pregna-1,4-diene.
  Sterols: cholestane, cholest-5-ene, cholesta-5,22-diene and cholesta-5,7,22-dien.

Preferred nuclei for these types of steroids are as follows:
  Estrogens: estra-1,3,5(10),16-tetraen-3-ol, estra-1,3,5(10)-trien-3-ol-17-one, estra-1,3,5(10)-triene-3,16-diol-17-ones, estra-1,3,5(10)-triene-3,17-diol-16-ones, estra-1,3,5(10)-triene-3,16,17-triols and estra-1,3,5(10)-triene-3,17-diols.
  Androgens: androstan-3-ol-17-ones, androstan-17-ol-3-ones, androstane-3,17-diols, androstane-3,16-diol-17-ones, androst-4-en-3-ol-17-ones, androst-4-en-17-ol-3-ones, androst-4-ene-3,17-diols, androst-4-ene-11,17-diol-3-ones, androst-5-en-3-ol-17-ones, androst-5-en-17-ol-3-ones, androst-5-ene-3,17-diols, estr-4-en-17-ols and estr-4-en-17-ol-3-ones.
  Gestogens: estr-4-en-17-ols, estr-4-en-17-ol-3-ones, estr-4-ene-3,17-diols, estr-5(10)-en-17-ol-3-ones, androst-4-en-17-ol-3-ones, pregn-4-ene-17-ol-3-ones, pregn-4-ene-17-ol-3,20-diones, pregna-4,6-dien-17-ol-3,20-diones and pregna-4,6-dien-3,17-diol-20-ones.
  Corticoids: pregn-5-en-3-ol-20-ones, pregn-4-en-21-ol-3,20-diones, pregn-4-ene-11,21-diol-3,20-diones, pregn-4-en-21-ol-3,11,20-triones, pregn-4-ene-17,21-diol-3,11,20-triones, pregn-4-ene-11,17,21-triol-3,20-diones, pregn-4-ene-11,16,17,21-tetraol-3,20-diones, pregna-1,4-diene-17,21-diol-3,11,20-triones, pregna-1,4-diene-11,17,21-triol-3,20-diones and pregna-1,4-diene-11,16,17,21-tetraol-3,20-diones.
  Sterols: cholestan-3-ols, cholst-5-en-3-ols, cholesta-5,22-dien-3-ols and cholesta-5,7,22-trien-3-ols.

When said nuclei defined above have hydroxy groups present in both the 16- and 17-positions these hydroxy groups may be in the form of an 16,17-acetonide.

Said steroid radical A has the said steroid nucleus with a hydroxy group removed from at least one and not more than two of the said 3-, 11-, 16-, 17- and 21-positions thereof; the said radical R being attached to said steroid nucleus in at least one and not more than two of said positions.

Preferably any further substitution as is present in the carbon-carbon skeletons of said steroid nucleus being at most a tetra-substitution wherein the positions of the teroid carbon-carbon skeleton which are substituted are selected from the positions consisting of the 2-, 4-, 6-, 7-, 9-, 16-, 17-, 18- and 24-positions; and where the substitution, if any, comprises at least one substituent preferably selected from the group consisting of methyl, ethyl, methylene, ethynyl, allyl, fluoro and chloro.

When said steroid nucleus has such further substitution it is preferred:
  that the estrogens, as defined above, have an ethynyl group in the 17 -position;

that the androgens, as defined above, have substituents selected from a methyl group in one or two of the 2-, 4-, 6-, 7- and 17-positions, an ethyl group in the 17-position and a fluoro group in the 9-position;

that the gestogens as defined above, have substituents selected from a methyl group in one or both of the 6- and 18-positions, an ethynyl or an allyl group in the 17-position and a chloro group in the 6-position;

that the corticoids, as defined above, have substituents selected from a methyl group in one or both of the 6- and 16-positions, a methylene group in the 16-position and a fluoro group in one or both of the 6- and 9-positions;

that the sterols, as defined above, have a methyl or an ethyl group in the 24-position.

In this disclosure the steroids are numbered in accordance with the I.U.P.A.C. 1957 Rules of Nomenclature of Steroids.

In the general formula $AR_n$ above it is preferred that $n$ is equal to one. If $n$ is two, preferred steroids are estrogens and androgens.

With regard to $R^1$, it is preferred that the halogen of $R^1$ is positioned in the $\beta$-position.

The halogen of $R^1$ is preferably chlorine or fluorine, and of these especially chlorine.

The alkyl group of $R^1$ is preferably ethyl, n-propyl or n-butyl, and of these especially ethyl.

Compounds, wherein $R^1$ is Cl—CH$_2$—CH$_2$—, are particularly preferred.

When $R^2$ is substituted cyclopentyl or cyclohexyl or phenyl, it is preferred that the substitution is a monosubstitution, preferably in the 3- or 4-position, with a halogen, for instance fluorine or chlorine, a lower alkyl group or a lower alkoxy group.

Compounds, wherein $R^2$ is $R^1$, lower alkyl, cyclohexyl or substituted cyclohexyl are preferred, and particularly preferred compounds are those wherein $R^2$ is cyclohexyl or 4- lower alkyl -cyclohexyl.

Preferred steroid hormones from which A can derive are the following:

Estrogens, when the living animal body suffers from cancer diseases known to be responsive to treatment with estrogen hormones, preferably estra-1,3,5(10),16-tetraene-3-ol, and
substituted estra-1,3,5(10)-triens such as:
estra-1,3,5(10)-trien-3-ol-17-one (estrone)
estra-1,3,5(10)-triene-3,17$\beta$-diol (estradiol-17$\beta$)
estra-1,3,5(10)-triene-3,17$\alpha$-diol (estradiol-17$\alpha$)
estra-1,3,5(10)-triene-3,16$\alpha$,17$\beta$-triol (estriol)
estra-1,3,5(10)-triene-3,16$\beta$,17$\beta$-triol (16-epiestriol)
estra-1,3,5(10)-triene-3,16$\alpha$,17$\alpha$-triol (17-epiestriol)
estra-1,3,5(10)-triene-3,16$\alpha$-diol-17-one
estra-1,3,5(10)-triene-3,17$\beta$-diol-16-one
17$\alpha$-ethynyl-estra-1,3,5(10)-triene-3,17$\beta$-diol (17$\alpha$-ethynyl-estradiol)

Among the estrogens mentioned above the following are particularly preferred:
estrone, estradiol-17$\beta$, estriol and 17$\alpha$-ethynyl-estradiol.

Androgens, when the living animal body suffers from cancer diseases known to be responsive to treatment with androgen hormones, preferably
substituted androstanes such as:
androstan-3$\alpha$-ol-17-one (androsterone)

androstan-3$\beta$-ol-17-one (epiandrosterone)
androstan-3$\beta$,16$\alpha$-diol-17-one (16$\alpha$-hydroxyepiandrosterone)
androstan-17$\alpha$-ol-3-one (epidihydrotestosterone)
androstan-17$\beta$-ol-3-one (dihydrotestosterone)
2$\alpha$-methylandrostan-17$\beta$-ol-3-one (2$\alpha$-methyl-dihydrotestosterone)
4$\alpha$-methylandrostan-17$\beta$-ol-3-one (4$\alpha$-methyl-dihydrotestosterone)
6$\alpha$-methylandrostan-17$\beta$-ol-3-one (6$\alpha$-methyl-dihydrotestosterone)
6$\beta$-methylandrostan-17$\beta$-ol-3-one (6$\beta$-methyl-dihydrotestosterone)
17$\alpha$-methylandrostan-17$\beta$-ol-3-one (17$\alpha$-methyl-dihydrotestosterone)
androstane-3$\alpha$,17$\alpha$-diol
androstane-3$\alpha$,17$\beta$-diol (androstanediol)
androstane-3$\beta$,17$\beta$-diol
17$\alpha$-methylandrostane-3$\alpha$,17$\beta$-diol
17$\alpha$-methylandrostane-3$\beta$,17$\beta$-diol
etiocholan-3$\alpha$-ol-17-one (etiocholanolone)
etiocholan-3$\beta$-ol-17-one, and
substituted androst-4-enes such as:
androst-4-en-3$\beta$-ol-17-one
androst-4-en-17$\beta$-ol-3-one (testosterone)
androst-4-ene-3$\beta$,17$\beta$-diol
4-methylandrost-4-en-17$\beta$-ol-3-one (4-methyltestosterone)
6$\alpha$-methylandrost-4-en-17$\beta$-ol-3-one (6$\alpha$-methyltestosterone)
17$\alpha$-methylandrost-4-en-17$\beta$-ol-3-one (17$\alpha$-methyltestosterone)
17$\alpha$-ethylandrost-4-en-17$\beta$-ol-3-one (17$\alpha$-ethyltestosterone)
17$\alpha$-methylandrost-4-ene-9$\alpha$-fluoro-11$\beta$,17$\beta$-diol-3-one (9$\alpha$-fluoro-11$\beta$-hydroxy-17$\alpha$-methyltestosterone)
7$\alpha$,17$\alpha$-dimethylandrost-4-en-17$\beta$-ol-3-one (7$\alpha$,17$\alpha$-dimethyltestosterone), and
substituted androst-5-enes such as:
androst-5-en-3$\alpha$-ol-17-one
androst-5-en-3$\beta$-ol-17-one (dehydroepiandrosterone)
androst-5-en-17$\beta$-ol-3-one
androst-5-ene-3$\alpha$,17$\beta$-diol
androst-5-ene-3$\beta$,17$\beta$-diol (androstenediol)
17$\alpha$-methylandrost-5-ene-3$\beta$,17$\beta$-diol (17$\alpha$-methylandrostenediol), and
substituted estr-4-enes such as:
estr-4-en-17$\beta$-ol-3-one (19-nortestosterone)
17$\alpha$-ethyl-estr-4-en-17$\beta$-ol-3-one (17$\alpha$-ethyl-19-nortestosterone)
17$\alpha$-ethyl-estr-4-en-17$\beta$-ol Among the androgens mentioned above the following are particularly preferred:
androsterone, epiandrosterone, dihydrotestosterone, androstanediol, testosterone, 17$\alpha$-methyltestosterone, 9$\alpha$-fluoro-11$\beta$-hydroxy-17$\alpha$-methyltestosterone, dehydroepiandrosterone, androstenediol, 19-nortestosterone, and etiocholanolone.

Most particularly preferred androgens are the following: androsterone, epiandrosterone, dihydrotestosterone, androstanediol, testosterone, dehydroepiandrosterone, and androstenediol.

Gestogens, when the living animal body suffers from cancer diseases known to be responsive to treatment with gestogen hormones, preferably
substituted estr-4-enes such as:

17α-ethynyl-estr-4-en-17β-ol
17α-allyl-estr-4-en-17β-ol
17α-ethynyl-estr-4-ene-3β,17β-diol (ethynodiol)
17α-ethynyl-estr-4-en-17β-ol-3-one (17α-ethynyl-19-nortestosterone)
17α-allyl-estr-4-en-17β-ol-3-one (17α-allyl-19-nortestosterone)
17α-ethynyl-18-methyl-estr-4-en-17β-ol-3-one (17α-ethynyl-18-methyl-19-nortestosterone), and
substituted estr-5(10)-enes such as:
17α-ethynyl-estr-5(10)-en-17β-ol-3-one (norethynodrel), and substituted androst-4-ens such as:
17α-ethynyl-androst-4-en-17β-ol-3-one (17α-ethynyltestosterone)
substituted pregn-4-ens such as:
pregn-4-en-17α-ol-3,20-dione (17α-hydroxyprogesterone)
6α-methyl-pregn-4-en-17α-ol-3,20-dione (-6α-methyl-17α-hydroxy-progesterone), and
substituted pregna-4,6-diens such as:
6-methyl-pregna-4,6-dien-17α-ol-3,20-dione (6-methyl-6-dehydro-17α-hydroxyprogesterone)
6-chloro-pregna-4,6-dien-17α-ol-3,20-dione (6-chloro-6-dehydro-17α-hydroxyprogesterone)
6-chloro-pregna-4,6-diene-3β,17α-diol-20-one.

Among the gestagens mentioned above, the following are particularly preferred:
ethynodiol, 17α-ethynyl-19-nortestosteron, norethynodrel, 17α-hydroxyprogesterone and 6-chloro-pregna-4,6-dien-3β,17α-diol-20-one Corticoids, when the living animal body suffers from cancer or autoimmune diseases known to be responsive to treatment with corticoid hormones, preferably
pregn-5-en-3β-ol-2-one (pregnenolone)
substituted pregn-4-ens such as:
pregn-4-en-21-ol-3,20-dione (deoxycorticosterone)
pregn-4-ene-11β,21-diol-3,20-dione (corticosterone)
pregn-4-en-21-ol-3,11,20-trione (11-dehydrocorticosterone)
pregn-4-ene-17α,21-diol-3,11,20-trione (cortisone)
pregn-4-ene-11β,17α,21-triol-3,20-dione (hydrocortisone)
9α-fluoro-pregn-4-ene-11β,17α,21-triol-3,20-dion (9α-fluorohydrocortisone)
6α-fluoro-16α,17α-isopropylidendioxy-pregn-4-ene-11β,21-diol-3,20-dione (6α-fluoro-16α-hydroxyhydrocortisone-16,17-acetonide), and
substituted pregn-1,4-diens such as:
pregna-1,4-diene-17α,21-diol-3,11,20-trione (prednisone)
pregna-1,4-diene-11β,17α,21-triol-3,20-dione (prednisolone)
6α-methyl-pregna-1,4-diene-11β,17α,21-triol-3,20-dione (6α-methyl-prednisolone)
16-methylene-pregna-1,4-diene-11β,17α,21-triol-3,20-dione (16-methylenprednisolone)
6α-fluoro-16α-methyl-pregna-1,4-diene-11β,17α,21-triol-3,20-dione (6α-fluoro-16α-methylprednisolone)
6α-fluoro-16α,17α-isopropylidendioxypregna-1,4-diene-11β,21-diol-3,20-dione (6α-fluoro-16α-hydroxyprednisolone-16,17-acetonide)
9α-fluoro-16α-methyl-pregna-1,4-diene-11β,17α,21-triol-3,20-dione (9α-fluoro-16α-methyl-prednisolone)
9α-fluoro-16β-methyl-pregna-1,4-diene-11β,17α,21-triol-3,20-dione (9α-fluoro-16β-methylprednisolone)
9α-fluoro-pregna-1,4-diene-11β,16α,17α,21-tetrol-3,20-dione (9α-fluoro-16α-hydroxyprednisolone)
9α-fluoro-16α,17α-isopropylidendioxypregna-1,4-diene-11β,21-diol-3,20-dione (9α-fluoro-16α-hydroxyprednisolone-16,17-acetonide)
6α,9α-difluoro-16α-methyl-pregna-1,4-diene-11β,17α,21-triol-3,20-dione (6α,9α-difluoro-16α-methylprednisolone)
6α,9α-difluoro-pregn-1,4-diene-11β,16α,17α,21-tetrol-3,20-dione (6α,9α-difluoro-16α-hydroxy-prednisolone)
6α,9α-difluoro-16α,17α-isopropylidendioxypregna-1,4-diene-11β,21-diol-3,20-dione (6α,9α-difluoro-16α-hydroxyprednisolone-16,17-acetonide)
6α-fluoro-16α-methylen-pregna-1,4-diene-11β,17α,21-triol-3,20-dione.

Among the corticoids mentioned above the following are particularly preferred:
pregnenolon, deoxycorticosterone, hydrocortisone, prednisolone, 9α-fluoro-16α-methylprednisolone, 9α-fluoro-16β-methyl-prednisolone, 9α-fluoro-16α-hydroxy-prednisolone and 9α-fluoro-16α-hydroxyprednisolone-16,17-acetonide.

Most particularly preferred corticoids are the following: pregnenolone, deoxycorticosterone and prednisolone.

Sterols, when no hormonal effect is desired, preferably
5β-cholestan-3β-ol (coprosterol)
5α-cholestan-3β-ol (cholestanol)
cholest-5-en-3β-ol (cholesterol)
24α-ethylcholesta-5,22-dien-3β-ol (stigmasterol)
24β-methylcholesta-5,7,22-trien-3β-ol (ergosterol)

Among the sterols mentioned above cholesterol is particularly preferred.

Compounds of formula (I), wherein m is zero, are preferred for some purposes, whereas compounds, wherein m is one, are preferred for other purposes, but both are characterized by the stated properties, activity and utility.

The points of attachment between one or two R and one or two carbon atoms of the steroid skeleton of A, respectively, are preferably selected from:
the 3-, 16- and 17-positions when A is an estrogen residue;
the 3- and 17-positions when A is an androgen or a gestogen residue;
the 3-, 11- and 21-positions when A is a corticoid residue;
the 3-position when A is a sterol residue.

Among acids which can be used to form esters with one or more remaining hydroxy groups connected to carbon atoms of the steroid skeleton of A, as mentioned above, the following are preferred:

Alkane monocarboxylic acids of straight or branched nature having at most ten carbon atoms, such as acetic acid, propionic acid, valeric acid, pivalic acid, caprionic acid, oenanthic acid, and capric acid.

Alkane dicarboxylic acids having at most four carbon atoms, such as oxalic acid, malonic acid, and succinic acid.

Alicyclic carboxylic acids having six or seven carbon atoms, such as cyclopentyl carboxylic acid and cyclohexyl carboxylic acid.

Aromatic benzene-mono- or di-carboxylic acids such as benzoic acid, phthalic acid, isophthalic acid and terephthalic acid.

Arylaliphatic acids having at most fifteen carbon atoms, such as phenylacetic acid, phenylpropionic acid, p-propoxyphenylpropionic acid and p-hexoxyphenylpropionic acid.

Mono lower alkyl and mono phenyl phosphoric acids.

Inorganic polybasic acids such as phosphoric acid and sulfuric acid.

Especially preferred lower alkane monocarboxylic acids are acetic acid and propionic acid.

To obtain lipophilic esters the following acids are especially preferred:

valeric acid, capronic acid, oenanthic acid, capric acid, p-propoxy-phenylpropionic acid, p-hexoxy-phenylpropionic acid and benzoic acid.

To obtain hydrophilic esters having acid ester groups the following acids are especially preferred:

succinic acid, phosphoric acid, lower alkyl phosphoric acid and phenyl phosphoric acid.

Among alcohols which can be used to form ethers with one or more remaining hydroxy groups connected to carbon atoms of the steroid skeleton of A, the following are preferred:

Aliphatic alcohols containing at most three carbon atoms, such as methanol and ethanol.

Alicyclic alcohols containing five or six carbon atoms, such as cyclopentanol and cyclohexanol.

Particularly preferred alcohols among those given above are methanol and cyclopentanol.

When A above contains esterified hydroxy groups, such groups are preferably positioned in one or two of the 3-, 16-, 17- and 21-positions.

When A above contains etherified hydroxy groups, such ethers are preferably positioned in the 3- or 17-position.

When A above contains one or more hydroxy groups esterified with a polybasic acid any remaining acid group or groups are preferably in the form of pharmaceutically acceptable salts with suitable inorganic or organic cations, such as those derived from the following metals and amines:

metals: calcium, potassium and sodium amines: monoethanolamine, diethanolamine, dimethylaminoethanol, N-methylglucamine, trishydroxymethylmethylamine, morpholine and the like.

In this disclosure the expression lower means that the group referred to contains one to four carbon atoms, inclusive. Thus, lower alkyl and lower alkoxy include: methyl, ethyl, propyl, iso-propyl, butyl, secondary butyl, iso-butyl, tertiary butyl, methoxy, ethoxy, propoxy, isopropoxy, butoxy, isobutoxy, secondary butoxy, and tertiary butoxy.

With regard to R in the general formula (I) above, the compounds wherein $m$ is zero are preferred in those cases where the compounds are intended to be used in aqueous solutions and good water solubility is desirable.

The compounds named in the examples given in the following, and being within the scope of formula (I), are of particular interest for our intended purposes.

Preferred starting materials for the preparation of compounds having the general formula (I) above are novel compounds having the general formula:

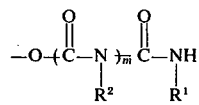 (II)

or functional derivatives thereof; wherein $R^3$ is

wherein A, $m$, $n$, $R^1$ and $R^2$ have the meaning given above, and wherein said steroid radical A is attached to $R^3$ at at least one and not more than two of the 3-, 11-, 16-, 17- and 21-positions thereof when $m$ is one, and at at least one and not more than two of the 3-, 11-, 16- and 17-positions thereof when $m$ is zero.

Other novel compounds useful for the preparation of compounds having the general formula (I) above are compounds having the general formula

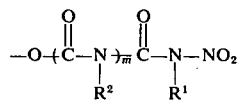 (III)

or functional derivatives thereof; wherein $R^4$ is $$-O-(\overset{O}{\overset{\|}{C}}-\underset{R^2}{N})_{\overline{m}}\overset{O}{\overset{\|}{C}}-\underset{R^1}{N}-NO_2$$

wherein A, $m$, $n$, $R^1$ and $R^2$ have the meaning given above, and wherein said steroid radical A is attached to $R^4$ at at least one and not more than two of the 3-, 11-, 16-, 17- and 21-positions thereof.

In the said general formulas (II) and (III) as defined above, the said steroid radical A has the said steroid nucleus with a hydroxy group removed from at least one and not more than two of said positions thereof; the said radicals $R^3$ and $R^4$ respectively being attached to said steroid nucleus in at least one and not more than two of said positions.

METHODS OF PREPARATION

The compounds having the above formula (I) may be prepared by methods known per se, see for instance Sandler, Karo-Organic Functional Group Preparations, Vol. 2, Chapter 17, N-Nitroso compounds.

A general process (method 1 below) for preparing the compounds having the general formula (I) above is as follows:

Method 1

A compound having the general formula (II) above is transferred to a compound having the general formula (I) by N-nitrosation.

N-nitrosation can be performed according to known methods, for instance those described in the reference given above. Among methods described the following may be mentioned:

(a) nitrosation in aqueous media with a metal nitrite such as an alkali metal nitrite, and a suitable acid,
(b) nitrosation in an organic solvent with a metal nitrite such as an alkali metal nitrite and a suitable acid,
(c) nitrosation with dinitrogen trioxide ($N_2O_3$),
(d) nitrosation with nitrosyl chloride (NOCl),
(e) nitrosation with dinitrogen tetroxide ($N_2O_4$),
(f) nitrosation with nitrosyl sulfuric acid,
(g) nitrosation with an alkyl nitrite,
(h) nitrosation with nitrosonium tetrafluoroborate.

Nitrosations under c-h are preferably performed under anhydrous conditions.

Of other methods for preparing a compound having the general formula (I) above, the following may be mentioned:

Method 2

A compound having the general formula (II) above is transferred to a compound having the general formula (I) in two steps comprising of N-nitration, e.g. with nitric acid, suitably in the presence of acetic anhydride (for instance according to Curry, Mason - J.Am.- Chem.Sec. 73 (1951), 5043) followed by reduction of the obtained nitro-compound (III) e.g. by a dissolving metal reduction, such as with zink and acetic acid. (for instance acccording to Sabetta - J.Am.Chem. Sec. 57 (1935), 2478).

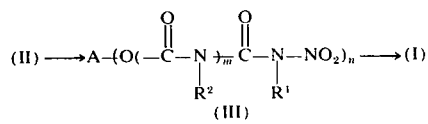

$A$, $n$, $m$, $R^1$ and $R^2$ have the meaning given in the general formula (I) above.

Compounds of the general formula (II) above, which are useful as starting material in the preparation of compounds having the general formula (I) above, may be prepared by methods known per se. Among methods described the following may be mentioned.

Method 3

A compound having the general formula (II) above is obtained by reaction of a steroid of the general formula $A\text{-}(OH)_n$ with a suitably substituted allophanoyl halide or a suitably substituted carbamoyl halide (see for instance Ulrich - J.Org. Chem. 32 (1967):12, 3938).

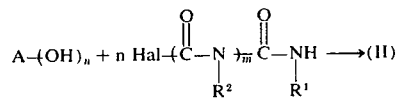

$A$, $n$, $m$, $R^1$ and $R^2$ have the meaning given in formula (I) above, and Hal means a halogen selected from chlorine and bromine.

Substituted allophanoyl chlorides are obtained for instance according to Ulrich - J.Org.Chem. 29 (1964):8, 2401 from a suitably substituted urea and phosgene, and substituted carbamoyl chlorides are obtained for instance according to Tomelia - J.Heterocycl.Chem. 4 (1967):2, 178 from a suitably substituted aziridine and phosgene.

Method 4

Preparation of a steroid haloformyl derivative of the general formula $A\text{-}(O\text{---}CO\text{---}Hal)_n$ is performed according to methods known per se, for instance by reaction of a steroid of the general formula $A\text{-}(OH)_n$ with phosgene or its halogene analogues according to Mischer - Helv.Chim.Acta 20 (1937), 1237 or Rips - Chim.Ther. 5 (1970), 418.

A compound having the general formula II above is prepared by reaction of the steroid haloformyl derivative above with a suitably substituted urea or a suitably substituted amine (see for instance Gleim - J.Am.- Chem.Soc. 76 (1954), 107 and Wertheim - J.Am.- Chem.Soc. 53 (1931), 200).

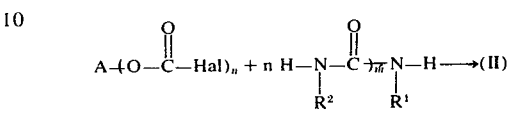

$A$, $n$, $R^1$ and $R^2$ have the meaning given in the general formula (I) above, $m$ is zero or one and Hal means a halogen selected from chlorine and bromine.

Method 5

A steroid carbamate having the formula $A\text{-}(O\text{---}CO\text{---}NH\text{---}R^2)_n$, for instance prepared according to a suitable method given above or below, is converted to a compound of the general formula (II) above, wherein $m$ is one, by reaction with a suitably substituted carbamoyl halide (see for instance Piskala - Collection Czech.Chem.Comm. 26 (1961), 2519).

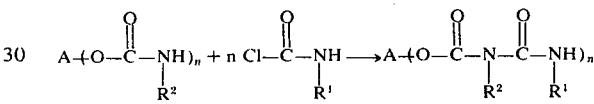

$A$, $n$, $R^1$ and $R^2$ have the meaning given in the general formula (I) above.

Method 6

A steroid carbamate having the general formula $A\text{-}(O\text{---}CO\text{---}NH\text{---}R^2)_n$, for instance prepared according to a suitable method given above or below, is reacted with phosgene to a N-chloroformyl derivative of a steroid carbamate.

Reaction of the N-chloroformyl derivative above with a suitably substituted amine gives a compound of the general formula (II), wherein $m$ is one, (see for instance Gleim - J.Am. Chem. Soc. 76 (1954), 107).

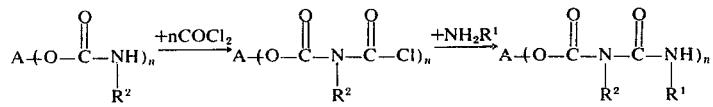

$A$, $n$, $R^1$ and $R^2$ have the meaning given in the general formula (I) above.

Method 7

A compound of the general formula (II) above, wherein $m$ is one, is prepared by reaction of a steroid carbamate $A\text{-}(O\text{---}CO\text{---}NH\text{---}R^2)_n$, for instance obtained by a suitable method given above or below, and a suitably substituted isocyanate (see for instance Cooley - J.Med.Chem. 8 (1965):6, 887).

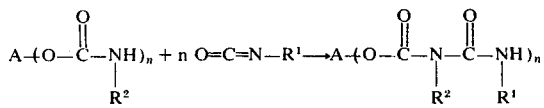

A, $n$, $R^1$ and $R^2$ have the meaning given in the general formula (I) above.

A suitably substituted isocyanate is obtained by methods known per se, see for instance Saunders - Chem.Rev. 43 (1948), 203, Arnold - Chem.Rev. 57 (1957), 47 and Ulrich - Angew.Chem. Int.Ed.Engl. 5 (1966), 704.

Method 8

Reaction of a steroid A—(OH)$_n$ with a suitably substituted isocyanate gives a compound of the general formula (II) Above, wherein $R^2$ is $R^1$, (see for instance Kogon - J.Org.Chem. 26 (1961), 3004 and Fritz - Tetrahedron 26 (1970), 5821).

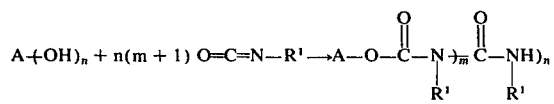

A, $m$, $n$ and $R^1$ have the meaning given in the general formula (I) above.

Method 9

A steroid isocyanate of the formula A—(O—CO—N=C=O)$_n$ is prepared by methods known per se, for instance from a steroid carbamate A—(O—CO—NH$_2$) and phosgene.

Reaction between the steroid isocyanate and a suitably substituted amine gives a compound of the general formula (II), wherein $R^2$ is hydrogen and $m$ is one (see for instance Capp - J.Chem.Soc. 1948, 1340 and Goedeler - Chem.Ber. 99 (1966):11, 3572.

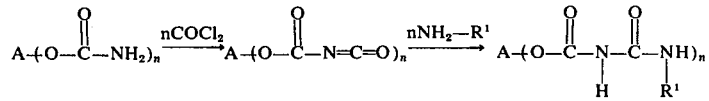

A, $n$ and $R^1$ have the meaning given in the general formula (I) above.

Method 10

An isocyanate of the formula O=C=N—CO—N-H—$R^1$ is prepared by methods known per se, for instance by reaction of a suitably substituted chloroformyl derivative of the formula Cl—CO—NH—$R^1$ with alkali cyanate.

A compound of the general formula (II) above, wherein $m$ is one and $R^2$ is hydrogen, is obtained by reaction of the above isocyanate with a steroid A—(OH)$_n$ (see for instance Haas - Chem.Ber. 97 (1964), 2189).

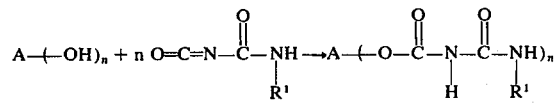

A, $n$ and $R^1$ have the meaning given in the general formula (I) above.

The methods used when synthetizing the compounds of the general formula (I), (II), (III) of the invention have to be chosen in such a way that all groups in the starting materials involved are compatible with the method used or, if necessary, sensitive groups are protected during the reaction and then converted to the desired groups so that compounds of the general formula (I) above are obtained.*

*See for instance. C. Djerassi - Steroid Reactions, Chapter 1, p. 1–87 and McOmie - Protective Groups in Organic Chemistry.

The reactions mentioned above for the preparation of starting materials are carried out in such a manner that each group of the compounds involved is compatible with the process in question or protected when necessary.

The compounds of the invention are generally characterized by the pharmacological activity hereinbefore stated, making them useful in counteracting certain physiological abnormalities in a living animal body. Effective quantities of the pharmacologically active compounds of the invention may be administered to a living animal body in anyone of various ways, for example orally as in capsules or tablets, parenterally in the form of sterile solutions, suspensions and by pellet implantation. Among routes of parenteral administration are intravenously, subcutaneously, intramuscularly, intraperitoneally, intraarticularly and intradermally. Other modes of administration are vaginally, rectally, and topically as e.g. in the form of ointments, suppositories and powders.

As representative of living animal bodies, which may be treated with the compounds and compositions of the invention, and according to the method of treatment of the invention, for alleviation of the same and/or similar conditions as those described, the following may be mentioned:

domestic animals such as dogs and cats, farm animals such as horses, cows, sheep and goats.

Pharmaceutical formulations are usually prepared from a predetermined quantity of one or more of the compounds of the invention. Such formulations may take the form of powder, syrups, suppositories, ointments, solutions, pills, capsules, pellets or tablets, suspensions, emulsions, oil solutions etc., with or without, but preferably with, any one of a large variety of pharmaceutically acceptable vehicles or carriers. When in a mixture with a pharmaceutical vehicle or carrier, the active ingredient usually comprises from about 0.01 to about 75 percent, normally from about 0.05 to about 15 percent, by weights of the composition. Carriers such as starch, sugar talc, commonly used synthetic and natural gums, water, and the like, may be used in such formulations. Binders such as polyvinylpyrrolidene and lubricants such as sodium stearate, may be used to form tablets. Disintegrating agents such as sodium bicarbonate may also be included in tablets.

Although relatively small quantities of the active materials of the invention, even as low as 5.0 milligrams, may be used in cases of administration to subjects having a relatively low body weight, unit dosages are preferably five milligrams or above and preferably 25, 50, or 100 milligrams, or even higher, depending of course upon the subject treated and the particular result desired, as will be apparent to one skilled in the art.

Broader ranges appear to be 1 to 1000 milligrams per unit dose. The active agents of the invention may be combined for administration with other pharmacologically active agents such as analgesics, steroids or hormones, or the like, or with buffers, antacids or the like, and the proportion of the active agent or agents in the compositions may be varied widely. It is only necessary that the active ingredient of the invention constitutes an effective amount, i.e. such that a suitable effective dosage will be obtained consistent with the dosage form employed. Obviously, several unit dosage forms maybe be administered at about the same time. The exact individual dosages as well as daily dosages in a particular case will of course be determined according to well established medical and/or veterinary principles. As a rule, however, when used therapeutically, the present compounds may be administered in a quantity of 1 to 1000 milligrams, preferred ranges being 1–100 milligrams, per day and subject divided in 1 or more doses, over a suitable period and depending upon the living animal body and the type of living animal body being treated.

The following examples are intended to illustrate but not to limit the scope of the invention.

EXAMPLE 1

A solution of 13.8 g sodium nitrite in 25 ml water is slowly added with vigorous stirring to a solution of 19.7 g dehydroepiandrosterone-3$\beta$-N-(2-chloroethyl) carbamate (prepared according to Example 6) in 380 ml formic acid. The temperature is maintained between 0° – +5°C during the addition.

After the addition the reaction mixture is allowed to stand at +5° for 1 h, whereupon the precipitate formed is collected and washed with ice-water.

The product is the dehydroepiandrosterone-3$\beta$-N-(2-chloroethyl)-N-nitroso carbamate which after recrystallisation from acetone-water has a melting point of 172°–4°C and is pure in TLC.

The structure is confirmed by IR and analysis for Cl and N.

In substantially the same manner the following compounds are obtained from the corresponding starting materials (prepared according to Examples 6, 7 or 8).
  estradiol-3-acetate-17$\beta$-N-(2-chloroethyl)-N-nitroso carbamate, mp. 164°C, from estradiol-3-acetate-17$\beta$-N-(2-chloroethyl) carbamate,
  androsterone-3$\alpha$-N-(2-chloroethyl)-N-nitroso carbamate, mp 96°C, from androsterone-3$\alpha$-N-(2-chloroethyl) carbamate,
  epiandrosterone-3$\beta$-N-(2-chloroethyl)-N-nitroso carbamate, mp. 138°C, from epiandrosterone-3$\beta$-(2-chloroethyl) carbamate,
  testosterone-17$\beta$-N-(2-chloroethyl)-N-nitroso carbamate, mp. 110°C, from testosterone-17$\beta$-N-(2-chloroethyl) carbamate,
  androstenediol-3$\beta$-acetate-17$\beta$-N-(2-chloroethyl)-N-nitroso carbamate, mp. 117°C, from androstenediol-3$\beta$-acetate-17$\beta$-N-(2-chloroethyl) carbamate,
  dehydroepiandrosterone-3$\beta$-N-(2-bromoethyl)-N-nitroso carbamate, mp. 161°C, from dehydroepiandrosterone-3$\beta$-N-(2-bromoethyl) carbamate,
  dehydroepiandrosterone-3$\beta$-N-(3-chloropropyl)-N-nitroso carbamate, mp. 98°C, from dehydroepiandrosterone-3$\beta$-(3-chloropropyl) carbamate,
  dehydroepiandrosterone - 3$\beta$-N-(3-bromopropyl)-N-nitroso carbamate, mp. 101°C, from dehydroepiandrosterone-3$\beta$-N-(3-bromopropyl) carbamate,
  pregnenolone-3$\beta$-N-(2-chloroethyl)-N-nitroso carbamate, mp. 160°C, from pregenolone-3$\beta$-N-(2-chloroethyl) carbamate,
  cholesterol-3$\beta$-N-(2-chloroethyl)-N-nitroso carbamate, mp. 127°C, from cholesterol-3$\beta$-N-(2-chloroethyl) carbamate.

For comparison purposes in the biological tests the following compound is obtained in substantially the same manner from the corresponding starting material prepared according to Example 6.
  dehydroepiandrosterone-3$\beta$-N-ethyl-N-nitroso carbamate, mp. 177°–179°C.

EXAMPLE 2

To a solution of 3.8 g dehydroepiandrosterone-3$\beta$-N-(2-chloroethyl) carbamate (prepared according to Example 6) in a mixture of 60 ml acetic acid and 60 ml acetic anhydride, 15 g of sodium nitrite is added with cooling and vigorous stirring over a period of 5 hrs. The temperature is maintained at 0°C during the addition.

The reaction mixture is allowed to stand at 0°C for 12 hrs. and then it is poured on an ice-water mixture. After the ice has melted the precipitate is filtered off and washed with water.

The product is dehydroepiandrosterone-3$\beta$-N-(2-chloroethyl)-N-nitroso carbamate which after recrystallisation from acetonewater has a melting point of 172°–4°C and is pure in TLC.

The structure is confirmed by IR and analysis for Cl and N.

In substantially the same manner the following compounds are obtained from the corresponding starting material (prepared according to Examples 6, 7 or 8).
  estrone-3-N-(2-chloroethyl)-N-nitroso carbamate, mp. 171°C, from estrone-3-N-(2-chloroethyl) carbamate,
  estradiol-17$\beta$-acetate-3-N-(2-chloroethyl)-N-nitroso carbamate, mp. 130°C, from estradiol-17$\beta$-acetate-3-N-(2-chloroethyl) carbamate,
  estradiol-3-methylether-17$\beta$-N-(2-chloroethyl)-N-nitroso carbamate, mp. 85°C, from estradiol-3-methylether-17$\beta$-N-(2-chloroethyl) carbamate,
  estradiol-3-benzoate-17$\beta$-N-(2-chloroethyl)-N-nitroso carbamate, mp. 140°C, from estradiol-3-benzoate-17$\beta$-N-(2-chloroethyl) carbamate,
  androsterone-3$\alpha$-N-(2-chloroethyl)-N-nitroso carbamate, mp. 96°C, from androsterone-3$\alpha$-N-(2-chloroethyl) carbamate,
  dihydrotestosterone-17$\beta$-N-(2-chloroethyl)-N-nitroso carbamate, mp. 110°C, from dihydro-testosterone-17$\beta$-N-(2-chloroethyl) carbamate,
  19-nortestosterone-17$\beta$-N-(2-chloroethyl)-N-nitroso carbamate, mp. 97°C, from 19-nortestosterone-17$\beta$-N-(2-chloroethyl) carbamate,
  androstenediol-17$\beta$-acetate-3$\beta$-N-(2-chloroethyl)-N-nitroso carbamate, mp. 140°C, from androstenediol-17$\beta$-acetate-3$\beta$-N-(2-chloroethyl) carbamate,
  androstenediol-3$\beta$,17$\beta$-bis-/N-(2-chloroethyl)-N-nitroso carbamate/, mp. 120°C, from androstenediol-3$\beta$, 17$\beta$-bis/N-(2-chloroethyl) carbamate/,
  androstanediol-3$\alpha$,17$\beta$-bis/N-(2-chloroethyl)-N-nitroso carbamate/, mp. 83°C, from androstanediol-3$\alpha$,17$\beta$-bis/N-(2-chloroethyl) carbamate/, dehydroepiandrosterone-3β-N-(2-chloropropyl)-N-nitroso carbamate, mp. 130°C, from dehydroepiandrosterone-3β-N-(2-chloropropyl) carbamate, pregnenolone-3β-N-(2-chloroethyl)-N-nitroso carbamate, mp. 160°C, from pregnenolone-3β-N-(2-chloroethyl) carbamate, cholesterol-3β-N-(2-chloroethyl)-N-nitroso carbamate, mp. 127°C, from cholesterol-3β-N-(2-chloroethyl) carbamate,

EXAMPLE 3

7.6 g dehydroepiandrosterone-3β-N-(2-chloroethyl) carbamate (prepared according to Example 6) is dissolved in a mixture of 45 ml acetic acid and 5 ml acetic anhydride. The solution is cooled in an ice-salt mixture and a rapid stream of nitrogen trioxide is bubbled through the solution until it is saturated.

The solution is maintained at 0°C for 24 hrs whereupon it is poured out in an ice-water mixture.

The reaction product is extracted with ether and the ether solution is washed with 5 % sodium bicarbonate solution and finally with water. After drying the solution over sodium sulphate the solvent is evaporated.

The residual yellow oil is dehydroepiandrosterone-3β-N-(2-chloroethyl)-N-nitroso carbamate which after drying in vacuo shows sufficient analytical purity with respect to Cl and N and is pure in TLC.

The structure is confirmed by IR and NMR.

In substantially the same manner the following compounds are obtained from the corresponding starting material (prepared according to Example 6, 7 or 8).

estrone-3-N-(2-chloroethyl)-N-nitroso carbamate, mp. 171°C, from estrone-3-N-(2-chloroethyl) carbamate, pregnenolone-3β-N-(2-chloroethyl)-N-nitroso carbamate, mp. 160°C, from pregnenolone-3β-N-(2-chloroethyl) carbamate, cholesterol-3β-N-(2-chloroethyl)-N-nitroso carbamate, mp. 127°C, from cholesterol-3β-N-(2-chloroethyl) carbamate.

EXAMPLE 4

To a solution of 12.3 g cholesterol-3β-N-(2-chloroethyl) carbamate (prepared according to Example 6) in 600 ml formic acid and 150 ml acetic anhydride is added 5.9 g potassium acetate and 0.5 g phosphorous pentaoxide. To the mixture is added with cooling and vigorous stirring a solution of 4.1 g nitrosyl chloride in 8.5 ml acetic anhydride.

After the addition the mixture is allowed to stand at room temperature for 20 minutes and then poured in an ice-water mixture, whereupon the precipitate formed is collected and washed with ice-water.

The product is cholesterol-3β-N-(2-chloroethyl)-N-nitroso carbamate which after recrystallisation from acetone-water has a melting point of 127°C and is pure in TLC.

The structure is confirmed by IR and analysis for Cl and N.

In substantially the same manner the following compounds are obtained from the corresponding starting material (prepared according to Examples 6, 7 or 8).

estrone-3-N-(2-chloroethyl)-N-nitroso carbamate, mp. 171°C, from estrone-3-N-(2-chloroethyl) carbamate, dehydroepiandrosterone-3β-N-(2-chloroethyl)-N-nitroso carbamate, mp. 172°-174°C, from dehydropiandrosterone-3β-N-(2-chloroethyl) carbamate, pregnenolone-3β-N-(2-chloroethyl)-N-nitroso carbamate, mp. 160°C, from pregnenolone-3β-N-(2-chloroethyl) carbamate.

EXAMPLE 5

3.8 g dehydroepiandrosterone-3β-N-(2-chloroethyl) carbamate (prepared according to Example 6) is slowly added with vigorous stirring at 0°C to a solution of 1.38 g nitrogen tetraoxide and 2.46 g anhydrous sodium acetate in 100 ml acetic acid.

After stirring at 0°C for 1 h the mixture is poured into an excess of water and ice. The reaction product is extracted with ether and the ether solution is washed with 5 % sodium bicarbonate solution. After drying the solution over sodium sulphate the solvent is evaporated.

The residual yellow oil is dehydroepiandrosterone-3β-N-(2-chloroethyl)-N-nitroso carbamate which after drying in vacuo shows sufficient analytical purity with respect to Cl and N.

The structure is confirmed by IR and NMR.

In substantially the same manner the following compounds are obtained from the corresponding starting material (prepared according to Example 6, 7, 8 or 9).

17β-estradiol-3-N-(2-chloroethyl)-N-nitroso carbamate from 17β-estradiol-3-N-(2-chloroethyl) carbamate, estradiol-3-N-(2-chloroethyl)-N-nitroso carbamate-17β-(p-propoxyphenyl-propionate) from estradiol-3-N-(2-chloroethyl) carbamate-17β-(p-propoxyphenyl propionate), estradiol-3-N-(2-chloroethyl)-N-nitroso carbamate-17β-dihydrogen phosphate from estradiol-3-N-(2-chloroethyl) carbamate-17β-dihydrogen phosphate, estradiol-3-N-(2-chloroethyl)-N-nitroso carbamate-17β-sodium sulphate from estradiol-3-N-(2-chloroethyl) carbamate-17β-sodium sulphate, estradiol-17β-N-(2-chloroethyl)-N-nitroso carbamate-3-cyclopentyl ether from estradiol-17β-N-(2-chloroethyl)carbamate-3-cyclopentyl ether, estradiol-3,17β-bis/N-(2-chloroethyl)-N-nitroso carbamate/ from estradiol-3,17β-bis /N-(2-chloroethyl) carbamate/, estradiol-17β-acetate-3 /$N^2$, $N^4$-bis(2-chloroethyl)-$N^4$-nitroso allophanate/ from estradiol-17β-acetate-3-/$N^2$, $N^4$-bis (2-chloroethyl) allophanate/, estradiol-3-acetate-17β-/$N^2$-cyclohexyl-$N^4$-(2-chloroethyl)-$N^4$-nitroso allophanate/from estradiol-3-acetate-17β-/$N^2$-cyclohexyl-$N^4$-(2-chloroethyl) allophanate/, estriol-16α,17β-diacetate-3-N-(2-chloroethyl)-N-nitroso carbamate from estriol-16α,17β-diacetate-3-N-(2-chloroethyl) carbamate, estriol-3-N-(-b 2-chloroethyl)-N-nitroso carbamate-16α,17β-bishemisuccinate from estriol-3-N-(2-chloroethyl) carbamate-16α,17β-bis hemisuccinate, estriol-3-acetate-16α,17β-bis-/N-(2-chloroethyl)-N-nitroso carbamate/ from estriol-3-acetate-16α,17β-bis/N-(2-chloroethyl) carbamate/, estriol-3,16α-diacetate-17β-/$N^2$-cyclohexyl-$N^4$-(2-chloroethyl)-$N^4$-nitroso allophanate/ from estriol-3,16α-diacetate-17β-/$N^2$-cyclohexyl-$N^4$-(2-chloroethyl) carbamate/, 17α-ethynylestradiol-17β-acetate-3-N-(2-chloroethyl)-N-nitroso carbamate from 17α-ethynylestradiol-17β-acetate-3-N-(2-chloroethyl) carbamate, 17α-ethynylestradiol-3-acetate-17β-N-(2-chloroethyl)-N-nitroso carbamate from 17α-ethynylestradiol-3-acetate-17β-N-(2-chloroethyl) carbamate, 17α-ethynylestradiol-17β-acetate-3-$N^2$, $N^4$-bis(2-chloroethyl)-$N^4$-nitroso allophanate/ from 17α-ethynylestradiol-17β-acetate-3-N/$N^2$,$N^4$-bis (2-chloroethyl) allophanate/, dihydrotestosteron-17β-/$N^2$-cyclohexyl-$N^4$-(2-chloroethyl)-$N^4$-nitroso allophanate/from dihydrotestosterone-17β-/$N^2$-cyclohexyl-$N^4$-(2-chloroethyl) allophanate/, testosterone-17β-/$N^2$-cyclohexyl-$N^4$-(2-chloroethyl)-$N^4$-nitroso allophanate/from testosterone-17β-/$N^2$-cyclohexyl-$N^4$-(2-chloroethyl) allophanate/, 19-nortestosterone-17β-/$N^2$-cyclohexyl-$N^4$-(2-chloroethyl)-$N^4$-nitroso allophanate/ from 19-nortestosterone-17β-/$N^2$-cyclohexyl-$N^4$-(2-chloroethyl)allophanate/, 17α-ethyl-19-nortestosteron-17β-N-(2-chloroethyl)-N-nitroso carbamate from 17α-ethyl-19-nortestosterone-17β-N-(2-chloroethyl) carbamate, androstanediol-3α-N-(2-chloroethyl)-N-nitroso carbamate from androstanediol-3α-N-(2-chloroethyl) carbamate, androstanediol-3α-N-(2-chloroethyl)-N-nitroso carbamate-17β-oenanthate from androstanediol-3α-N-(2-chloroethyl) carbamate-17β-oenanthate, androstanediol-[3α-N-(2-chloroethyl)-N-nitroso carbamate-17β-dihydrogen phosphate from androstanediol-3α-N-(2-chloroethyl) carbamate-17β-dihydrogen phosphate, etiocholanolone-3α-N-(2-chloroethyl)-N-nitroso carbamate from etiocholanolone-3α-N-(2-chloroethyl) carbamate, dehydroepiandrosterone-3β-n(2-fluoroethyl)-N-nitroso carbamate from dehydroepiandrosterone-3β-N-(2-fluoroethyl) carbamate, dehydroepiandrosterone-3β-/$N^4$-(2-chloroethyl)-$N^4$-nitroso allophanate/from dehydroepiandrosterone-3β-/$N^4$-(2-chloroethyl) allophanate/, dehydroepiandrosterone-3β-/$N^2$-methyl-$N^4$-(2-chloroethyl)-$N^4$-nitroso allophanate/from dehydroepiandrosterone-3β-/$N^2$-methyl-$N^4$-(2-chloroethyl) allophanate/, dehydroepiandrosterone-3β-/$N^2$-n-butyl-$N^4$-(2-chloroethyl)-$N^4$-nitroso allophanate/ from dehydroepiandrosterone-3β-/$N^2$-n-butyl-$N^4$-(2-chloroethyl) allophanate/, dehydroepiandrosterone-3β-/$N^2$,$N^4$-bis(2-chloroethyl)-$N^4$-nitroso allophanate/ from dehydroepiandrosterone-3β-/$N^2$,$N^4$-bis(2-chloroethyl) allophanate/, dehydroepiandrosterone-3β-/$N^2$-cyclohexyl-$N^4$-(2-chloroethyl)-$N^4$-nitroso allophanate/ from dehydroepiandrosterone-3β-/$N^2$-cyclohexyl-$N^4$-(2-chloroethyl) allophanate/, dehydroepiandrosterone-3β-/$N^2$-phenyl-$N^4$-(2-chloroethyl)-$N^4$-nitroso allophanate/ from dehydroepiandrosterone-3β-/$N^2$-phenyl-$N^4$-(2-chloroethyl) allophanate/, dehydroepiandrosterone-3β-/$N^2$-(p-chlorophenyl)-$N^4$-(2-chloroethyl)-$N^4$-nitroso allophanate/ from dehydroepiandrosterone-3β-$N^2$-(p-chlorophenyl)-$N^4$-(2-chloroethyl) allophanate/, dehydroepiandrosterone-3β-/$N^2$-(p-methoxyphenyl)-$N^4$-(2-chloroethyl)-$N^4$-nitroso allophanate/ from dehydroepiandrosterone-3β-/$N^2$-(p-methoxyphenyl)-$N^4$-(2-chloroethyl) allophanate/, 17α-hydroxy-progesterone,17α-N-(2-chloroethyl)-N-nitroso carbamate from 17α-hydroxy-progesterone,17α-N-(2-chloroethyl) carbamate, 17α-ethynyl-19-nortestosterone-17β-N-(2-chloroethyl)-N-nitroso carbamate from 17α-ethynyl-19-nortestosterone-17β-N-(2-chloroethyl) carbamate, 17α-ethynyl-19-nortestosterone-17β-/$N^2$,$N^4$-bis (2-chloroethyl)-$N^4$-nitroso allophanate/ from 17α-ethynyl-19-nortestosterone-17β-/$N^2$,$N^4$-bis (2-chloroethyl) allophanate/, norethynodrel-17β-N-(2-chloroethyl)-N-nitroso carbamate from norethynodrel-17β-N-(2-chloroethyl) carbamate, ethynodiol-17β-acetate-3β-N-(2-chloroethyl)-N-nitroso carbamate from ethynodiol-17β-acetate-3β-N-(2-chloroethyl) carbamate, ethynodiol-17β-acetate-3β-/$N^2$-cyclohexyl-$N^4$-(2-chloroethyl)-$N^4$-nitroso allophanate/ from ethynodiol-17β-acetate-3β-/$N^2$-cyclohexyl-$N^4$-(2-chloroethyl) allophanate/, deoxycorticosterone-21-N-(2-chloroethyl)-N-nitroso carbamate from deoxycorticosterone-21-N-(2-chloroethyl) carbamate, hydrocortisone-21-N-(2-chloroethyl)-N-nitroso carbamate from hydrocortisone-21-N-(2-chloroethyl) carbamate, prednisone-21-N-(2-chloroethyl)-N-nitroso carbamate from prednisone-21-N-(2chloroethyl) carbamate, prednisolone-21-N-(2-chloroethyl)-N-nitroso carbamate from prednisolone-21-N-(2-chloroethyl) carbamate, prednisolone-21-/$N^2$,$N^4$-bis (2-chloroethyl)-$N^4$-nitroso allophanate/ from prednisolone-21-/$N^2$,$N^4$-bis (2-chloroethyl)-$N^4$-nitroso allophanate/, cholesterol-3β-$N^2$-cyclohexyl-$N^4$-(2-chloroethyl)-$N^4$-nitroso allophanate/ from cholesterol-3β-/$N^2$-cyclohexyl-$N^4$-(2-chloroethyl) allophanate/, estra-1,3,5(10)-triene-3,17β-diol-16-one,17β-acetate-3-N-(2-chloroethyl)-N-nitroso carbamate from estra-1,3,5(10)-triene-3,17β-diol-16-one,17β-acetate-3-N-(2-chloroethyl) carbamate, estradiol-17β-acetate-3-N-(2-fluoroethyl)-N-nitroso carbamate from estradiol-17β-acetate-3-N-(2-fluoroethyl) carbamate, estradiol-17β-phenyl hydrogen phosphate-3-N-(2-chloroethyl)-N-nitroso carbamate from estradiol-17β-phenyl hydrogen phosphate-3-N-(2-chloroethyl) carbamate, estradiol-17β-ethyl hydrogen phosphate -3-N-(2-chloroethyl)-N-nitroso carbamate from estradiol-17β-ethyl hydrogen phosphate- 3-N-(2-chloroethyl) carbamate, estradiol-17β-valerate-3-N-(2-chloroethyl)-N-nitroso carbamate from estradiol-17β-valerate-3-N-(2-chloroethyl) carbamate, estradiol-17β-acetate-3-$N^2$-methyl-$N^4$-(2-chloroethyl)-$N^4$-nitroso allophanate/ from estradiol-17β-acetate-3-/$N^2$-methyl-$N^4$-(2-chloroethyl) allophanate/, estrone-3-/$N^2$-(4-methylcyclohexyl)-$N^4$-(2-chloroethyl)-$N^4$-nitroso allophanate/ from estrone-3-/$N^2$-

(4-methylcyclohexyl)-N$^4$-(2-chloroethyl) allophanate/, estrone-3-/N$^2$-(4-methylphenyl)-N$^4$-(2-chloroethyl)-N$^4$-nitroso allophanate/ from estrone-3-/N$^2$-(4-methylphenyl)-N$^4$-(2-chloroethyl) allophanate/, estradiol-3-methylether-17$\beta$-/N$^2$-phenyl-N$^4$-(2-chloroethyl)-N$^4$-nitroso allophanate/ from estradiol-3-methylether-17$\beta$-N$^2$-phenyl-N$^4$-(2-chloroethyl) allophanate/, estradiol-3-methylether-17$\beta$-/N$^2$-methyl-N$^4$-(2-chloroethyl)-N$^4$-nitroso allophanate from estradiol-3-methylether-17$\beta$-/N$^2$-methyl-N$^4$-(2-chloroethyl) allophanate, estradiol-3-methylether--17$\beta$-/N$^4$-(2-chloroethyl)-N$^4$-nitroso allophanate/ from estradiol-3-methylether-17$\beta$-/N$^4$-(2-chloroethyl) allophanate/, 2$\alpha$-methyl-dihydrotestosterone-17$\beta$-N-(2-chloroethyl)-N-nitroso carbamate from 2$\alpha$-methyl-dihydrotestosterone-17$\beta$-N-(2-chloroethyl) carbamate, etiocholanolone-3$\alpha$-N-(2-fluoroethyl)-N-nitroso carbamate from etiocholanolone-3$\alpha$-N-(2-fluoroethyl) carbamate, 4-methyl-testosterone-17$\beta$-N-(2-chloroethyl)-N-nitroso carbamate from 4-methyl-testosterone-17$\beta$-N-(2-chloroethyl) carbamate, 6$\alpha$-methyltestosterone-17$\beta$-N-(2-chloroethyl)-N-nitroso carbamate from 6$\alpha$-methyltestosterone-17$\beta$-N-(2-chloroethyl) carbamate, 17$\alpha$-methyltestosterone-17$\beta$-N-(2-chloroethyl)-N-nitroso carbamate from 17$\alpha$-methyltestosterone-17$\beta$-N-(2-chloroethyl) carbamate, 9$\alpha$-fluoro-11$\beta$-hydroxy-17$\alpha$-methyltestosterone-17$\beta$-N-(2-chloroethyl)-N-nitroso carbamate from 9$\alpha$-fluoro-11$\beta$-hydroxy-17$\alpha$-methyltestosterone-17$\beta$-N-(2-chloroethyl) carbamate, 7$\alpha$,17$\alpha$-dimethyltestosterone-17$\beta$-N-(2-chloroethyl)-N-nitroso carbamate from 7$\alpha$,17$\alpha$-dimethyltestosterone-17$\beta$-N-(2-chloroethyl) carbamate, androstenediol-3$\beta$-/N-(2-chloroethyl)-N-nitroso carbamate/-17$\beta$-phenyl hydrogen phosphate from androstenediol-3$\beta$-/N-(2-chloroethyl) carbamate/-17$\beta$-phenyl hydrogen phosphate, androstenediol-3$\beta$-/N-(2-chloroethyl)-N-nitroso carbamate/-17$\beta$-dihydrogen phosphate from androstenediol-3$\beta$-/N-(2-chloroethyl) carbamate-17$\beta$-dihydrogen phosphate androstenediol-3$\beta$-/N-(2-chloroethyl)-N-nitroso carbamate/-17$\beta$-dihydrogen phosphate is also converted to the following salts: monosodium-salt, disodium-salt and N-methylglucamine-salt.

androstenediol-3$\beta$-/N-(2-chloroethyl)-N-nitroso carbamate/-17$\beta$-ethyl hydrogen phosphate from androstenediol-3$\beta$-/N-(2-chloroethyl) carbamate/-17$\beta$-ethyl hydrogen phosphate, androstenediol-3$\beta$-/N-(2-chloroethyl)-N-nitroso carbamate/-17$\beta$-sodium sulphate from androstenediol-3$\beta$-/N-(2-chloroethyl) carbamate/-17$\beta$-sodium sulphate, androstenediol-3$\beta$-/N$^2$-methyl-N$^4$-(2-chloroethyl)-N$^4$-nitroso allophanate/-17$\beta$-dihydrogen phosphate from androstenediol-3$\beta$-/N$^2$-methyl-N$^4$-(2-chloroethyl) allophanate/-17$\beta$-dihydrogen phosphate, androstenediol-17$\beta$-hemisuccinate-3$\beta$-N-(2-chloroethyl)-N-nitroso carbamate from androstenediol-17$\beta$-hemisuccinate-3$\beta$-N-(2-chloroethyl) carbamate, androstenediol-17$\beta$-p-hexoxyphenylpropionate-3$\beta$-N-(2-chloroethyl)-N-nitroso carbamate from androstenediol-17$\beta$-p-hexoxyphenylpropionate, -3$\beta$-N-(2-chloroethyl) carbamate, androstenediol-17$\beta$-methylether-3$\beta$-N-(2-chloroethyl)-N-nitroso carbamate from androstenediol-17$\beta$-methylteher-3-N-(2-chloroethyl) carbamate, androstenediol-17$\beta$-benzoate-3$\beta$-N-(2-chloroethyl)-N-nitroso carbamate from androstenediol-17$\beta$-benzoate-3$\beta$-N-(2-chloroethyl) carbamate, dehydroepiandrosterone-3$\beta$-/N$^2$-(4-methylcyclohexyl)-N$^4$(2-chloroethyl)-N$^4$-nitroso allophanate/ from dehydroepiandrosterone-3$\beta$-/N-(4-methylcyclohexyl)-N$^4$-(2-chloroethyl) allophanate/, dehydroepiandrosterone-3$\beta$-N/$^2$-(3,4-dimethylphenyl)-N$^4$-(2-chloroethyl)-N$^4$-nitroso allophanate/ from dehydroepiandrosterone-3$\beta$-/N$^2$-(3,4-dimethylphenyl)-N$^4$-(2-chloroethyl) allophanate/, 17$\alpha$-allyl-estr-4-en-17$\beta$-ol,17$\beta$-N-(2-chloroethyl)-N-nitroso carbamate from 17$\alpha$-allyl-estr-4-en-17$\beta$-ol, 17$\beta$-N-(2-chloroethyl) carbamate, 17$\alpha$-ethynyl-18-methyl-19-nortestosterone-17$\beta$-N-(2-chloroethyl)-N-nitroso carbamate from 17$\alpha$-ethynyl-18-methyl-19-nortestosterone-17$\beta$-N-(2-chloroethyl) carbamate, 6$\alpha$-methyl-17$\alpha$-hydroxy-progesterone,17$\alpha$-N-(2-chloroethyl)-N-nitroso carbamate from 6$\alpha$-methyl-17$\alpha$-hydroxy-progesterone,17$\alpha$-N-(2-chloroethyl) carbamate, 6-chloro-6-dehydro-17$\alpha$-hydroxyprogesterone,17$\alpha$-N-(2-chloroethyl)-N-nitroso carbamate from 6-chloro-6-dehydro-17$\alpha$-hydroxy-progesterone,17$\alpha$-N-(2-chloroethyl) carbamate, 6-chloro-pregna-4,6-diene-3$\beta$,17$\alpha$-diol-20-one,3$\beta$-N-(2-chloroethyl-N-nitroso carbamate from 6-chloro-pregna-4,6-diene-3$\beta$,17$\alpha$-diol-20-one,3$\beta$-N-(2-chloroethyl) carbamate, ethynodiol-17$\beta$-acetate-3$\beta$-N-(2-fluoroethyl)-N-nitroso carbamate from ethynodiol-17$\beta$-acetate-3$\beta$-N-(2-fluoroethyl) carbamate, ethynodiol-17$\beta$-acetate-3$\beta$-/N$^2$-methyl-N$^4$-(2-chloroethyl)-N$^4$-nitroso allophanate/ from ethynodiol-17$\beta$-acetate-3$\beta$-/N$^2$-methyl-N$^4$-(2-chloroethyl) allophanate/, ethynodiol-17$\beta$-acetate-3$\beta$-/N$^2$-phenyl-N$^4$-(2-chloroethyl)-N-nitroso allophanate/ from ethynodiol-17$\beta$-acetate-3$\beta$-/N$^2$-phenyl-N$^4$-(2-chloroethyl) allophanate/, ethynodiol-17$\beta$-acetate-3$\beta$-/N$^2$-n-butyl-N$^4$-(2-chloroethyl)-N$^4$-nitroso allophanate/ from ethynodiol-17$\beta$-acetate-3$\beta$-/N$^2$-n-butyl-N$^4$-(2-chloroethyl) allophanate/, ethynodiol-,17$\beta$-N-(2-chloroethyl)-N-nitroso carbamate from ethynodiol-17$\beta$-N-(2-chloroethyl) carbamate, ethynodiol-17$\beta$-N-(2-chloroethyl)-N-nitroso carbamate-3$\beta$-dihydrogen phosphate from ethynodiol-17$\beta$-N-(2-chloroethyl) carbamate-3$\beta$-dihydrogen phosphate, ethynodiol-17$\beta$-N-(2-chloroethyl)-N-nitroso carbamate-3$\beta$-phenyl hydrogen phosphate from ethynodiol-17$\beta$-N-(2-chloroethyl) carbamate-3$\beta$-phenyl hydrogen phosphate, ethynodiol-17$\beta$-N-(2-chloroethyl)-N-nitroso carbamate-3$\beta$-ethyl hydrogen phosphate from ethynodiol-17$\beta$-N-(2-chloroethyl) carbamate-3$\beta$-ethyl hydrogen phosphate, ethynodiol-17β-N-(2-chloroethyl)-N-nitroso carbamate-3β-sodium sulphate from ethynodiol-17β-N-(2-chloroethyl) carbamate-3β-sodium sulphate, ethynodiol-17β-N-(2-chloroethyl)-N-nitroso carbamate-3β-oenanthate from ethynodiol-17β-N-(2-chloroethyl) carbamate-3β-oenanthate, ethynodiol-17β-acetate-3β-/$N^2$-(4-methylcyclohexyl)-$N^4$-(2-chloroethyl)-$N^4$-nitroso allophanate/ from ethynodiol-17β-acetate-3β-/$N^2$-(4-methylcyclohexyl)-$N^4$-(2-chloroethyl) allophanate/, ethynodiol-17β-acetate-3β-/$N^2$-(4-chlorophenyl)-$N^4$-(2-chloroethyl)-$N^4$-nitroso allophanate/ from ethynodiol-17β-acetate-3β-/$N^2$-(4-chlorophenyl)-$N^4$-(2-chloroethyl) allophanate/, ethynodiol-17β-acetate-3β-/$N^4$-(2-chloroethyl)-$N^4$-nitroso allophanate/ from ethynodiol-17β-acetate-3β-/$N^4$-(2-chloroethyl) allophanate/, 16-methyleneprednisolone-21-N-(2-chloroethyl)-N-nitroso carbamate from 16-methylene-prednisolone-21-N-(2-chloroethyl) carbamate;

6α-fluoro-16α-methylprednisolone-21-N-(2-chloroethyl)-N-nitroso carbamate from 6α-fluoro-16α-methylprednisolone-21-N-(2-chloroethyl) carbamate, 9α-fluoro-16α-methylprednisolone-21-N-(2-chloroethyl)-N-nitroso carbamate from 9α-fluoro-16α-methylprednisolone-21-N-(2-chloroethyl) carbamate, 9α-fluoro-16β-methylprednisolone-21-N-(2-chloroethyl)-N-nitroso carbamate from 9α-fluoro-16β-methylprednisolone-21-N-(2-chloroethyl) carbamate, 9α-fluoro-16-α-hydroxyprednisolone-21-N-(2-chloroethyl)-N-nitroso carbamate from 9α-fluoro-16α-hydroxyprednisolone-21-N-(2-chloroethyl) carbamate, 9α-fluoro-16α-hydroxyprednisolone-21-N-(2-chloroethyl)-N-nitroso carbamate, 16α,17α-acetonide from 9α-fluoro-16α-hydroxyprednisolone-21-N-(2-chloroethyl) carbamate, 16α,17α-acetonide, pregnenolone-3β-N-(2-fluoroethyl)-N-nitroso carbamate from pregnenolone-3β-N-(2-fluoroethyl) carbamate, pregnenolone-3β-/$N^2$-methyl-$N^4$-(2-chloroethyl)-$N^4$-nitroso allophanate/ from pregnenolone-3β-/$N^2$-methyl-$N^4$-(2-chloroethyl) allophanate/, pregnenolone-3β-/$N^2$-cyclohexyl-$N^4$-(2-chloroethyl)-$N^4$-nitroso allophanate/ from pregnenolone-3β-/$N^2$-cyclohexyl-$N^4$-(2-chloroethyl) allophanate/, pregnenolone-3β-/$N^2$,$N^4$-bis (2-chloroethyl)-$N^4$-nitroso allophanate/ from pregnenolone-3β-/$N^2$,$N^4$-bis (2-chloroethyl) allophanate/, pregnenolone-3β-/$N^2$-(4-methylcyclohexyl)-$N^4$-(2-chloroethyl)-$N^4$-nitroso allophanate/ from pregnenolone-3β-/$N^2$-(4-methylcyclohexyl)-$N^4$-(2-chloroethyl) allophanate/, pregnenolone-3β-/$N^2$-phenyl-$N^4$-(2-chloroethyl)-$N^4$-nitroso allophanate/ from pregnenolone-3β-/$N^2$-phenyl-$N^4$-(2-chloroethyl) allophanate/, prednisolone-21-/$N^2$-cyclohexyl-$N^4$-(2-chloroethyl)-N-nitroso allophanate/ from prednisolone-21-/$N^2$-cyclohexyl-$N^4$-(2-chloroethyl) allophanate/, cholesterol-3β-N-(2-fluoroethyl)-N-nitroso carbamate from cholesterol-3β-N-(2-fluoroethyl) carbamate, cholesterol-3β-/$N^2$-methyl-$N^4$-(2-chloroethyl)-$N^4$-nitroso allophanate/ from cholesterol-3β-/$N^2$-methyl-$N^4$-(2-chloroethyl) allophanate/, cholesterol-3β-/$N^2$-phenyl-$N^4$-(2-chloroethyl)-$N^4$-nitroso allophanate/ from cholesterol-3β-/$N^2$-phenyl-$N^4$-(2-chloroethyl) allophanate, cholesterol-3β-/$N^2$,$N^4$-bis (2-chloroethyl)-$N^4$-nitroso allophanate/ from cholesterol-3β-/$N^2$,$N^4$-bis (2-chloroethyl) allophanate/, ergosterol-3β-N-(2-chloroethyl)-N-nitroso carbamate from ergosterol-3β-N-(2-chloroethyl) carbamate, cholesterol-3β-/$N^4$-(2-chloroethyl)-$N^4$-nitroso allophanate/ from cholesterol-3β-/$N^4$-(2-chloroethyl) allophanate/, estra-1,3,5(10),16-tetraen-3-ol, 3-N-(2-chloroethyl)-N-nitroso carbamate from estra-1,3,5(10),16-tetraen-3-ol, 3-N-(2-chloroethyl) carbamate.

corticosterone-21-acetate-11β-N-(2-chloroethyl)-N-nitroso carbamate from corticosterone-21-acetate-11β-N-(2-chloroethyl) carbamate, prednisolone-11β-N-(2-chloroethyl)-N-nitroso carbamate from prednisolone-11β-N-(2-chloroethyl) carbamate, prednisolone-11β-/N-(2-cloroethyl)-N-nitroso carbamate/-21-dihydrogen phosphate from prednisolone-11β-/N-(2-chloroethyl) carbamate/-21-dihydrogen phosphate, prednisolone-11β-/N-(2-chloroethyl)-N-nitroso carbamate/-21-ethyl hydrogen phosphate from prednisolone-11β-/N-(2-chloroethyl) carbamate/-21-ethyl hydrogen phosphate, prednisolone-11β-/N-(2-chloroethyl)-N-nitroso carbamate/-21-phenyl hydrogen phosphate from prednisolone-11β-/N-(2-chloroethyl) carbamate/-21-phenyl hydrogen phosphate, prednisolone-11β-/N-(2-chloroethyl)-N-nitroso carbamate/-21-pivalate from prednisolone-11β-/N-(2-chloroethyl) carbamate/-21-pivalate, prednisolone-11β-/N-(2-chloroethyl)-N-nitroso carbamate/21-hemisuccinate from prednisolone-11β-/N-(2-chloroethyl) carbamate/-21-hemisuccinate, prednisolone-11β-/N-(2-chloroethyl)-N-nitroso carbamate/-21-acetate from prednisolone-11β-/N-(2-chloroethyl) carbamate/-21-acetate, prednisolone-11β-/N-(2-chloroethyl)-N-nitroso carbamate/-21-benzoate from prednisolone-11β-/N-(2-chloroethyl) carbamate/-21-benzoate, prednisolone-11β-/N-(2-chloroethyl)-N-nitroso carbamate/-21-3,3-dimethyl butyrate from prednisolone-11β-/N-(2-chloroethyl) carbamate/-21-3,3-dimethyl butyrate, prednisolone-11β-/N-(2-chloroethyl)-N-nitroso carbamate/-21-oenanthate from prednisolone-11β-/N-(2-chloroethyl) carbamate-21-oenanthate,

EXAMPLE 6

A solution of 12.8 g 2-chloroethylamine hydrochloride in 80 ml water is treated with 58 ml 2—N NaOH. The solution is extracted with 4 × 50 ml chloroform. After drying over anhydrous sodium sulphate 15 ml triethylamine is added to the chloroform solution. The solution is added dropwise with stirring and cooling to a solution of 35.1 g dehydroepiandrosterone-3β-chloroformate (which is obtained from dehydroepiandrosterone and phosgene) dissolved in 250 ml chloroform. After the addition the mixture is allowed to stand at room temperature for 3 hrs. The solution is washed with 2 × 150 ml water, dried over anhydrous sodium sulphate and evaporated to dryness.

The residue is dehydroepiandrosterone-3β-N-(2-chloroethyl) carbamate which after crystallisation from boiling acetone has a melting point of 160°–2°C and is pure in TLC.

The structure is confirmed by IR, NMR and analysis for Cl and N.

Dehydroepiandrosterone-3β-N-(2-chloroethyl) carbamate prepared above is also reduced with sodium borohydride to androstenediol-3β-N-(2-chloroethyl) carbamate, mp.198°–201°C, which then is phosphorylated with phenyl phosphorodichloridate to androstenediol-3β-/N-(2-chloroethyl) carbamate/-17β-phenyl hydrogen phosphate, or is phosphorylated with phosphorus oxychloride to androstenediol-3β-/N-(2-chloroethyl) carbamate-17β-dihydrogen phosphate, or is phosphorylated with ethyl phosphorodichloridate to androstenediol-3β-/N-(2-chloroethyl) carbamate/-17β-ethyl hydrogen phosphate, or is esterified with sulfuric acid to androstenediol-3β-/N-(2-chloroethyl) carbamate/-17β-sodium sulphate, or is esterified with succinic acid to androstenediol-17β-hemisuccinate-3β-N-(2-chloroethyl) carbamate, or is esterified with p-hexoxylphenylpropionic acid to androstenediol-17β-p-hexoxyphenylpropionate-3β-N-(2-chloroethyl) carbamate, or is etherified to androstenediol-17β-methylether-3β-N-(2-chloroethyl) carbamate, or is esterified with benzoic acid to androstenediol-17β-benzoate-3β-N-(2-chloroethyl) carbamate.

In substantially the same manner as given for dehydroepiandrosterone-3β-N-(2-chloroethyl) carbamate above the following compounds are obtained (having structures confirmed by IR, NMR and analysis for Cl and N, and being pure in TLC) from the corresponding substituted amine and a steroid chloroformate given below:

estrone-3-N-(2-chloroethyl) carbamate, mp. 125°C, from estrone-3-chloroformate (which is obtained from estrone and phosgene), estrone-3-N-(2-chloroethyl) carbamate is also reduced with sodium borohydride to 17β-estradiol-3-N-(2-chloroethyl) carbamate, mp. 90°C, which then is phosphorylated with phosphorus oxychloride to estradiol-3-N-(2-chloroethyl) carbamate-17β-dihydrogen phosphate, or is esterified with sulfuric acid to estradiol-3-N-(2-chloroethyl) carbamate-17β-sodium sulphate, or is phosphorylated with phenyl phosphorodichloridate to estradiol-17β-phenyl hydrogen phosphate-3-N-(2-chloroethyl) carbamate, or is phosphorylated with ethyl phosphorodichloridate to estradiol-17β-ethyl hydrogen phosphate-3-N-(2-chloroethyl) carbamate, or is esterified with valeric acid to estradiol-17β-valerate-3-N-(2-chloroethyl) carbamate.

estradiol-17β-acetate-3-N-(2-chloroethyl) carbamate, mp. 172°C, from estradiol-17β-acetate-3-chloroformate (which is obtained from estradiol-17β-acetate and phosegene), estradiol-3-methylether-17β-N-(2-chloroethyl) carbamate, mp. 151°C, from estradiol-3-methyl ether-17β-chloroformate ((which is obtained from estradiol-3-methylether and phosgene), estradiol-3-acetate-17β-N-(2-chloroethyl) carbamate, mp. 110°–12°C, from estradiol-3-acetate-17β-chloroformate (which is obtained from 17β-estradiol-3-acetate and phosgene), estradiol-3-benzoate-17β-N-(2-chloroethyl) carbamate, mp. 160°C, from estradiol-3-benzoate-17β-chloroformate (which is obtained from estradiol-3-benzoate and phosgene), androsterone-3α-N-(2-chloroethyl) carbamate, mp. 124°–126°C, from androsterone-3α-chloroformate (which is obtained from androsterone and phosgene), androsterone-3α-N-(2-chloroethyl) carbamate is also reduced with sodium borohydride to androstanediol-3α-N-(2-chloroethyl carbamate, mp. 200°–204°C, which then is esterified with oenantic acid to androstanediol-3-α-N-(2-chloroethyl) carbamate-17-oenanthate, or is phosphorylated with phosphorus oxychloride to androstanediol-3α-N-(2-chloroethyl) carbamate-17-dihydrogen phosphate, epiandrosterone-3β-N-(2-chloroethyl) carbamate, mp. 120°–122°C, from epiandrosterone-3β-chloroformate (which is obtained from epiandrosterone and phosgene), dihydrotestosterone-17β-N-(2-chloroethyl) carbamate, mp. 120°–125°C, from dihydrotestosterone-17β-chloroformate (which is obtained from dihydrotestosterone and phosgene), testosterone-17β-N-(2-chloroethyl) carbamate, mp. 192°C, from testosterone-17β-chloroformate (which is obtained from testosterone and phosgene), 19-nortestosterone-17β-N-(2-chloroethyl) carbamate, isolated as an oil, from 19-nortestosterone-17β-chloroformate (which is obtained from 19-nortestosterone and phosgene), androstenediol-17β-acetate-3β-N-(2-chloroethyl) carbamate, mp. 141°C, from androstenediol-17β-acetate-3β-chloroformate (which is obtained from androstenediol-17β-acetate and phosgene), androstenediol-3β-acetate-17β-N-(2-chloroethyl) carbamate, mp. 185°C, from androstenediol-3β-acetate-17β-chloroformate (which is obtained from androsenediol-3β-acetate and phosgene), androstenediol-3β,17β-bis/N-(2-chloroethyl) carbamate/, mp. 105°–110°C, from androstenediol-3β,17β-bis chloroformate (which is obtained from androstenediol and phosgene), androstanediol-3α,17β-bis/N-(2-chloroethyl carbamate/, mp. 134°C, from androstanediol-3α,17β-bis chloroformate (which is obtained from androstenediol and phosgene), dehydroepiandrosterone-3β-N-(2-bromoethyl) carbamate, mp. 179°–80°C, from dehydroepiandrosterone-3β-chloroformate, dehydroepiandrosterone-3β-N-(2-chloropropyl) carbamate, mp. 158°–160°C, from dehydroepiandrosterone-3β-chloroformate, dehydroepiandrosterone-3β-N-(3-chloropropyl) carbamate, mp. 140°C, from dehydroepiandrosterone-3β-chloroformate, dehydroepiandrosterone-3β-N-(3-bromopropyl) carbamate, mp. 132°–135°C, from dehydroepiandrosterone-3β-chloroformate, pregnenolone-3β-N-(2-chloroethyl) carbamate, mp. 158°C, from pregnenolone-3β-chloroformate (which is obtained from pregnenolone and phosgene), hydrocortisone-21-N-(2-chloroethyl) carbamate, mp. 164°–166°C, from hydrocortisone-21-chloroformate (which is obtained from hydrocortisone and phosgene), prednisone-21-N-(2-chloroethyl) carbamate (isolated as an oil) from prednisone-21-chloroformate (which is obtained from prednisone and phosgene), prednisolone-21-N-(2-chloroethyl) carbamate, mp. 155°–160°C, from prednisolone-21-chloroformate (which is obtained from prednisolone and phosgene), cholesterol-3$\beta$-N-(2-chloroethyl) carbamate, mp. 127°C, from cholesterol-3$\beta$-chloroformate (which is obtained from cholesterol and phosgene), dehydroepiandrosterone-3$\beta$-N-ethylcarbamate, mp. 179°–81°C, from dehydroepiandrosterone-3$\beta$-chloroformate, dehydroepiandrosterone-3$\beta$-N-(2-chloroethyl)-N-methyl carbamate, mp. 164°C, from dehydroepiandrosterone-3$\beta$-chloroformate, 16-methylene-prednisolone-b 21-N-(2-chloroethyl) carbamate (isolated as an oil) from 16-methylene prednisolone, 6$\alpha$-fluoro-16$\alpha$-methylprednisolone-21-N-(2-chloroethyl) carbamate (isolated as an oil) from 6$\alpha$-fluoro-16$\alpha$-methylprednisolone, 9$\alpha$-fluoro-16$\alpha$-methylprednisolone-21-N-(2-chloroethyl) carbamate (isolated as an oil) from 9$\alpha$-fluoro-16$\alpha$-methylprednisolone, 9$\alpha$-fluoro-16$\beta$-methylprednisolone-21-N-(2-chloroethyl) carbamate (isolated as an oil) from 9$\alpha$-fluoro-16$\beta$-methylprednisolone, 9$\alpha$-fluoro-16$\alpha$-hydroxy-prednisolone-21N-(2-chloroethyl) carbamate (isolated as an oil) from 9$\alpha$-fluoro-16$\alpha$-hydroxyprednisolone, 9$\alpha$-fluoro-16$\alpha$-hydroxyprednisolone-21-N-(2-chloroethyl) carbamate, 16$\alpha$,17$\alpha$-acetonide (isolated as an oil) from 9$\alpha$-fluoro-16$\alpha$-hydroxyprednisolone-16$\alpha$,17$\alpha$-acetonide,

EXAMPLE 7

To a solution of 3.5 g dehydroepiandrosterone in 50 ml 3-chloropropylisocyanate is added 0.3 g DABCO. The temperature of the reaction mixture is held at 60°C for 48 hrs.

The solvent is removed in vacuo and the residual oil is dissolved in a chloroform-benzene mixture 1:9 and chromatographed on neutral alumina. Undesired impurities are removed by elution with the same solvent mixture. The desired product is then eluated with chloroform-benzene (4:6).

The eluate is evaporated and the residual oil dried in vacuo. The substance is dehydroepiandrosterone-3$\beta$-N-(3-chloropropyl) carbamate which has sufficient analytical purity with respect to Cl and N and is pure in TLC.

The structure is confirmed by IR and NMR.

In substantially the same manner the following compounds are obtained as oils, unless otherwise stated, (having structures confirmed by IR, NMR and analysis for Cl and N, and being pure in TLC) from the corresponding substituted isocyanate and a steroid compound given below:

estradiol-3-N-(2-chloroethyl) carbamate-17$\beta$-(p-propoxyphenylpropionate) from estradiol-17$\beta$-(p-propoxyphenyl propionate), estradiol-17$\beta$-N-(2-chloroethyl) carbamate-3-cyclopentyl ether from 17$\beta$-estradiol-3-cyclopentyl ether, estradiol-3,17$\beta$-bis-N-(2-chloroethyl) carbamate, mp. 130°–135°C, from 17$\beta$-estradiol-3-N-(2-chloroethyl) carbamate, estriol-16$\alpha$,17$\beta$-diacetate-3-N-(2-chloroethyl) carbamate from estriol-16$\alpha$,17$\beta$-diacetate, estriol-3-N-(2-chloroethyl) carbamate-16$\alpha$,17$\beta$-bishemisuccinate from estriol-16$\alpha$,17$\beta$-bishemisuccinate, estriol-3-acetate-16$\alpha$,17$\beta$-bis-/N-(2-chloroethyl) carbamate/from estriol-3-acetate, 17$\alpha$-ethynylestradiol-17$\beta$-acetate-3-N-(2-chloroethyl) carbamate from 17$\alpha$-ethynylestradiol-17$\beta$-acetate, 17$\alpha$-ethynylestradiol-3-acetate-17$\beta$-N-(2-chloroethyl) carbamate from 17$\alpha$-ethynylestradiol-3-acetate, 17$\alpha$-ethyl-19-nortestosterone-17$\beta$-N-(2-chloroethyl) carbamate from 17$\alpha$-ethyl-19-nortestosterone, etiocholanolone-3$\alpha$-N-(2-chloroethyl) carbamate from etiocholnolone, dehydroepiandrosterone-3$\beta$-N-(2-fluoroethyl) carbamate from dehydroepiandrosterone, 17$\alpha$-hydroxi-progesterone,17$\alpha$-N-(2-chloroethyl) carbamate from 17$\alpha$-hydroxy-progesterone, 17$\alpha$-ethynyl-19-nortestosterone-17$\beta$-N-(2-chloroethyl) carbamate from 17$\alpha$-ethynyl-19-nortestosterone, 17$\alpha$-ethynyl-19-nortestosterone-17$\beta$-N-(2-chloroethyl) carbamate is also reduced with LiAlH$_4$ to ethynodiol-17$\beta$-N-(2-chloroethyl) carbamate, which then is phosphorylated with phosphorus oxychloride to ethynodiol-17$\beta$-N-(2-chloroethyl) carbamate-3$\beta$-dihydrogen phosphate, or is phosphorylated with phenyl phosphorodichloridate to ethynodiol-17$\beta$-N-(2-chloroethyl) carbamate-3$\beta$phenyl hydrogen phosphate, or is phosphorylated with ethyl phosphorodichloridate to ethynodiol-17$\beta$-N-(2-chloroethyl) carbamate-3$\beta$-ethyl hydrogen phosphate, or is esterified with sulfuric acid to ethynodiol-17$\beta$-N-(2-chloroethyl) carbamate-3$\beta$-sodium sulphate, or is esterified with oenanthic acid to ethynodiol-17$\beta$-N-(2-chloroethyl) carbamate-3$\beta$-oenanthate, norethynodrel-17$\beta$-N-(2-chloroethyl) carbamate from norethynodrel, ethynodiol-17$\beta$-acetate-3$\beta$-N-(2-chloroethyl) carbamate from ethynodiol-17$\beta$-acetate, deoxycorticosterone-21-N-(2-chloroethyl) carbamate from deoxycorticosterone, estradiol-3-acetate-17$\beta$-N-cyclohexyl carbamate from 17$\beta$-estradiol-3-acetate, estriol-3,16$\alpha$-diacetate-17$\beta$-N-cyclohexyl carbamate from estriol-16$\alpha$,17$\beta$-diacetate, dihydrotestosterone-17$\beta$-N-cyclohexyl carbamate from dihydrotestosterone, testosterone-17$\beta$-N-cyclohexyl carbamate from testosterone, 19-nortestosterone-17$\beta$-N-cyclohexyl carbamate, mp. 173°C, from 19-nortestosterone, dehydroepiandrosterone-3$\beta$-carbamate, mp. 220°C, from dehydroepiandrosterone, dehydroepiandrosterone-3$\beta$-N-methyl carbamate, mp. 170°C, from dehydroepiandrosterone, dehydroepiandrosterone-3$\beta$-N-n-butyl carbamate from dehydroepiandrosterone, dehydroepiandrosterone-3β-N-cyclohexyl carbamate, mp. 208°C, from dehydroepiandrosterone, dehydroepiandrosterone-3β-N-phenyl carbamate, mp. 226°C, from dehydroepiandrosterone, dehydroepiandrosterone-3β-N-(p-chlorophenyl) carbamate from dehydroepiandrosterone, dehydroepiandrosterone-3β-N-(p-methoxyphenyl) carbamate from dehydroepiandrosterone, ethynodiol-17β-acetate-3β-N-cyclohexyl carbamate from ethynodiol-17β-acetate, cholesterol-3β-N-cyclohexyl carbamate from cholesterol, estra-1,3,5(10)-triene-3,17β-diol-16-one,17β-acetate-3-N-(2-chloroethyl) carbamate from estra-1,3,5(10)-triene-3,17β-diol-16-one,17β-acetate, estradiol-17β-acetate-3-N-(2-fluoroethyl) carbamate from estradiol-17β-acetate, estra-1,3,5(10),16-tetraen-3-ol, 3-N-(2-chloroethyl) carbamate from estra-1,3,5(10),16-tetraen-3-ol, 2α-methyl-dihydrotestosterone-17β-N-(2-chloroethyl) carbamate from 2α-methyldihydrotestosterone, etiocholanolone-3α-N-(2-fluoroethyl) carbamate from etiocholanolone, 4-methyltestosterone-17β-N-(2-chloroethyl) carbamate from 4-methyltestosterone, 6α-methyltestosterone-17β-N-(2-chloroethyl) carbamate from 6α-methyltestosterone, 17α-methyltestosterone-17β-N-(2-chloroethyl) carbamate from 17α-methyltestosterone, 9α-fluoro-11β-hydroxy-17α-methyltestosterone-17β-N-(2-chloroethyl) carbamate from 9α-fluoro-11β-hydroxy-17α-methyltestosterone, 7α,17α-dimethyltestosterone-17β-N-(2-chloroethyl) carbamate from 7α,17α-dimethyltestosterone, 17α-allyl-estr-4-en-17β-ol,17β-N-(2-chloroethyl) carbamate from 17α-allyl-estr-en-17β-ol, 17α-ethynyl-18-methyl-19-nortestosterone-17β-N-(2-chloroethyl) carbamate from 17α-ethynyl-18-methyl-19-nortestosterone, 6α-methyl-17α-hydroxyprogesterone,17α-N-(2-chloroethyl) carbamate from 6α-methyl-17α-hydroxyprogesterone, 6-chloro-6-dehydro-17α-hydroxyprogesterone,17α-N-(2-chloroethyl) carbamate from 6-chloro-6-dehydro-17α-hydroxyprogesterone, 6-chloropregna-4,6-diene-3β,17α-diol-20-one,3β-N-(2-chloroethyl) carbamate from 6-chloropregna-4,6-diene 3β,17α-diol-20-one, ethynodiol-17β-acetate-3β,N-(2-fluoroethyl) carbamate from ethynodiol-17β-acetate, pregnenolone-3β-N-(2-fluoroethyl) carbamate from pregnenolone, cholesterol-3β-N-(2-fluoroethyl) carbamate from cholesterol, ergosterol-3β-N-(2-chloroethyl) carbamate from ergosterol, estradiol-17β-acetate-3-N-methyl carbamate from estradiol-17β-acetate, estrone-3-N-(4-methylcyclohexyl) carbamate from estrone, estrone-3-N-(4-methylphenyl) carbamate from estrone, estradiol-3-methylether-17β-N-phenyl carbamate from estradiol-3-methylether, estradiol-3-methylether-17β-N-methyl carbamate from estradiol-3-methylether, estradiol-3-methylether-17β-carbamate from estradiol-3-methylether, dehydroepiandrosterone-3β-N-(4-methylcyclohexyl) carbamate from dehydroepiandrosterone, dehydroepiandrosterone-3β-N-(3,4-dimethylphenyl) carbamate from dehydroepiandrosterone, ethynodiol-17β-acetate-3β-N-methyl carbamate from ethynodiol-17β-acetate, ethynodiol-17β-acetate-3β-N-phenyl carbamate from ethynodiol-17β-acetate, corticosterone-21-acetate-11β-N-(2-chloroethyl) carbamate from corticosterone-21-acetate, prednisolone-11β-/N-(2-chloroethyl) carbamate/-17β,21-acetonide from prednisolone-17α,21-acetonide, prednisolone-11β-/N-(2-chloroethyl) carbamate/-17α,21-acetonide is then, by removal of the acetonide protecting group (according to Tanable-J, Am. Chem. Soc. 83 (1961), 756), converted to prednisolone-11β-N-(2-chloroethyl) carbamate, which then is phosphorylated (see Irmscher-Chem. Ind. 1961, 1035) to prednisolone-11β-/N-(2-chloroethyl) carbamate/-21-dihydrogen phosphate, or is phosphorylted to prednisolone-11β-/N-(2-chloroethyl) carbamate/-21-ethyl hydrogen phosphate, or is phosphorylated to prednisolone-11β-/N-(2-chloroethyl) carbamate/-21-phenyl hydrogen phosphate, or is esterified with pivalic acid to prednisolone-11β-/N-(2-chloroethyl) carbamate/-21-pivalate, or is esterified with succinic acid to prednisolone-11β-/N-(2-chloroethyl) carbamate/-21-hemisuccinate, or is esterified with acetic acid to predisolone-11β-/N-(2-chloroethyl) carbamate/-21-acetate, or is esterified with benzoic acid to prednisolone-11β-/N-(2-chloroethyl) carbamate/-21-benzoate, or is esterified with 3,3-dimethyl butyric acid to prednisolone-IIβ-/N-(2-chloroethyl) carbamate/-21-3,3-dimethyl butyrate, or is esterified with oenanthic acid to prednisolone-11β-/N-(2-chloroethyl) carbamate/-21-oenanthate ethynodiol-17β-acetate-3β-N-n-butyl carbamate from ethynodiol-17β-acetate, ethynodiol-17β-acetate-3β-N-(4-methylcyclohexyl) carbamate from ethynodiol-17β-acetate, ethynodiol-17β-acetate-3β-N-(4-chlorophenyl) carbamate from ethynodiol-17β-acetate, ethynodiol-17β-acetate-3β-carbamate from ethynodiol-17β-acetate, pregnenolone-3β-N-methyl carbamate from pregnenolone, pregnenolone-3β-N-cyclohexyl carbamate from pregnenolone, pregnenolone-3β-N-(2-chloroethyl) carbamate from pregnenolone, pregnenolone-3β-N-(4-methylcyclohexyl) carbamate from pregnonolone, pregnenolone-3β-N-phenyl carbamate from pregnenolone, cholesterol-3β-N-methyl carbamate from cholesterol, cholesterol-3β-N-phenyl carbamate from cholesterol,
cholesterol-3β-carbamate from cholesterol.

EXAMPLE 8

A solution of 4.25 g dehydroepiandrosterone-3β-cyclohexyl carbamate and 1.5 g of 2-chloroethylisocyanate in 50 ml dry methylene chloride is refluxed for 48 hrs. The solvent is evaporated and the residual pale yellow oil is dissolved in an ether-benzene mixture and chromatographed on neutral alumina to remove undesired impurities. The eluate is evaporated and the residual oil is dried in vacuo.

The obtained substance is dehydroepiandrosterone-3β-$N^2$-cyclohexyl-$N^4$-(2-chloroethyl) allophanate/ which has sufficient analytical purity with respect to Cl and N, and is pure in TLC.

The structure is confirmed by IR and NMR.

In substantially the same manner the following compounds are obtained as oils (having structures confirmed by IR, NMR and analysis for Cl and N, and being pure in TLC) from the corresponding substituted isocyanate and a steroid compound given below:

estradiol-17β-acetate-3-/$N^2$,$N^4$-bis (2-chloroethyl) allophanate/from estradiol-17β-acetate-3-N-(2-chloroethyl) carbamate, estradiol-3-acetate-17β-/$N^2$-cyclohexyl-$N^4$-(2-chloroethyl) allophanate/ from estradiol-3-acetate-17β-N-cyclohexyl carbamate, estriol-3,16α-diacetate-17β-/N-cyclohexyl-$N^4$-(2-chloroethyl) allophanate/ from estriol-3,16α-diacetate-17β-N-cyclohexyl carbamate, 17α-ethynylestradiol-17β-acetate-3-/$N^2$, $N^4$-bis (2-chloroethyl) allophanate/ from 17α-ethynylestradiol-17β-acetate-3-N-(2-chloroethyl) carbamate, dihydrotestosterone-17β-/$N^2$-cyclohexyl-$N^4$-(2-chloroethyl) allophanate/ from dihydrotestosterone-17β-N-cyclohexyl carbamate, testosterone-17β-/$N^2$-cyclohexyl-$N^4$-(2-chloroethyl) allophanate/ from testosterone-17β-N-cyclohexyl carbamate, 19-nortestosterone-17β-/$N^2$-cyclohexyl-$N^4$-(2-chloroethyl) allophanate/ from 19-nortestosterone-17β-N-cyclohexyl carbamate, dehydroepiandrosterone-3β-/$N^4$-(2-chloroethyl) allophanate/ from dehydroepiandrosterone-3β-carbamate, dehydroepiandrosterone-3β-$N^2$-methyl-$N^4$-(2-chloroethyl) allophanate/ from dehydroepiandrosterone-3β-N-methyl carbamate, dehydroepiandrosterone-3β-/$N^2$-methyl-$N^4$-(2-chloroethyl) allophanate/ above, is also reduced with sodium borohydride to androstenediol-3β-/$N^2$-methyl-$N^4$-(2-chloroethyl) allophanate/, which then is phosphorylated with phosphorus oxychloride to androstenediol-3β-/$N^2$-methyl-$N^4$-(2-chloroethyl) allophanate/-17β-dihydrogen phosphate, dehydroepiandrosterone-3β-/$N^2$-n-butyl-$N^4$-(2-chloroethyl) allophanate/ from dehydroepiandrosterone-3β-N-n-butyl carbamate, dehydroepiandrosterone-3β-/$N^2$,$N^4$-bis (2-chloroethyl) allophanate/ from dehydroepiandrosterone-3β-N-(2-chloroethyl) carbamate, dehydroepiandrosterone-3β-/$N^2$-phenyl-$N^4$-(2-chloroethyl) allophanate/ from dehydroepiandrosterone-3β-N-phenyl carbamate, dehydroepiandrosterone-3β-/$N^2$-( p -chlorophenyl)-$N^4$-(2-chloroethyl) allophanate/ from dehydroepiandrosterone-3β-N-( p-chlorophenyl) carbamate, dehydroepiandrosterone-3β-/$N^2$-(p-methoxyphenyl)-$N^4$-(2-chloroethyl) allophanate/ from dehydroepiandrosterone-3β-N-(p-methoxyphenyl) carbamate, 17α-ethynyl-19-nortestosterone-17β-/$N^2$,$N^4$-bis (2-chloroethyl) allophanate/ from 17α-ethynyl-19-nortestosterone-17β-N-(2-chloroethyl) carbamate, ethynodiol-17β-acetate-3β-/$N^2$-cyclohexyl-$N^4$-(2-chloroethyl) allophanate/ from ethynodiol-17β-acetate-3β-N-cyclohexyl carbamate, cholesterol-3β-/$N^2$-cyclohexyl-$N^4$-(2-chloroethyl) allophanate/ from cholesterol-3β-N-cyclohexyl carbamate, estradiol-17β-acetate-3-/$N^2$-methyl-$N^4$-(2-chloroethyl) allophanate/ from estradiol-17β-acetate-3-N-methyl carbamate, estrone-3-/$N^2$-(4-methylcyclohexyl)-$N^4$-(2-chloroethyl) allophanate/ from estrone-3-N-(4-methylcyclohexyl) carbamate, estrone-3-/$N^2$-(4-methylphenyl)-$N^4$-(2-chloroethyl) allophanate/ from estrone-3-N-(4-methylphenyl) carbamate, estradiol-3-methylether-17β-/$N^2$-phenyl-$N^4$-(2-chloroethyl) allophanate/ from estradiol-3-methylether-17β-N-phenyl carbamate, estradiol-3-methylether-17β-/$N^2$-methyl-$N^4$-(2-chloroethyl) allophanate/ from estradiol-3-methylether-17β-N-methyl carbamate, estradiol-3-methylether-17β-/$N^4$-(2-chloroethyl) allophanate/ from estradiol-3-methylether-17β-carbamate, dehydroepiandrosterone-3β-/$N^2$-(4-methylcyclohexyl)-$N^4$-(2-chloroethyl) allophanate/ from dehydroepiandrosterone-3β-N-(4-methylcyclohexyl) carbamate, dehydroepiandrosterone-3β-/$N^2$-(3,4-dimethylphenyl)-$N^4$-(2-chloroethyl) allophanate/ from dehydroepiandrosterone-3β-N-(3,4-dimethylphenyl) carbamate, ethynodiol-17β-acetate-3β-/$N^2$-methyl-$N^4$-(2-chloroethyl) allophanate/ from ethynodiol-17β-acetate-3β-N-methyl carbamate, ethynodiol-17β-acetate-3β-/$N^2$-phenyl-$N^4$-(2-chloroethyl) allophanate/ from ethynodiol-17β-acetate-3β-N-phenyl carbamate, ethynodiol-17β-acetate-3β-/$N^2$-n-butyl-$N^4$-(2-chloroethyl) allophanate/ from ethynodiol-17β-acetate-3β-N-n-butyl carbamate, ethynodiol-17β-acetate-3β-/$N^2$-(4-methylcyclohexyl)-$N^4$-(2-chloroethyl) allophanate/ from ethynodiol-17β-acetate-3β-N-(4-methylcyclohexyl) carbamate, ethynodiol-17β-acetate-3β-/$N^2$-phenyl-$N^4$-(2-chlorethyl) allophanate/ from ethynodiol-17β-acetate-3β-N-phenyl carbamate, ethynodiol-17β-acetate-3β-/$N^4$-(2-chloroethyl) allophanate/ from ethynodiol-17β-acetate-3β-carbamate, pregnenolone-3β-$N^2$-methyl-$N^4$-(2-chloroethyl) allophanate/ from pregnenolone-3β-N-methyl carbamate, pregnenolone-3β-/$N^2$-cyclohexyl-$N^4$-(2-chloroethyl) allophanate/ from pregnenolone-3β-N-cyclohexyl carbamate, pregnenolone-3β-/$N^2$,$N^4$-bis (2-chloroethyl) allophanate/ from pregnenolone-3β-N-(2-chloroethyl) carbamate, pregnenolone-$3\beta$-/$N^2$-(4-methylcyclohexyl)-$N^4$-(2-chloroethyl) allophanate/ from pregnenolone-$3\beta$-N-(4-methylcyclohexyl) carbamate, pregnenolone-$3\beta$-/$N^2$-phenyl-$N^4$-(2-chloroethyl) allophanate/ from pregnenolone-$3\beta$-N-phenyl carbamate, cholesterol-$3\beta$-/$N^2$-methyl-$N^4$-(2-chloroethyl) allophanate/ from cholesterol-$3\beta$-N-methyl carbamate, cholesterol-$3\beta$-/$N^2$-phenyl-$N^4$-(2-chloroethyl) allophanate/ from cholesterol-$3\beta$-N-phenyl carbamate, cholesterol-$3\beta$-/$N^2,N^4$-bis (2-chloroethyl) allophanate/ from cholesterol-$3\beta$-N-(2-chloroethyl) carbamate, cholesterol-$3\beta$-/$N^4$-(2-chloroethyl) allophanate/ from cholesterol$3\beta$-carbamate,

EXAMPLE 9

10.00 g prednisolone is dissolved in 100 ml dry pyridine. and 8.65 g $N^2,N^4$-bis (2-chloroethyl) allophanoyl chloride in 100 ml pyridine is added. The solution is left at room temperature for 2 days. The dark red reaction mixture is hydrolysed with about 10 g ice and then added dropwise to a mixture of 250 ml concentrated hydrochloric acid and 100 g ice with vigorous stirring. Under the addition the temperature is kept at 10°–15°C. The precipitated oil is extracted from the water phase with 3 × 200 ml ethyl acetate. The ethyl acetate solution is washed with 2 × 100 ml deionized water, dried with anhydrous sodium sulphate and the solvent is evaporated in vacuo.

The residual pale yellow oil is prednisolone-21-/$N^2,N^4$- bis (2-chloroethyl) allophanate/, which is pure in TLC. The structure and purity is confirmed by IR, NMR and analysis for Cl and N.

In substantially the same manner the following compound is obtained as an oil (having structure confirmed by IR, NMR and analysis for Cl and N from the corresponding $N^2,N^4$-substituted allophanoyl chloride and a steroid compound given below: prednisolone-21-/$N^2$-cyclohexyl-$N^4$-(2-chloroethyl) allophanate/ from prednisolone,

EXAMPLE 10

3.94 g androstanediol-$3\alpha,17\beta$-bis /N-(2-chloroethyl)carbamate/ is suspended in 40 ml of concentrated nitric acid (sp. gr. 1.39). To the slurry is added 5 ml of fuming nitric acid (sp.gr. 1.50) whereupon the mixture is heated with stirring until the substance is completely dissolved. The heating is maintained for 2 hrs. at max. 50°C. The solution is then poured out on 200 g ice and the precipitate is filtered off and washed with water.

The product, which is the androstanediol-$3\alpha,17\beta$-bis /N-(2-chloroethyl)-N-nitro carbamate/, is suspended in 200 ml water and the suspension is violently agitated while 3 g ammonium chloride is added. When the ammonium chloride is dissolved 6 g zinc dust is added in small portions at such a rate that the temperature of the solution is maintained below 50°C.

When the reduction is completed the substance is filtered off and washed with water.

The product is the androstanediol-$3\alpha,17\beta$-bis /N-(2-chloroethyl)-N-nitroso carbamate/ which after recrystallisation from acetone-water has a melting point of 83°C and is pure in TLC.

In substantially the same manner the following compounds are obtained as oils, unless otherwise stated, (having structures confirmed by IR, NMR and analysis for Cl and N) from the corresponding starting materials (prepared according to Example 6, 7 or 8).

androstenediol-$3\beta,17\beta$-bis-/N-(2-chloroethyl)-N-nitroso carbamate/, mp. 120°C, from androstenediol-$3\beta$, $17\beta$-bis/N-(2-chloroethyl) carbamate/ via androstenediol-$3\beta,17\beta$-bis-/N-(2-chloroethyl)-N-nitro carbamate/, androstenediol-$3\beta$-/N-(2-chloroethyl)-N-nitroso carbamate/-$17\beta$-dihydrogen phosphate from androstenediol-$3\beta$-/N-(2-chloroethyl) carbamate/-$17\beta$-dihydrogen phosphate via androstenediol-$3\beta$-/N-(2-chloroethyl)-N-nitro carbamate/-$17\beta$-dihydrogen phosphate, androstenediol-$3\beta$-/$N^2$-methyl-$N^4$-(2-chloroethyl)-$N^4$-nitroso allophanate/-$17\beta$-dihydrogen phosphate from androstenediol-$3\beta$-/$N^2$-methyl-$N^4$-(2-chloroethyl) allophanate/-$17\beta$-dihydrogen phosphate via androstenediol-$3\beta$-/$N^2$-methyl-$N^4$-(2-chloroethyl)-$N^4$-nitro allophanate/-$17\beta$-dihydrogen phosphate, androstenediol-$17\beta$-hemisuccinate-$3\beta$-N-(2-chloroethyl)-N-nitroso carbamate from androstenediol-$17\beta$-hemisuccinate-$3\beta$-N-(2-chloroethyl) carbamate via androstenediol-$17\beta$-hemisuccinate-$3\beta$-N-(2-chloroethyl)-N-nitro carbamate, ethynodiol-$17\beta$-acetate-$3\beta$-/$N^2$-cyclohexyl-$N^4$-(2-chloroethyl)-$N^4$-nitroso allophanate/ from ethynodiol-$17\beta$-acetate-$3\beta$-/$N^2$-cyclohexyl-$N^4$-(2-chloroethyl) allophanate via ethynodiol-$17\beta$-acetate-$3\beta$-/$N^2$-cyclohexyl-$N^4$-(2-chloroethyl)-$N^4$-nitro allophanate, ethynodiol-$17\beta$-N-(2-chloroethyl)-N-nitroso carbamate-$3\beta$-ethylhydrogen phosphate from ethynodiol-$17\beta$-N-(2-chloroethyl) carbamate-$3\beta$-ethyl hydrogen phosphate via ethynodiol-$17\beta$-N-(2-chloroethyl)-N-nitro carbamate-$3\beta$-ethyl hydrogen phosphate, cholesterol-$3\beta$-N-(2-chloroethyl)-N-nitroso carbamate, mp. 127°C, from cholesterol-$3\beta$-N-(2-chloroethyl) carbamate via cholesterol-$3\beta$-N-(2-chloroethyl)-N-nitro carbamate, cholesterol-$3\beta$-N-(2-fluoroethyl)-N-nitroso carbamate from cholesterol-$3\beta$-N-(2-fluoroethyl) carbamate via cholesterol-$3\beta$-N-(2fluoroethyl)-N-nitro carbamate, cholesterol-$3\beta$-/$N^2,N^4$-bis (2-chloroethyl)-$N^4$-nitroso allophanate/ from cholesterol-$3\beta$-/$N^2,N^4$-bis (2-chloroethyl) allophanate/ via cholesterol-$3\beta$-/$N^2,N^4$-bis (2-chloroethyl)-$N^4$-nitro allophanate/,

EXAMPLE 11

This example illustrates the effect of compounds of the present invention in inhibiting the growth of several tumours. From the results obtained it is also obvious that the compounds of the present invention have a very low toxicity.

The high activity against tumours is further illustrated in these experiments by comparisons with known antitumour agents used in the therapy. The therapeutic indexes (T.I.), i.e. the ratios LD50/ED50, are in all comparisons much more favourable with the compounds of the present invention.

LD50 is the dose that caused a 50 percent lethality of the animals, ED50 is the dose that caused a 50 percent reduction of tumour size.

Also other types of evaluations show the superior effects obtained with the new compounds.

The experimental design and the interpretation of the results have been in accordance with the standards set by the CCNSC (Cancer Chemotherapy Reports, January 1959 and December 1962), and by the DR&D (Cancer Chemotherapy Reports, September 1972, Vol. 3, No. 2).

The way of administration is by the intraperitoneal route (i.p.) in each case.

Some of the results obtained are given in Tables 1-4 below.

This example shows that the new compounds are useful to prevent the growth of tumours and therefore can be employed in treating a living animal body suffering from disorders responsive to treatment with anti-cancer agents and with immuno-suppressive agents.

TABLE 1

Hepatoma AH 130
Experimental animals: SPF Wistar rats.
Tumour implant: $5 \times 10^6$ tumour cells i.p.
Therapy: One injection i.p. on the day following implantation.
Termination: The animals are killed on the 8th day.
Evaluation: Weights of tumours of test animals compared with those of control animals.

estradiol-3-N-(2-chloroethyl)-N-nitroso carbamate-17β-sodium sulphate,
estradiol-17β-N-(2-chloroethyl)-N-nitroso carbamate-3-cyclopentyl ether,
estradiol-3,17β-bis/N-(2-chloroethyl)-N-nitroso carbamate/,
estradiol-17β-acetate-3-/$N^2,N^4$-bis (2-chloroethyl)-$N$-$^4$-nitroso allophanate/,
estradiol-3-acetate-17β-/$N^2$-cyclohexyl-$N^4$-(2-chloroethyl)-$N^4$-nitroso allophanate/,
estriol-16α,17β-diacetate-3-diacetate-3-N-(2-chloroethyl)-N-nitroso carbamate,
estriol-3-N-(2-chloroethyl)-N-nitroso carbamate-16α,17β-bis-hemisuccinate,
estriol-3-acetate-16α,17β-bis-N-(2-chloroethyl)-N-nitroso carbamate/,
estriol-3,16α-diacetate-17β-/$N^2$-cyclohexyl-$N^4$-(2-chloroethyl)-$N^4$-nitroso allophanate/,
17α-ethynylestradiol-17β-acetate-3-N-(2-chloroethyl)-N-nitroso carbamate,
17α-ethynylestradiol-3-acetate-17β-N-(2-chloroethyl)-N-nitroso carbamate,
17α-ethynylestradiol-17β-acetate-3-/$N^2,N^4$-bis(2-

Results:

| Compound | LD50 mg/kg | ED50 mg/kg | T.I. (LD50/ED50) |
|---|---|---|---|
| Estrone-3-N-(2-chloroethyl)-N-nitroso carbamate | >1×1.000 | 1×0.5 | >2.000 |
| 17β-Estradiol-3-N-(2-chloroethyl)-N-nitroso carbamate | >1×1.000 | <1×0.25 | >4.000 |
| Estradiol-17β-acetate-3-N-(2-chloroethyl)-N-nitroso carbamate | >1×1.000 | <1×0.25 | >4.000 |
| Estradiol-17β-N-(2-chloroethyl)-N-nitroso carbamate-3-methyl ether | >1×1.000 | 1×0.5 | >2.000 |
| Estradiol-3-acetate-17β-N-(2-chloroethyl)-N-nitroso carbamate | >1×1.000 | 1×96 | >10 |
| Estradiol-3-benzoate-17β-N-(2-chloroethyl)-N-nitroso carbamate | >1×1.000 | <1×63 | >16 |
| Androsterone-3α-N-(2-chloroethyl)-N-nitroso carbamate | >1×1.000 | 1×10 | >100 |
| Epiandrosterone-3β-N-(2-chloroethyl)-N-nitroso carbamate | >1×1.000 | 1×0.2 | >5.000 |
| Dihydrotestosterone-17β-N-(2-chloroethyl)-N-nitroso carbamate | >1×1.000 | 1×1 | >1.000 |
| Testosterone-17β-N-(2-chloroethyl)-N-nitroso carbamate | >1×1.000 | 1×8 | >100 |
| 19-Nortestosterone-17β-N-(2-chloroethyl)-N-nitroso carbamate | 1×150 | 1×0.5 | 300 |
| Androstenediol-17β-acetate-3β-N-(2-chloroethyl)-N-nitroso carbamate | >1×250 | 1×0.25 | >1.000 |
| Androstenediol-3β-acetate-17β-N-(2-chloroethyl)-N-nitroso carbamate | >1×250 | 1×0.25 | >1.000 |
| Androstenediol-3β,17β-bis/N-(2-chorethyl)-N-nitroso carbamate | >1×250 | 1×0.25 | >1.000 |
| Androstanediol-3α,17β-bis/N-(2-chloroethyl)-N-nitroso carbamate/ | >1×1.000 | 1×1 | >1.000 |
| Dehydroepiandrosterone-3β -N-(2-chloroethyl)-N-nitroso carbamate | >1×1.000 | 1×0.4 | >2.500 |
| Dehydroepiandrosterone-3β-N(2-bromoethyl)-N-nitroso carbamate | >1×1.000 | 1×70 | >14 |
| Dehydroepiandrosterone-3β-N-(2-chloropropyl)-N-nitroso carbamate | >1×1.000 | 1×100 | >10 |
| Dehydroepiandrosterone-3β-N-(3-chloropropyl)-N-nitroso carbamate | >1×1.000 | 1×375 | >2.7 |
| Pregnenolone-3β-N-(2-chloroethyl)-N-nitroso carbamate | >1×1.000 | 1×1.9 | >526 |
| Cholesterol-3β-N-(2-chloroethyl)-N-nitroso carbamate | >1×1.000 | 1×200 | >5 |

The following additional compounds exhibit anti-tumor activity in the foregoing test:
estradiol-3-N-(2-chloroethyl)-N-nitroso carbamate-17β-(p-propoxyphenyl-propionate),
estradiol-3-N-(2-chloroethyl)-N-nitroso carbamate-17β-dihydrogen phosphate, chloroethyl)-$N^4$-nitroso allophanate/,
dihydrotestosteron-17β-/$N^2$-cyclohexyl-$N^4$-(2-chloroethyl)-$N^4$-nitroso allophanate/,
testosterone-17β-/$N^2$-cyclohexyl-$N^4$-(2-chloroethyl)-$N^4$-nitroso allophanate/, 19-nortestosterone-17β-/N²-cyclohexyl-N⁴-(2-chloroethyl)-N⁴-nitroso allophanate/, 17α-ethyl-19-nortestosterone-17β-N-(2-chloroethyl)-N-nitroso carbamate, androstanediol-3α-N-(2-chloroethyl)-N-nitroso carbamate, androstanediol-3α-N-(2-chloroethyl)-N-nitroso carbamate-17β-oenanthate, androstanediol-3α-N-(2-chloroethyl)-N-nitroso carbamate-17β-dihydrogen phosphate, etiocholanolone-3α-N-(2-chloroethyl)-N-nitroso carbamate, dehydroepiandrosterone-3β-N-(2-fluoroethyl)-N-nitroso carbamate, dehydroepiandrosterone-3β-/N⁴-(2-chloroethyl)-N⁴-nitroso allophanate/, dehydroepiandrosterone-3β-/N²-methyl-N⁴-(2-chloroethyl)-N⁴-nitroso allophanate/, dehydroepiandrosterone-3β-/N²-n-butyl-N⁴-(2-chloroethyl)-N⁴-nitroso allophanate/, dehydroepiandrosterone-3β-/N²,N⁴-bis (2-chloroethyl)-N⁴-nitroso allophanate/, dehydroepiandrosterone-3β-/N²-cyclohexyl-N⁴-(2-chloroethyl)-N⁴-nitroso allophanate/, dehydroepiandrosterone-3β-/N²-phenyl-N⁴-(2-chloroethyl)-N⁴-nitroso allophanate/, dehydroepiandrosterone-3β-/N²-(p-chlorophenyl)-N⁴-(2-chloroethyl)-⁴-nitroso allophanate/, dehydroepiandrosterone-3β-/N²-(p-methoxyphenyl)-N⁴-(2-chloroethyl)-N⁴-nitroso allophanate/, 17α-hydroxy-progesterone,17α-N-(2-chloroethyl)-N-nitroso carbamate, 17α-ethynyl-19-nortestosterone-17β-N-(2-chloroethyl)-N-nitroso carbamate, 17α-ethynyl-19-nortestosterone-17β-/N²,N⁴-bis (2-chloroethyl)-N⁴-nitroso allophanate/, norethyndrel-17β-N-(2-chloroethyl)-N-nitroso carbamate, ethynodiol-17β-acetate-3β-N-(2-chloroethyl)-N-nitroso carbamate, ethynodiol-17β-acetate-3β-/N²-cyclohexyl-N⁴-(2-chloroethyl)-N⁴-nitroso allophanate/, deoxycorticosterone-21-N-(2-chloroethyl)-N-nitroso carbamate hydrocortisone-21-N-(2-chloroethyl)-N-nitroso carbamate, prednisone-21-N-(2-chloroethyl)-N-nitroso carbamate, prednisolone-21-N-(2-chloroethyl)-N-nitroso carbamate, prednisolone-21-/N²,N⁴-bis (2-chloroethyl)-N⁴-nitroso allophanate/, cholesterol-3β-/N²-cyclohexyl-N-⁴-(2-chloroethyl)-N⁴-nitroso allophanate/, estra-1,3,5(10)-triene-3,17β-diol-16-one,17β-acetate-3-N-(2-chloroethyl)-N-nitroso carbamate, estradiol-17β-acetate-3-N-(2-fluoroethyl)-N-nitroso carbamate, estradiol-17β-phenyl hydrogen phosphate-3-N-(2-chloroethyl)-N-nitroso carbamate, estradiol-17β-ethyl hydrogen phosphate-3-N-(2-chloroethyl)-N-nitroso carbamate, estradiol-3-N-(2-chloroethyl)-N-nitroso carbamate-17β-valerate, estradiol-17β-acetate-3-/N²-methyl-N⁴-(2-chloroethyl)-N⁴-nitroso allophanate/, estrone-3-/N²-(4-methylcyclohexyl)-N⁴-(2-chloroethyl)-N⁴-nitroso allophanate/, corticosterone-21-acetate-11β-N-(2-chloroethyl)-N-nitroso carbamate prednisolone-11β-N-(2-chloroethyl)-N-nitroso carbamate, estrone-3-/N²-(4-methylphenyl)-N⁴-(2-chloroethyl)-N⁴-nitroso allophanate/, estradiol-3-methylether-17β-/N²-phenyl-N⁴-(2-chloroethyl)-N⁴-nitroso allophanate/, estradiol-3-methylether-17β-/N²-methyl-N⁴-(2-chloroethyl)-N⁴-nitroso allophanate, estradiol-3-methylether-17β-/N⁴-(2-chloroethyl)-N⁴-nitroso allophanate/, estra-1,3,5(10),16-tetraen-3-ol,3-N-(2-chloroethyl)-N-nitroso carbamate, 2α-methyl-dihydrotestosterone-17β-N-(2-chloroethyl)-N-nitroso carbamate, etiocholanolone-3α-N-(2-fluoroethyl)-N-nitroso carbamate, 4-methyl-testosterone-17β-N-(2-chloroethyl)-N-nitroso carbamate, 6α-methyltestosterone-17β-N-(2-chloroethyl)-N-nitroso carbamate, 17α-methyltestosterone-17β-N-(2-chloroethyl)-N-nitroso carbamate, 9α-fluoro-11β-hydroxy-17α-methyltestosterone-17β-N-(2-chloroethyl)-N-nitroso carbamate, 7α,17α-dimethyltestosterone-17β-N-(2-chloroethyl)-N-nitroso carbamate, androstenediol-3β-/N-(2-chloroethyl)-N-nitroso carbamate/-17β-phenyl hydrogen phosphate, androstenediol-3β-/N-(2-chloroethyl)-N-nitroso carbamate/-17β-dihydrogen phosphate, androstenediol-3β-/N-(2-chloroethyl)-N-nitroso carbamate/-17β-ethyl hydrogen phosphate, androstenediol-3β-/N-(2-chloroethyl)-N-nitroso carbamate/-17β-sodium sulphate, androstenediol-3β-/N²-methyl-N⁴-(2-chloroethyl)-N⁴nitroso allophanate/-17β-dihydrogen phosphate, androstenediol-17β-hemisuccinate-3β-N-(2-chloroethyl-N-nitroso carbamate, androstenediol-17β-p-hexoxyphenylpropionate-3β-N-(2-chloroethyl)-N-nitroso carbamate, androstenediol-17β-methylether-3β-N-(2-chloroethyl)-N-nitroso carbamate, androstenediol-17β-benzoate-3β-N-(2-chloroethyl)-N-nitroso carbamate, dehydroepiandrosterone-3β-/N²-(4-methylcyclohexyl)-N⁴-(2-chloroethyl)-N⁴-nitroso allophanate/, dehydroepiandrosterone-3β-/N²-(3,4-dimethylphenyl)-N⁴-(2-chloroethyl)-N⁴-nitroso allophanate/, 17α-allyl-estr-4-en-17β-ol,17β-N-(2-chloroethyl)-N-nitroso carbamate, 17α-ethynyl-18methyl-19-nortestosterone-17β-N-(2-chloroethyl)-N-nitroso carbamate, 6α-methyl-17α-hydroxy-progesterone,17α-N-(2-chloroethyl)-N-nitroso carbamate, 6-chloro-6-dehydro-17α-hydroxyprogesterone,17α-N-(2-chloroethyl)-N-nitroso carbamate, 6-chloro-pregna-4,6-diene-3β,17α-diol-20-one,3β-N-(2-chloroethyl)-N-nitroso carbamate, ethynodiol-17β-acetate-3β-N-(2-fluoroethyl)-N-nitroso carbamate, ethynodiol-17β-acetate-3β-/N²-methyl-N⁴-(2-chloroethyl)-N⁴-nitroso carbamate/, ethynodiol-17β-acetate-3β-/N²-phenyl-N⁴-(2-chloroethyl)-N-nitroso allophanate/, ethynodiol-17β-acetate-3β-/N²-n-butyl-N⁴-(2-chloroethyl)-N⁴-nitroso allophanate/, prednisolone-11β-/N-(2-chloroethyl)-N-nitroso carbamate/-21-dihydrogen phosphate,
ethynodiol-17β-N-(2-chloroethyl)-N-nitroso carbamate,
ethynodiol-17β-N-(2-chloroethyl)-N-nitroso carbamate-3β-dihydrogen phosphate,
ethynodiol-17β-N-(2-chloroethyl)-N-nitroso carbamate-3β-phenylhydrogen phosphate,
ethynodiol-17β-N-(2-chloroethyl)-N-nitroso carbamate-3β-ethyl hydrogen phosphate,
ethynodiol-17β-N-(2-chloroethyl)-N-nitroso carbamate-3β-sodium sulphate,
ethynodiol-17β-N-(2-chloroethyl)-N-nitroso carbamate-3β-oenanthate,
ethynodiol-17β-acetate-3β-/$N^2$-(4-methylcyclohexyl)-$N^4$-(2-chloroethyl)-$N^4$-nitroso allophanate/,
ethynodiol-17β-acetate-3β-/$N^2$-phenyl-$N^4$-(2-chloroethyl)-$N^4$-nitroso allophanate/,
ethynodiol-17β-acetate-3β-/$N^4$-(2-chloroethyl)-$N^4$-nitroso allophanate/,
pregnenolone-3β-N-(2-fluoroethyl)-N-nitroso carbamate,
pregnenolone-3β-/$N^2$-methyl-$N^4$-(2-chloroethyl)-$N^4$-nitroso allophanate/,
pregnenolone-3β-/$N^2$-cyclohexyl-$N^4$-(2-chloroethyl)-$N^4$-nitroso allophanate/,
pregnenolone-3β-/$N^2$,$N^4$-bis (2-chloroethyl)-$N^4$-nitroso allophanate/,
pregnenolone-3β-/$N^2$-(4-methylcyclohexyl)-$N^4$-(2-chloroethyl)-$N^4$-nitroso allophanate/,
pregnenolone-3β-/$N^2$-phenyl-$N^4$-(2-chloroethyl)-$N^4$-nitroso allophanate/,
prednisolone-21-/$N^2$-cyclohexyl-$N^4$-(2-chloroethyl)-N-nitroso allophanate/,
prednisolone-11β-/N-(2-chloroethyl)-N-nitroso carbamate/-21-pivalate,
cholesterol-3β-N-(2-fluoroethyl)-N-nitroso carbamate,
cholesterol-3β-/$N^2$-methyl-$N^4$-(2-chloroethyl)-$N^4$-nitroso allophanate/,
cholesterol-3β-/$N^2$-phenyl-N-4-(2-chloroethyl)-$N^4$-nitroso allophanate/,
cholesterol-3β-/$N^2$,$N^4$-bis (2-chloroethyl)-$N^4$-nitroso allophanate/,
ergosterol-3β-N-(2-chloroethyl)-N-nitroso carbamate,
cholesterol-3β-/$N^4$-(2-chloroethyl)-$N^4$-nitroso allophanate/, Contrary to the above given results the following derivatives of dehydroepiandrosterone are found to be inactive in the doses 1 × 250, 1 × 500 and 1 × 1000 mg/kg respectively.

dehydroepiandrosterone-3β-N-(2-chloroethyl)-carbamate dehydroepiandrosterone-3β-N-ethyl-N-nitroso carbamate, and dehydroepiandrosterone-3β-N-(2-chloroethyl)-N-methyl carbamate.

The lack of activity with these three compounds shows that both the N-nitroso group and the halogen atom in $R^1$ (as defined in the general formula (I) above) are essential in the new compounds to make them active against tumours.

TABLE 2

Walker carcinosarcoma 256

Experimental animals: Sprague Dawley rats.

Tumour implant: Tumour pieces with 2–4 mm diameter, subcutaneously.

Therapy: Daily injections i.p. for 5 days starting on the day following implantation.

Termination: The animals are killed on the 9th day.

Evaluation: Weights of tumours of test animals are compared with those of control animals. The differences, in per cent of weights of tumours of control animals, give per cent tumour inhibition.

The lethality is given as the number of animals which died in the experiment/the number of animals used in the experiments.

Results:

| Compound | Dose mg/kg | Lethality | Tumour inhibition % |
|---|---|---|---|
| Estrone-3-N-(2-chloroethyl)-N-nitroso carbamate | 5×125 | 0/8 | 75 |
| 17β-Estradiol-3-N-(2-chloroethyl)-N-nitroso carbamate | 5×31 | 0/8 | 86 |
| Estradiol-17β-acetate-3-N-(2-chloroethyl)-N-nitroso carbamate | 5×125 | 1/8 | 69 |
| Estradiol-17β-N-(2-chloroethyl)-N-nitroso carbamate-3-methyl ether | 5×250 | 0/8 | 66 |
| Estradiol-3-acetate-17β-N-(2-chloroethyl)-N-nitroso carbamate | 5×250 | 1/8 | 74 |
| Estradiol-3-benzoate-17β-N-(2-chloroethyl)-N-nitroso carbamate | 5×125 | 0/8 | 73 |
| Androsterone-3α-N-(2-chloroethyl)-N-nitroso carbamate | 5×250 | 0/8 | 82 |
| Epiandrosterone-3β-N-(2-chloroethyl)-N-nitroso carbamate | 5×125 | 0/8 | 47 |
| Dihydrotestosterone-17β-N-(2-chloroethyl)-N-nitroso carbamate | 5×250 | 0/8 | 51 |
| Testosterone-17β-N-(2-chloroethyl)-N-nitroso carbamate | 5×250 | 0/8 | 64 |
| 19-Nortestosterone-17β-N-(2-chloroethyl)-N-nitroso carbamate | 5×63 | 1/8 | 65 |
| Androstenediol-17β-acetate-3β-N-(2-chloroethyl)-N-nitroso carbamate | 5×125 | 0/8 | 59 |
| Androstenediol-3β-acetate-17β-/N-(2-chloroethyl)-N-nitroso carbamate | 5×125 | 0/8 | 41 |
| Androstanediol-3α,17β-bis/N-(2-chloroethyl)-N-nitroso carbamate/ | 5×250 | 1/8 | 75 |
| Dehydroepiandrosterone-3β-N-(2-chloroethyl)-N-nitroso carbamate | 5×250 | 0/16 | 66 |
| Dehydroepiandrosterone-3β-N-(2-bromoethyl)-N-nitroso carbamate | 5×250 | 0/8 | 61 |
| Dehydroepiandrosterone-3β-N-(3-chloropropyl)-N-nitroso carbamate | 5×500 | 0/8 | 24 |

-continued

Results:

| Compound | Dose mg/kg | Lethality | Tumour inhibition % |
|---|---|---|---|
| Dehydroepiandrosterone-3β-N-(3-bromopropyl)-N-nitroso carbamate | 5×125 | 0/8 | 39 |
| Pregnenolone-3β-N-(2-chloroethyl)-N-nitroso carbamate | 5×500 | 0/8 | 55 |
| Cholesterol-3β-N-(2-chloroethyl)-N-nitroso carbamate | 5×500 | 0/8 | 39 |
| Dehydroepiandrosterone-3β-N-ethyl-N-nitroso carbamate | 5×500 | 1/8 | 0 |
| Dehydroepiandrosterone-3β-N-(2-chloroethyl)-N-methyl-carbamate | 5×500 | 0/8 | <10 |

As seen from the lack of activity of the last two compounds as compared with the high activity of the third one in the table above, both the N-nitroso-group and the halogen atom in $R^1$ (as defined in the general formula (I) above) are essential in the new compounds to make them active against tumours.

TABLE 3

Ehrlich ascites tumour, ELD hyperdiploid (46 chromosomes)
Experimental animals: SPF NMRI mice.
Tumour implant: $2 \times 10^6$ tumour cells i.p.
Therapy: One injection i.p. on the day following implantation.
Termination: The animals are killed on the 8th day.
Evaluation: Weights of tumours of test animals compared with those of control animals.

Results:

| Compound | LD50 mg/kg | ED50 mg/kg | T.I. (LD50/ED50) |
|---|---|---|---|
| Dehydroepiandrosterone-3β-N-(2-chloroethyl)-N-nitroso carbamate | >1×1.000 | 1×98 | >102 |
| Chlorambucil | 1×33 | 1×9 | 3.7 |
| Cyclofosfamid | 1×470 | 1×62 | 7.6 |
| Triethylene-thiophosphoramide | 1×22 | 1×15 | 1.5 |
| Triethylene-melamine | 1×2.7 | 1×1.03 | 2.6 |
| Busulfan | 1×71 | 1×55 | 1.3 |

The following additional compounds exhibit anti-tumor activity in the foregoing test:
estrone-3-N-(2-chloroethyl)-N-nitroso carbamate,
estradiol-17β-acetate-3-N-(2-chloroethyl)-N-nitroso carbamate,
estradiol-3-methylether-17β-N-(2-chloroethyl)-N-nitroso carbamate,
estradiol-3-acetate-17β-N-(2-chloroethyl)-N-nitroso carbamate,
estradiol-3-benzoate-17β-N-(2-chlorethyl)-N-nitroso carbamate,
androsterone-3α-N-(2-chlorethyl)-N-nitroso carbamate,
epiandrosterone-3β-N-(2-chlorethyl)-N-nitroso carbamate,
dihydrotestosterone-17β-N-(2-chloroethyl)-N-nitroso carbamate,
testosterone-17β-N-(2-chlorethyl)-N-nitroso carbamate,
19-nortestosterone-17β-N-(2-chloroethyl)-N-nitroso carbamate,
androstenediol-17β-acetate-3β-N-(2-chlorethyl)-N-nitroso carbamate,
androstenediol-3β-acetate-17β-N-(2-chloroethyl)-N-nitroso carbamate,
androstenediol-3β,17β-bis-/N-(2-chloroethyl)-N-nitroso carbamate/,
androstanediol-3α,17β-bis/N-(2-chloroethyl)-N-nitroso carbamate/,
dehydroepiandrosterone-3β-N-(2-bromoethyl)-N-nitroso carbamate,
dehydroepiandrosterone-3β-N-(2-chloropropyl)-N-nitroso carbamate,
dehydroepiandrosterone-3β-N-(3-chloropropyl)-N-nitroso carbamate,
dehydroepiandrosterone-3β-N-(3-bromopropyl)-N-nitroso carbamate,
pregnenolone-3β-N-(2-chloroethyl)-N-nitroso carbamate,
cholesterol-3β-N-(2-chlorethyl)-N-nitroso carbamate,
17β-estradiol-3-N-(2-chloroethyl)-N-nitroso carbamate,
estradiol-3-N-(2-chloroethyl)-N-nitroso carbamate-17β-(p-propoxyphenyl-propionate),
estradiol-3-N-(2-chloroethyl)-N-nitroso carbamate-17β-dihydrogen phosphate,
estradiol-3-N-(2-chloroethyl)-N-nitroso carbamate-17β-sodium sulphate,
estradiol-17β-N-(2-chloroethyl)-N-nitroso carbamate-3-cyclopentyl ether,
estradiol-3,17β-bis/N-(2-chloroethyl)-N-nitroso carbamate/,
estradiol-17β-acetate-3/$N^2$,$N^4$-bis (2-chloroethyl)-$N^4$nitroso allophanate/,
estradiol-3-acetate-17β-/$N^2$-cyclohexyl-$N^4$-(2-chloroethyl)-$N^4$-nitroso allophanate/,
estriol-16α,17β-diacetate-3-N-(2-chloroethyl)-N-nitroso carbamate,
estriol-3-N-(2-chloroethyl)-N-nitroso carbamate-16α,17β-bishemisuccinate,
estriol-3-acetate-16α,17β-bis-/N-(2-chloroethyl)-N-nitroso carbamate/ estriol-3,16α-diacetate-17β-/N²-cyclohexyl-N⁴-(2-chloroethyl)-N⁴-nitroso allophanate/,
17α-ethynylestradiol-16β-acetate-3-N-(2-chloroethyl)-N-nitroso carbamate,
17α-ethynylestradiol-3-acetate-17β-N-(2-chloroethyl)-N-nitroso carbamate,
17α-ethynylestradiol-17β-acetate-3-/N²,N⁴-bis(2-chloroethyl)-N⁴-nitroso allophanate/,
dihydrotestosteron-17β-/N²-cyclohexyl-N⁴-(2-chloroethyl)-N⁴-nitroso allophanate/,
testosterone-17β/N²-cyclohexyl-N⁴-(2-chloroethyl)-N⁴-nitroso allophanate/,
19-nortestosterone-17β-/N²-cyclohexyl-N⁴-(2-chloroethyl)-N⁴-nitroso allophanate/,
17α-ethyl-19-nortestosterone-17β-N-(2-chloroethyl)-N-nitroso carbamate,
androstanediol-3α-N-(2-chloroethyl)-N-nitroso carbamate,
androstanediol-3α-N-(2-chloroethyl)-N-nitroso carbamate-17β-oenanthate,
androstanediol-3α-N-(2-chloroethyl)-N-nitroso carbamate-17β-dihydrogen phosphate,
etiocholanolone-3α-N-(2-chloroethyl)-N-nitroso carbamate,
dehydroepiandrosterone-3β-N-(2-fluoroethyl)-N-nitroso carbamate,
dehydroepiandrosterone-3β-/N⁴-(2-chloroethyl)-N⁴-nitroso allophanate/,
dehydroepiandrosterone-3β-/N²-methyl-N⁴-(2-chloroethyl)-N⁴-nitroso allophanate/,
dehydroepiandrosterone-3β-/N²-n-butyl-N⁴-(2-chloroethyl)-N⁴-nitroso allophanate/,
dehydroepiandrosterone-3β-/N²,N⁴-bis (2-chloroethyl)-N⁴-nitroso allophanate/,
dehydroepiandrosterone-3β-/N²-cyclohexyl-N⁴-(2-chloroethyl)-N⁴-nitroso allophanate/,
dehydroepiandrosterone-3β-/N²-phenyl-N⁴-(2-chloroethyl)-N⁴-nitroso allophanate/,
dehydroepiandrosterone-3β-/N²-(p-chlorophenyl)-N⁴-(2-chloroethyl)-N⁴-nitroso allophanate/,
dehydroepiandrosterone-3β-/N²-(p-methoxyphenyl)-N⁴-(2-chloroethyl)-N⁴-nitroso allophanate/,
17α-hydroxy-progesterone,17α-N-(2-chloroethyl)-N-nitroso carbamate,
17α-ethynyl-19-nortestosterone-17β-N-(2-chloroethyl)-N-nitroso carbamate,
17α-ethynyl-19-nortestosterone-17β-/N²,N⁴-bis (2-chloroethyl)-N⁴-nitroso allophanate/,
norethynodrel-17β-N-(2-chloroethyl)-N-nitroso carbamate
ethynodiol-17β-acetate-3β-N-(2-chloroethyl)-N-nitroso carbamate,
ethynodiol-17β-acetate-3β-/N²-cyclohexyl-N⁴-(2-chloroethyl)-N⁴-nitroso allophanate/,
deoxycorticosterone-21-N-(2-chloroethyl)-N-nitroso carbamate
hydrocortisone-21-N-(2-chloroethyl)-N-nitroso carbamate,
prednisone-21-N-(2-chloroethyl)-N-nitroso carbamate,
prednisolone-21-N-(2-chloroethyl)-N-nitroso carbamate,
prednisolone-21-/N²,N⁴-bis (2-chloroethyl)-N⁴-nitroso allophanate/,
cholesterol-3β-/N²-cyclohexyl-N⁴-(2-chloroethyl)-N⁴-nitroso allophanate/,

TABLE 4

Lymphatic leukemia L 1210
Experimental animals: $CDF_1$ (C3H×DBA/2)$F_1$ mice.
Tumour implant: $10^5$ tumour cells i.p.
Therapy: One injection i.p. on the day following implantation.
Evaluation: a) The survival time of the test animals (t) expressed as the percentage of that of control animals (c).
Effect (%) = t . 100/c
b. Weight change in the test animals (T) compared with that of the control animals (c) up to the 5th day.

$\Delta_r = T - C$.

c. The mortality rate must not exceed 35% in the test animals on the 5th day of therapy.

| Results: Compound | Dose mg/kg | Mortality | Weight change v (g) | Effect % |
|---|---|---|---|---|
| Dehydroepiandrosterone-3β-N-(2-chloroethyl)-N-nitroso carbamate | 1×500 | 0/40 | −2.5 | 143 |
| Androsterone-3α-N-(2-chloroethyl)-N-nitroso carbamate | 1×125 | 0/20 | −2.4 | 153 |
| Epiandrosterone-3β-N-(2-chloroethyl)-N-nitroso carbamate | 1×250 | 0/20 | −1.6 | 130 |
| Dihydrotestosterone-17β-N-(2-chloroethyl)-N-nitroso carbamate | 1×125 | 0/20 | −0.9 | 135 |
| Testosterone-17β-N-(2-chloroethyl)-N-nitroso carbamate | 1×125 | 0/40 | −1.8 | 125 |
| 19-Nortestosterone-17β-N-(2-chloroethyl)-N-nitroso carbamate | 1×31 | 0/40 | −1.0 | 142 |
| Pregnenolone-3β-N-(2-chloroethyl)-N-nitroso carbamate | 1×500 | 0/20 | −0.8 | 136 |

The following compounds also show a significant effect:
estrone-3-N-(2-chloroethyl)-N-nitroso carbamate,
androsterone-3α,17β-bis/N-(2-chloroethyl)-N-nitroso carbamate/,
prednisolone-21-N-(2-chloroethyl)-N-nitroso carbamate,
prednisolone-21/N²,N⁴-bis (2-chloroethyl)-N⁴-nitroso carbamate/.

dehydroepiandrosterone-3β-/N²,N⁴-bis (2-chloroethyl)-N⁴-nitroso allophanate/,
dehydroepiandrosterone-3β-/N²-cyclohexyl-N⁴-(2-chloroethyl)-N⁴-nitroso allophanate/,
dehydroepiandrosterone-3β-/N²-phenyl-N⁴-(2-chloroethyl)-N⁴-nitroso allophanate/,
dehydroepiandrosterone-3β-/N²-(p-chlorophenyl)-N⁴-(2-chloroethyl)-N⁴-nitroso allophanate/,
dehydroepiandrosterone-3β-/N²-(p-methoxyphenyl)-N⁴-(2-chloroethyl)-N⁴-nitroso allophanate/,
dehydroepiandrosterone-3β-/N²-(4-methylcyclohexyl)-N⁴-(2-chloroethyl)-N⁴-nitroso allophanate/.

31. A compound according to claim 17 selected from the group consisting of
17α-ethynyl-19-nortestosterone-17β-/N²,N⁴-bis (2-chloroethyl)-N⁴-nitroso allophanate/,
ethynodiol-17β-acetate-3β-/N²-cyclohexyl-N⁴-(2-chloroethyl)-N⁴-nitroso allophanate/,
ethynodiol-17β-acetate-3β-/N²-methyl-N⁴-(2-chloroethyl)-N⁴-nitroso carbamate/,
ethynodiol-17β-acetate-3β-/N²-phenyl-N⁴-(2-chloroethyl)-N-nitroso allophanate/,
ethynodiol-17β-acetate-3β-/N²-n-butyl-N-⁴-(2-chloroethyl)-N⁴-nitroso allophanate/,
ethynodiol-17β-acetate-3β-/N²-(4-methylcyclohexyl)-N⁴-(2-chloroethyl)-N⁴-nitroso allophanate/,
ethynodiol-17β-acetate-3β-/N²-phenyl-N⁴-(2-chloroethyl)-N⁴-nitroso allophanate/.

32. A compound according to claim 18 selected from the group consisting of
prednisolone-21-/N²N⁴-bis (2-chloroethyl)-N⁴-nitroso allophanate/,
prednisolone-21-/N²-cyclohexyl-N⁴-(2-chloroethyl)-N-nitroso allophanate/.

33. A compound according to claim 18 selected from the group consisting of
pregnenolone-3β-/N²-methyl-N⁴-(2-chloroethyl)-N⁴-nitroso allophanate/,
pregnenolone-3β-/N²-cyclohexyl-N⁴-(2-chloroethyl)-N⁴-nitroso allophanate/,
pregnenolone-3β-/N²,N⁴-bis (2-chloroethyl)-N⁴-nitroso allophanate/,
pregnenolone-3β-/N²-(4-methylcyclohexyl)-N⁴-(2-chloroethyl)-N⁴-nitroso allophanate/,
pregnenolone-3β-/N²-phenyl-N⁴-(2-chloroethyl)-N⁴-nitroso allophanate/.

34. A compound according to claim 19 selected from the group consisting of
cholesterol-3β-/N²-cyclohexyl-N⁴-(2-chloroethyl)-N⁴-nitroso allophanate/,
cholesterol-3β-/N²-methyl-N⁴-(2-chloroethyl)-N⁴-nitroso allophanate/,
cholesterol-3β-/N²-phenyl-N⁴-(2-chloroethyl)-N⁴-nitroso allophanate/,
cholesterol-3β-/N²,N⁴-bis (2-chloroethyl)-N⁴-nitroso allophanate/.

35. A compound according to claim 20 selected from the group consisting of
estrone-3-N-(2-chloroethyl)-N-nitroso carbamate,
17β-estradiol-3-N-(2-chloroethyl)-N-nitroso carbamate,
estradiol-17β-acetate-3-N-(2-chloroethyl)-N-nitroso carbamate,
estradiol-3-N-(2-chloroethyl)-N-nitroso carbamate-17β-(p-propoxyphenyl-propionate),
estradiol-3-methylether-17β-N-(2-chloroethyl)-N-nitroso carbamate,
estradiol-17β-N-(2-chloroethyl)-N-nitroso carbamate-3-cyclopentyl ether,
estradiol-3-acetate-17β-N-(2-chloroethyl)-N-nitroso carbamate,
estradiol-3-benzoate-17β-N-(2-chloroethyl)-N-nitroso carbamate,
estriol-16α,17β-diacetate-3-N-(2-chloroethyl)-N-nitroso carbamate,
17α-ethynylestradiol-17β-acetate-3-N-(2-chloroethyl)-N-nitroso carbamate,
17α-ethynylestradiol-3-acetate-17β-N-(2-chloroethyl)-N-nitroso carbamate,
estradiol-17β-acetate-3-N-(2-fluoroethyl)-N-nitroso carbamate,
estradiol-3-N-(2-chloroethyl)-N-nitroso carbamate-17β-valerate.

36. A compound according to claim 21 selected from the group consisting of
androsterone-3α-N-(2-chloroethyl)-N-nitroso carbamate,
epiandrosterone-3β-N-(2-chloroethyl)-N-nitroso carbamate,
dihydrotestosterone-17β-N-(2-chloroethyl)-N-nitroso carbamate,
testosterone-17β-N-(2-chloroethyl)-N-nitroso carbamate,
19-nortestosterone-17β-N-(2-chloroethyl)-N-nitroso carbamate,
androstanediol-3α-N-(2-chloroethyl)-N-nitroso carbamate,
androstanediol-3α-N-(2-chloroethyl)-N-nitroso carbamate-17β-oenanthate,
androstenediol-17β-acetate-3β-N-(2-chloroethyl)-N-nitroso carbamate,
androstenediol-3β-acetate-17β-N-(2-chloroethyl)-N-nitroso carbamate,
etiocholanolone-3β-N-(2-chloroethyl)-N-nitroso carbamate,
17α-methyltestosterone-17β-N-(2-chloroethyl)-N-nitroso carbamate,
9α-fluoro-11β-hydroxy-17α-methyltestosterone-17β-N-(2-chloroethyl)-N-nitroso carbamate,
androstenediol-17β-p-hexoxyphenylpropionate-3β-N-(2-chloroethyl)-N-nitroso carbamate,
androstenediol-17β-methylether-3β-N-(2-chloroethyl)-N-nitroso carbamate,
androstenediol-17β-benzoate-3β-N-(2-chloroethyl)-N-nitroso carbamate,
dehydroepiandrosterone-3β-N-(2-chloroethyl)-N-nitroso carbamate,
dehydroepiandrosterone-3β-N-(2-bromoethyl)-N-nitroso carbamate,
dehydroepiandrosterone-3β-N-(2-chloropropyl)-N-nitroso carbamate,
dehydroepiandrosterone-3β-N-(2-fluoroethyl)-N-nitroso carbamate.

37. A compound according to claim 22 selected from the group consisting of
17α-ethynyl-19-nortestosterone-17β-N-(2-chloroethyl)-N-nitroso carbamate,
norethynodrel-17β-N-(2-chloroethyl)-N-nitroso carbamate,
ethynodiol-17β-acetate-3β-N-(2-chloroethyl)-N-nitroso carbamate,
ethynodiol-17β-acetate-3β-N-(2-fluoroethyl)-N-nitroso carbamate,
ethynodiol-17β-N-(2-chloroethyl)-N-nitroso carbamate, ethynodiol-17β-N-(2-chloroethyl)-N-nitroso carbamate-3β-oenanthate.

38. A compound according to claim 22 selected from the group consisting of
17α-hydroxy-progesterone,17α-N-(2-chloroethyl)-N-nitroso carbamate,
6-chloro-pregna-4,6-diene-3β,17α-diol-20-one,3β-N-(2-chloroethyl)-N-nitroso carbamate.

39. A compound according to claim 23 selected from the group consisting of
deoxycorticosterone-21-N-(2-chloroethyl)-N-nitroso carbamate,
hydrocortisone-21-N-(2-chloroethyl)-N-nitroso carbamate,
prednisone-21-N-(2-chloroethyl)-N-nitroso carbamate,
prednisolone-21-N-(2-chloroethyl)-N-nitroso carbamate,
9α-fluoro-16α-methylprednisolone-21-N-(2-chloroethyl)-N-nitroso carbamate,
9α-fluoro-16β-methylprednisolone-21-N-(2-chloroethyl)-N-nitroso carbamate,
9α-fluoro-16α-hydroxyprednisolone-21-N-(2-chloroethyl)-N-nitroso carbamate,
prednisolone-11β-N-(2-chloroethyl)-N-nitroso carbamate,
prednisolone-11β-/N-(2-chloroethyl)-N-nitroso carbamate/-21-pivalate.

40. A compound according to claim 23 selected from the group consisting of
pregnenolone-3β-N-(2-chloroethyl)-N-nitroso carbamate,
pregnenolone-3β-N-(2-fluoroethyl)-N-nitroso carbamate.

41. A compound according to claim 24 selected from the group consisting of
cholesterol-3β-N-(2-chloroethyl)-N-nitroso carbamate,
cholesterol-3β-N-(2-fluoroethyl)-N-nitroso carbamate,
ergosterol-3β-N-(2-chloroethyl)-N-nitroso carbamate.

42. A compound according to claim 25 selected from the group consisting of
estradiol-3-N-(2-chloroethyl)-N-nitroso carbamate-17β-dihydrogen phosphate,
estradiol-3-N-(2-chloroethyl)-N-nitroso carbamate-17β-sodium sulphate,
estriol-3-N-(2-(2-chloroethyl)-N-nitroso carbamate-16α,17β-bishemisuccinate,
estradiol-17β-phenyl hydrogen phosphate-3-N-(2-chloroethyl)-N-nitroso carbamate,
estradiol-17β-ethyl hydrogen phosphate-3-N-(2-chloroethyl)-N-nitroso carbamate,
androstanediol-3α-N-(2-chloroethyl)-N-nitroso carbamate-17β-dihydrogen phosphate,
androstenediol-3β/N-(2-chloroethyl)-N-nitroso carbamate/-17β-phenyl hydrogen phosphate,
androstenediol-3β-/N-(2-chloroethyl)-N-nitroso carbamate/-17β-dihydrogen phosphate,
androstenediol-3β-/N-(2-chloroethyl)-N-nitroso carbamate/-17β-ethyl hydrogen phosphate,
androstenediol-3β-/N-(2-chloroethyl)-N-nitroso carbamate/-17β-sodium sulphate,
androstenediol-3β-/N²-methyl-N⁴-(2-chloroethyl)-N⁴-nitroso allophanate/-17β-dihydrogen phosphate,
androstenediol-17β-hemisuccinate-3β-N-(2-chloroethyl)-N-nitroso carbamate,
ethynodiol-17β-N-(2-chloroethyl)-N-nitroso carbamate-3β-dihydrogen phosphate,
ethynodiol-17β-N-(2-chloroethyl)-N-nitroso carbamate-3β-phenyl hydrogen phosphate,
ethynodiol-17β-N-(2-chloroethyl)-N-nitroso carbamate-3β-ethyl hydrogen phosphate,
ethynodiol-17β-N-(2-chloroethyl)-N-nitroso carbamate-3β-sodium sulphate,
prednisolone-11β-/N-(2-chloroethyl)-N-nitroso carbamate/-21-dihydrogen phosphate,
prednisolone-11β-/N-(2-chloroethyl)-N-nitroso carbamate/-21-ethyl hydrogen phosphate,
prednisolone-11β-/N-(2-chloroethyl)-N-nitroso carbamate/-21-phenyl hydrogen phosphate,
prednisolone-11β-/N-(2-chloroethyl)-N-nitroso carbamate/-21-hemisuccinate.

43. A compound according to claim 26 selected from the group consisting of
9α-fluoro-16α-hydroxyprednsolone-21-N-(2-chloroethyl)-N-nitroso carbamate, 16α,17α-acetonide.

44. A composition of matter comprising as an active ingredient one or more of the compounds according to claim 1 in combination with a pharmaceutically acceptable carrier, and, if desired, other pharmacologically active agents.

45. A method of treating a living animal body suffering from disorders responsive to treatment with anti-cancer agents and with immunosuppressive agents comprising administration of a therapeutically effective amount of a compound of claim 1 to said animal body.

46. Novel compounds having the general formula $$AR_n^3 \tag{II}$$

or functional derivatives thereof;
wherein $R^3$ is

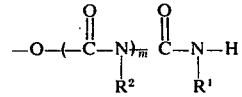

where $R^1$ is a β- or γ-halogen substituted alkyl group having 2 to 4 carbon atoms, inclusive; where the halogen of $R^1$ is selected from the group consisting of fluorine, chlorine and bromine; where m is an integer selected from the group consisting of zero and one; where $R^2$, when m is one, is selected from the group consisting of $R^1$, hydrogen, lower alkyl, 5- to 6-membered cycloalkyl, 5- to 6-membered cycloalkyl substituted with one or two substituents selected from the group consisting of halogen, lower alkyl and lower alkoxy, phenyl and phenyl substituted with one or two substituents selected from the group consisting of halogen, lower alkyl and lower alkoxy;

wherein n is one or two; and wherein A is the radical of a steroid having a cyclopentanophenanthrene carbon-carbon skeleton containing up to a maximum of 40 carbon atoms, inclusive of substituents, said carbon-carbon skeleton including a nucleus selected from the group consisting of saturated and unsaturated gonane nuclei having up to a maximum of four double bonds, said steroid radical being attached to $R^3$ in 3. A compound according to claim 2, wherein said steroid has a nucleus selected from the group consisting of: estra-1,3,5(10),16-tetraen-3-ol, estra-1,3,5(10)-trien-3-ol-17-one, estra-1,3,5(10)-triene-3,16-diol-17-ones, estra-1,3,5(10)-triene-3,17-diol-16-ones, estra-1,3,5(10)-triene-3,16,17-triols, estra-1,3,5(10)-triene-3,17-diols, androstan-3-ol-17-ones, androstan-17-ol-3-ones, androstane-3,17-diols, androstane-3,16-diol-17-ones, androst-4-en-3-ol-17-ones, androst-4-en-17-ol-3-ones, androst-4-ene-3,17-diols, androst-4-ene-11,17-diol-3-ones, androst-5-en-3-ol-17-ones, androst-5-en-17-ol-3-ones, androst-5-ene-3,17-diols, estr-4-en-17-ols, estr-4-en-17-ol-3-ones, estr-4-ene-3,17-diols, estr-5(10)-en-17-ol-3-ones, pregna-4-ene-17-ol-3,20-diones, pregna-4,6-dien-17-ol-3,20-diones, pregna-4,6-dien-3,17-diol-20-ones, pregn-5-en-3-ol-20-ones, pregn-4-en-21-ol-3,20-diones, pregn-4-ene-11,21-diol-3,20-diones, pregn-4-ene-21-ol-3,11,20-triones, pregn-4-ene-17,21-diol-3,11,20-triones, pregn-4-ene-11,17,21-triol-3,20-diones, pregn-4-ene-11,16,17,21-tetraol-3,20-diones, pregna-1,4-diene-17,21-diol-3,11,20-triones, pregna-1,4-diene-11,17,21-triol-3,20-diones, pregna-1,4-diene-11,16,17,21-tetraol-3,20-diones, cholestan-3-ols, cholest-5-en-3-ols, cholesta-5,22-dien-3-ols and cholesta-5,7,22-trien-3-ols; and wherein said steroid radical has the said steroid nucleus with a hydroxy group removed from at least one and not more than two of the said 3-, 11-, 16-, 17- and 21-positions thereof; the said radical R being attached to said steroid nucleus in at least one and not more than two of said positions.

4. A compound according to claim 3, wherein any further substitution in the carbon-carbon skeleton of said steroid nucleus is at most a tetra-substitution wherein the positions of the steroid carbon-carbon skeleton which are substituted are selected from the positions consisting of the 2-, 4-, 6-, 7-, 9-, 16-, 17-, 18- and 24-positions; where the substitution, if any, comprises at least one substituent selected from the group consisting of methyl, ethyl, methylene, ethynyl, allyl, fluoro and chloro.

5. A compound according to claim 4, wherein said steroid is selected from the group consisting of: estra-1,3,5(10)-trien-3-ol-17-one, estra-1,3,5(10)-triene-3,16-diol-17-ones, estra-1,3,5(10)-triene-3,17-diol-16-ones, estra-1,3,5(10)-triene-3,16,17-triols, estra-1,3,5(10)-triene-3,17-diols, 17-ethynyl-estra-1,3,5(10)-triene-3,17-diols and estra-1,3,5(10),16-tetraen-3-ol.

6. A compound according to claim 4, wherein said steroid nucleus is selected from the group consisting of androstan-3-ol-17-ones, androstan-17-ol-3-ones, androstane-3,17-diols, androstane-3,16-diol-17-ones, androst-4-en-3-ol-17-ones, androst-4-en-17-ol-3-ones, androst-4-ene-3,17-diols, androst-4-ene-11,17-diol-3-ones, androst-5-en-3-ol-17-ones, androst-5-en-17-ol-3-ones, androst-5-ene-3,17-diols, estr-4-en-17-ols and estr-4-en-17-ol-3-ones; any further substitution in the carbon-carbon skeleton of said steroid nucleus being based on substitution in any of the positions selected from the group consisting of the 2-, 4-, 6-, 7-, 9- and 17-positions and with substituents selected from the group consisting of methyl, ethyl and fluoro.

7. A compound according to claim 4, wherein said steroid nucleus is selected from the group consisting of: estr-4-en-17-ols, estr-4-en-17-ols-3-ones, estr-4-ene-3,17-diols, estr-5(10)-en-17-ol-3-ones, androst-4-en-17-ol-3-ones, pregna-4-ene-17-ol-3,20-diones, pregna-4,6-dien-17-ol-3,20-diones and pregna-4,6-dien-3,17-diol-20-ones; any further substitution in the carbon-carbon skeleton of said steroid nucleus being based on substitution in any of the positions selected from the group consisting of the 6-, 17- and 18-positions and with substituents selected from the group consisting of methyl, ethynyl, allyl and chloro.

8. A compound according to claim 4, wherein said steroid nucleus is selected from the group consisting of: pregn-5-en-3-ol-20-ones, pregn-4-en-21-ol-3,20-diones, pregn-4-ene-11,21-diol-3,20-diones, pregn-4-ene-21-ol-3,11,20-triones, pregn-4-ene-17,21-diol-3,11,20-triones, pregn-4-ene-11,17,21-triol-3,20-diones, pregn-4-ene-11,16,17,21-tetraol-3,20-diones, pregna-1,4-diene-17,21-diol-3,11,20-triones, pregna-1,4-diene-11,17,21-triol-3,20-diones and pregna-1,4-diene-11,16,17,21-tetraol-3,20-diones; any further substitution in the carbon-carbon skeleton of said steroid nucleus being based on substitution in any of the positions selected from the group consisting of the 6-, 9- and 16-positions and with substituents selected from the group consisting of methyl, methylene and fluoro;

9. A compound according to claim 4, wherein said steroid nucleus is selected from the group consisting of: cholestan-3-ols, cholest-5-en-3-ols, cholesta-5,22-dien-3-ols and cholesta-5,7,22-trien-3-ols; any further substitution in the carbon-carbon skeleton of said steroid nucleus being based on substitution in the 24-position and with substituents selected from the group consisting of methyl and ethyl.

10. A compound according to claim 5, wherein $R^1$ is a $\beta$-halogen substituted alkyl group, said alkyl group being selected from the group consisting of ethyl, n-propyl and n-butyl; and wherein $R^2$, when m is one, is selected from the group consisting of $R^1$; lower alkyl; cyclohexyl; cyclohexyl substituted in 4-position with a substituent selected from the group consisting of halogen, lower alkyl and lower alkoxy; phenyl; and phenyl substituted in 4-position with a substituent selected from the group consisting of halogen, lower alkyl and lower alkoxy.

11. A compound according to claim 6, wherein $R^1$ is a $\beta$-halogen substituted alkyl group, said alkyl group being selected from ethyl, n-propyl and n-butyl; and wherein $R^2$, when m is one, is selected from the group consisting of $R^1$; lower alkyl; cyclohexyl; cyclohexyl substituted in 4-position with a substituent selected from halogen, lower alkyl and lower alkoxy; phenyl; and phenyl substituted in 4-position with a substituent selected from halogen, lower alkyl and lower alkoxy, 12. A compound according to claim 7, wherein $R^1$ is a $\beta$-halogen substituted alkyl group, said alkyl group being selected from ethyl, n-propyl and n-butyl; and wherein $R^2$, when m is one, is selected from the group consisting of $R^1$; lower alkyl; cyclohexyl; cyclohexyl substituted in 4-position with a substituent selected from halogen, lower alkyl and lower alkoxy; phenyl and phenyl substituted in 4-position with a substituent selected from halogen, lower alkyl and lower alkoxy.

13. A compound according to claim 8, wherein $R^1$ is a $\beta$-halogen substituted alkyl group, said alkyl group being selected from ethyl, n-propyl and n-butyl; and wherein $R^2$, when m is one, is selected from the group consisting of $R^1$; lower alkyl; cyclohexyl; cyclohexyl substituted in 4-position with a substituent selected from halogen, lower alkyl and lower alkoxy; phenyl; and phenyl substituted in 4-position with a substituent selected from halogen, lower alkyl and lower alkoxy.

14. A compound according to claim 9, wherein $R^1$ is a β-halogen substituted alkyl group, said alkyl group being selected from ethyl, n-propyl and n-butyl; and wherein $R^2$, whem m is one, is selected from the group consisting of $R^1$; lower alkyl; cyclohexyl; cyclohexyl substituted in 4-position with a substituent selected from halogen, lower alkyl and lower alkoxy; phenyl; and phenyl substituted in 4-position with a substituent selected from halogen, lower alkyl and lower alkoxy.

15. A compound according to claim 10, wherein said steroid is selected from the group consisting of estra-1,3,5(10)-trien-3-ol-17-one, estra-1,3,5(10)-triene-3,17β-diol, estra-1,3,5(10)-triene-3,16α,17β-triol and 17α-ethynyl-estra-1,3,5(10)-triene-3,17β-diol.

16. A compound according to claim 11, wherein said steroid is selected from the group consisting of androstan-3α-ol-17-one, androstan-3β-ol-17-one, androstan-17β-ol-3-one, 2α-methylandrostan-17β-ol-3-one, 4α-methylandrostan-17β-ol-3-one, 6α-methylandrostan-17β-ol-3-one, 17α-methylandrostan-17β-ol-3-one, androstane-3α,17β-diol, androstane-3β,17β-diol, 17α-methylandrostane-3α,17β-diol, 17α-methylandrostane-3β,17β-diol, etiocholan-3α-ol-17-one, etiocholan-3β-ol-17-one, androst-4-en-3β-ol-17-one, androst-4-en-17β-ol-3-one, androst-4-ene-3β,17β-diol, 4-methylandrost-4-en-17β-ol-3-one, 6α-methylandrost-4-en-17β-ol-3-one, 17α-methylandrost-4-en-17β-ol-3-one, 17α-methylandrost-4-ene-9α-fluoro-11β,17β-dihydroxy-3-one, 7α,17α-dimethylandrost-4-en-17β-ol-3-one, androst-5-en-3α-ol-17-one, androst-5-en-3β-ol-17-one, androst-5-en-17β-ol-3-one, androst-5-ene-3α,17β-diol, androst-5-ene-3β,17β-diol, 17α-methylandrost-5-ene-3β,17β-diol, estr-4-en-17β-ol-3-one and 17α-ethyl-estr-4-en-17β-ol-3-one.

17. A compound according to claim 12, wherein $n$ is one and wherein said steroid is selected from the group consisting of 17α-ethynyl-estr-4-en-17β-ol, 17α-allyl-ester-4-en-17β-ol, 17α-ethynyl-estr-4-ene-3β,17β-diol, 17α-ethynyl-estr-4-en-17β-ol-3-one, 17β-ethynyl-18-methyl-estr-4-ene-17β-ol-3-one, 17α-ethynyl-estr-5(10)-en-17β-ol-3-one, 17α-ethynyl-androst-4-en-17β-ol-3-one, pregn-4-en-17α-ol-3,20-dione, 6α-methyl-pregn-4-en-17α-ol-3,20-dione, 6-chloro-pregna-4,6-dien-17α-ol-3,20-dione and 6-chloro-pregna-4,6-diene-3β,17α-diol-20-one.

18. A compound according to claim 13, wherein $n$ is one and wherein said steroid is selected from the group consisting of pregn-5-en-3β-ol-20-one, pregn-4-en-21-ol-3,20-dione, pregn-4-ene-11β,21-diol-3,20-dione, pregn-4-ene-17α21-diol-3,11,20-trione, pregn-4-ene-11β,17α,21-triol-3,20-dione, pregna-1,4-diene-17α,21-diol-3,11,20-trione, pregna-1,4-diene-11β,17α,21-triol-3,20-dione, 6αmethyl-pregna-1,4-diene-11β,17α,21-triol-3,20-dione, 16-methylene-pregna-1,4-diene-11β, 17α,21-triol-3,20-dione, 6α-fluoro-16α-methyl-pregna-1,4-diene-11β,17α,21-triol-3,20-dione, 9α-fluoro-16α-methyl-pregna-1,4-diene-11β,17α,21-triol-3,20-dione, 9α-fluoro-16β-methyl-pregna-1,4-diene-11β,17α,21-triol-3,20-dione, 9α-fluoro-pregna-1,4-diene-11β,16α,17α,21-tetrol-3,20-dione, 6α,9α-difluoro-16α-methyl-pregna-1,4-diene-11β,17α,21-triol-3,20-dione and 6α-fluoro-16α-methylene-pregna-1,4-diene-11β,17α,21-triol-3,20-dione.

19. A compound according to claim 14, wherein $n$ is one and wherein said steroid is selected from the group consisting of 5β-cholestan-3β-ol, 5α-cholestan-3β-ol, cholest-5-en-3β-ol and 24β-methylcholesta-5,7,22-trien-3β-ol.

20. A compound according to claim 15, wherein $n$ is one and $m$ is zero.

21. A compound according to claim 16, wherein $n$ is one and m is zero.

22. A compound according to claim 17, wherein $m$ is zero.

23. A compound according to claim 18, wherein $m$ is zero.

24. A compound according to claim 19, wherein $m$ is zero.

25. A compound according to claim 2, wherein said steroid radical has one or more hydroxy groups esterified with a polybasic acid and wherein one or more of the remaining free acid groups of said polybasic acid is in the form of the free acid or a salt thereof with a pharmaceutically acceptable organic or inorganic cation selected from the group consisting of calcium, potassium, sodium, monoethanolamine, diethanolamine, dimethylaminoethanol, N-methylglucamine, trishydroxymethylmethylamine and morpholine.

26. A compound according to claim 3, wherein hydroxy groups present in both the 16- and 17-positions of said steroid are in the form of an 16,17-acetonid.

27. A compound according to claim 15 selected from the group consisting of
estradiol-3,17β-bis/N-(2-chloroethyl)-N-nitroso carbamate/,
estriol-3-acetate-16α,17β-bis-/N-(2-chloroethyl)-N-nitroso carbamate/.

28. A compound according to claim 16 selected from the group consisting of
androstenediol-3β,17β--bis-/N-(2-chloroethyl)-N-nitroso carbamate/,
androstanediol-3α,17β-bis/N-(2-chloroethyl)-N-nitroso carbamte/.

29. A compound according to claim 15 selected from the group consisting of
estradiol-17β-acetate-3-/$N^2$,$N^4$-bis (2-chloroethyl)-$N^4$-nitroso allophanate/,
estradiol-3-acetate-17β-/$N^2$-cyclohexyl-$N^4$-(2-chloroethyl)-$N^4$-nitroso allophanate/,
estriol-3,16α-diacetate-17β-/$N^2$-cyclohexyl-$N^4$-(2-chloroethyl)-$N^4$-nitroso allophanate/,
17α-ethynylestradiol-17β-acetate-3-/$N^2$,$N^4$-bis (2-chloroethyl)-$N^4$-nitroso allophanate/,
estradiol-17β-acetate-3-/$N^2$-methyl-$N^4$-(2-chloroethyl)-$N^4$-nitroso allophanate/,
estrone-3-/$N^2$-(4-methylcyclohexyl)-$N^4$-(2-chloroethyl)-$N^4$-nitroso allophanate/,
estrone-3-/$N^2$-(4-methylphenyl)-$N^4$-(2-chloroethyl)-$N^4$-nitroso allophanate/,
estradiol-3-methylether-17β-/$N^2$-phenyl-$N^4$-(2-chloroethyl)-$N^4$-nitroso allophanate/,
estradiol-3-methylether-17β-/$N^2$-methyl-$N^4$-(2-chloroethyl)-$N^4$-nitroso allophanate.

30. A compound according to claim 16 selected from the group consisting of
dihydrotestosteron-17β-/$N^2$-cyclohexyl-$N^4$-(2-chloroethyl)-$N^4$-nitroso allophanate/,
testosterone-17β-/$N^2$-cyclohexyl-$N^4$-(2-chloroethyl)-$N^4$-nitroso allophanate/,
19-nortestosterone-17β-/$N^2$-cyclohexyl-$N^4$-(2-chloroethyl)-$N^4$-nitroso allophanate/,
dehydroepiandrosterone-3β-/$N^2$-methyl-$N^4$-(2-chloroethyl)-$N^4$-nitroso allophanate/,
dehydroepiandrosterone-3β-/$N^2$-n-butyl-$N^4$-(2-chloroethyl)-$N^4$-nitroso allophanate/, dehydroepiandrosterone-3β-/$N^2$,$N^4$-bis (2-chloroethyl)-$N^4$-nitroso allophanate/,
dehydroepiandrosterone-3β-/$N^2$-cyclohexyl-$N^4$-(2-chloroethyl)-$N^4$-nitroso allophanate/,
dehydroepiandrosterone-3β-/$N^2$-phenyl-$N^4$-(2-chloroethyl)-$N^4$-nitroso allophanate/,
dehydroepiandrosterone-3β-/$N^2$-(p-chlorophenyl)-$N^4$-(2-chloroethyl)-$N^4$-nitroso allophanate/,
dehydroepiandrosterone-3β-/$N^2$-(p-methoxyphenyl)-$N^4$-(2-chloroethyl)-$N^4$-nitroso allophanate/,
dehydroepiandrosterone-3β-/$N^2$-(4-methylcyclohexyl)-$N^4$-(2-chloroethyl)-$N^4$-nitroso allophanate/.

31. A compound according to claim 17 selected from the group consisting of
17α-ethynyl-19-nortestosterone-17β-/$N^2$,$N^4$-bis (2-chloroethyl)-$N^4$-nitroso allophanate/,
ethynodiol-17β-acetate-3β-/$N^2$-cyclohexyl-$N^4$-(2-chloroethyl)-$N^4$-nitroso allophanate/,
ethynodiol-17β-acetate-3β-/$N^2$-methyl-$N^4$-(2-chloroethyl)-$N^4$-nitroso carbamate/,
ethynodiol-17β-acetate-3β-/$N^2$-phenyl-$N^4$-(2-chloroethyl)-$N^4$-nitroso allophanate/,
ethynodiol-17β-acetate-3β-/$N^2$-n-butyl-N-$^4$-(2-chloroethyl)-$N^4$-nitroso allophanate/,
ethynodiol-17β-acetate-3β-/$N^2$-(4-methylcyclohexyl)-$N^4$-(2-chloroethyl)-$N^4$-nitroso allophanate/,
ethynodiol-17β-acetate-3β-/$N^2$-phenyl-$N^4$-(2-chloroethyl)-$N^4$-nitroso allophanate/.

32. A compound according to claim 18 selected from the group consisting of
prednisolone-21-/$N^2$$N^4$-bis (2-chloroethyl)-$N^4$-nitroso allophanate/,
prednisolone-21-/$N^2$-cyclohexyl-$N^4$-(2-chloroethyl)-$N^4$-nitroso allophanate/.

33. A compound according to claim 18 selected from the group consisting of
pregnenolone-3β-/$N^2$-methyl-$N^4$-(2-chloroethyl)-$N^4$-nitroso allophanate/,
pregnenolone-3β-/$N^2$-cyclohexyl-$N^4$-(2-chloroethyl)-$N^4$-nitroso allophanate/,
pregnenolone-3β-/$N^2$,$N^4$-bis (2-chloroethyl)-$N^4$-nitroso allophanate/,
pregnenolone-3β-/$N^2$-(4-methylcyclohexyl)-$N^4$-(2-chloroethyl)-$N^4$-nitroso allophanate/,
pregnenolone-3β-/$N^2$-phenyl-$N^4$-(2-chloroethyl)-$N^4$-nitroso allophanate/.

34. A compound according to claim 19 selected from the group consisting of
cholesterol-3β-/$N^2$-cyclohexyl-$N^4$-(2-chloroethyl)-$N^4$-nitroso allophanate/,
cholesterol-3β-/$N^2$-methyl-$N^4$-(2-chloroethyl)-$N^4$-nitroso allophanate/,
cholesterol-3β-/$N^2$-phenyl-$N^4$-(2-chloroethyl)-$N^4$-nitroso allophanate/,
cholesterol-3β-/$N^2$,$N^4$-bis (2-chloroethyl)-$N^4$-nitroso allophanate/.

35. A compound according to claim 20 selected from the group consisting of
estrone-3-N-(2-chloroethyl)-N-nitroso carbamate,
17β-estradiol-3-N-(2-chloroethyl)-N-nitroso carbamate,
estradiol-17β-acetate-3-N-(2-chloroethyl)-N-nitroso carbamate,
estradiol-3-N-(2-chloroethyl)-N-nitroso carbamate-17β-(p-propoxyphenyl-propionate),
estradiol-3-methylether-17β-N-(2-chloroethyl)-N-nitroso carbamate,
estradiol-17β-N-(2-chloroethyl)-N-nitroso carbamate-3-cyclopentyl ether,
estradiol-3-acetate-17β-N-(2-chloroethyl)-N-nitroso carbamate,
estradiol-3-benzoate-17β-N-(2-chloroethyl)-N-nitroso carbamate,
estriol-16α,17β-diacetate-3-N-(2-chloroethyl)-N-nitroso carbamate,
17α-ethynylestradiol-17β-acetate-3-N-(2-chloroethyl)-N-nitroso carbamate,
17α-ethynylestradiol-3-acetate-17β-N-(2-chloroethyl)-N-nitroso carbamate,
estradiol-17β-acetate-3-N-(2-fluoroethyl)-N-nitroso carbamate,
estradiol-3-N-(2-chloroethyl)-N-nitroso carbamate-17β-valerate.

36. A compound according to claim 21 selected from the group consisting of
androsterone-3α-N-(2-chloroethyl)-N-nitroso carbamate,
epiandrosterone-3β-N-(2-chloroethyl)-N-nitroso carbamate,
dihydrotestosterone-17β-N-(2-chloroethyl)-N-nitroso carbamate,
testosterone-17β-N-(2-chloroethyl)-N-nitroso carbamate,
19-nortestosterone-17β-N-(2-chloroethyl)-N-nitroso carbamate,
androstanediol-3α-N-(2-chloroethyl)-N-nitroso carbamate,
androstanediol-3α-N-(2-chloroethyl)-N-nitroso carbamate-17β-oenanthate,
androstenediol-17β-acetate-3β-N-(2-chloroethyl)-N-nitroso carbamate,
androstenediol-3β-acetate-17β-N-(2-chloroethyl)-N-nitroso carbamate,
etiocholanolone-3β-N-(2-chloroethyl)-N-nitroso carbamate,
17α-methyltestosterone-17β-N-(2-chloroethyl)-N-nitroso carbamate,
9α-fluoro-11β-hydroxy-17α-methyltestosterone-17β-N-(2-chloroethyl)-N-nitroso carbamate,
androstenediol-17β-p-hexoxyphenylpropionate-3β-N-(2-chloroethyl)-N-nitroso carbamate,
androstenediol-17β-methylether-3β-N-(2-chloroethyl)-N-nitroso carbamate,
androstenediol-17β-benzoate-3β-N-(2-chloroethyl)-N-nitroso carbamate,
dehydroepiandrosterone-3β-N-(2-chloroethyl)-N-nitroso carbamate,
dehydroepiandrosterone-3β-N-(2-bromoethyl)-N-nitroso carbamate,
dehydroepiandrosterone-3β-N-(2-chloropropyl)-N-nitroso carbamate,
dehydroepiandrosterone-3β-N-(2-fluoroethyl)-N-nitroso carbamate.

37. A compound according to claim 22 selected from the group consisting of
17α-ethynyl-19-nortestosterone-17β-N-(2-chloroethyl)-N-nitroso carbamate,
norethynodrel-17β-N-(2-chloroethyl)-N-nitroso carbamate,
ethynodiol-17β-acetate-3β-N-(2-chloroethyl)-N-nitroso carbamate,
ethynodiol-17β-acetate-3β-N-(2-fluoroethyl)-N-nitroso carbamate,
ethynodiol-17β-N-(2-chloroethyl)-N-nitroso carbamate, ethynodiol-17β-N-(2-chloroethyl)-N-nitroso carbamate-3β-oenanthate.

38. A compound according to claim 22 selected from the group consisting of
17α-hydroxy-progesterone,17α-N-(2-chloroethyl)-N-nitroso carbamate,
6-chloro-pregna-4,6-diene-3β,17α-diol-20-one,3β-N-(2-chloroethyl)-N-nitroso carbamate.

39. A compound according to claim 23 selected from the group consisting of
deoxycorticosterone-21-N-(2-chloroethyl)-N-nitroso carbamate,
hydrocortisone-21-N-(2-chloroethyl)-N-nitroso carbamate,
prednisone-21-N-(2-chloroethyl)-N-nitroso carbamate,
prednisolone-21-N-(2-chloroethyl)-N-nitroso carbamate,
9α-fluoro-16α-methylprednisolone-21-N-(2-chloroethyl)-N-nitroso carbamate,
9α-fluoro-16β-methylprednisolone-21-N-(2-chloroethyl)-N-nitroso carbamate,
9α-fluoro-16α-hydroxyprednisolone-21-N-(2-chloroethyl)-N-nitroso carbamate,
prednisolone-11β-N-(2-chloroethyl)-N-nitroso carbamate,
prednisolone-11β-/N-(2-chloroethyl)-N-nitroso carbamate/-21-pivalate.

40. A compound according to claim 23 selected from the group consisting of
pregnenolone-3β-N-(2-chloroethyl)-N-nitroso carbamate,
pregnenolone-3β-N-(2-fluoroethyl)-N-nitroso carbamate.

41. A compound according to claim 24 selected from the group consisting of
cholesterol-3β-N-(2-chloroethyl)-N-nitroso carbamate,
cholesterol-3β-N-(2-fluoroethyl)-N-nitroso carbamate,
ergosterol-3β-N-(2-chloroethyl)-N-nitroso carbamate.

42. A compound according to claim 25 selected from the group consisting of
estradiol-3-N-(2-chloroethyl)-N-nitroso carbamate-17β-dihydrogen phosphate,
estradiol-3-N-(2-chloroethyl)-N-nitroso carbamate-17β-sodium sulphate,
estriol-3-N-(2-(2-chloroethyl)-N-nitroso carbamate-16α,17β-bishemisuccinate,
estradiol-17β-phenyl hydrogen phosphate-3-N-(2-chloroethyl)-N-nitroso carbamate,
estradiol-17β-ethyl hydrogen phosphate-3-N-(2-chloroethyl)-N-nitroso carbamate,
androstanediol-3α-N-(2-chloroethyl)-N-nitroso carbamate-17β-dihydrogen phosphate,
androstenediol-3β/N-(2-chloroethyl)-N-nitroso carbamate/-17β-phenyl hydrogen phosphate,
androstenediol-3β-/N-(2-chloroethyl)-N-nitroso carbamate/-17β-dihydrogen phosphate,
androstenediol-3β-/N-(2-chloroethyl)-N-nitroso carbamate/-17β-ethyl hydrogen phosphate,
androstenediol-3β-/N-(2-chloroethyl)-N-nitroso carbamate/-17β-sodium sulphate,
androstenediol-3β-/N²-methyl-N⁴-(2-chloroethyl)-N⁴-nitroso allophanate/-17β-dihydrogen phosphate,
androstenediol-17β-hemisuccinate-3β-N-(2-chloroethyl)-N-nitroso carbamate,
ethynodiol-17β-N-(2-chloroethyl)-N-nitroso carbamate-3β-dihydrogen phosphate,
ethynodiol-17β-N-(2-chloroethyl)-N-nitroso carbamate-3β-phenyl hydrogen phosphate,
ethynodiol-17β-N-(2-chloroethyl)-N-nitroso carbamate-3β-ethyl hydrogen phosphate,
ethynodiol-17β-N-(2-chloroethyl)-N-nitroso carbamate-3β-sodium sulphate,
prednisolone-11β-/N-(2-chloroethyl)-N-nitroso carbamate/-21-dihydrogen phosphate,
prednisolone-11β-/N-(2-chloroethyl)-N-nitroso carbamate/-21-ethyl hydrogen phosphate,
prednisolone-11β-/N-(2-chloroethyl)-N-nitroso carbamate/-21-phenyl hydrogen phosphate,
prednisolone-11β-/N-(2-chloroethyl)-N-nitroso carbamate/-21-hemisuccinate.

43. A compound according to claim 26 selected from the group consisting of
9α-fluoro-16α-hydroxyprednsolone-21-N-(2-chloroethyl)-N-nitroso carbamate, 16α,17α-acetonide.

44. A composition of matter comprising as an active ingredient one or more of the compounds according to claim 1 in combination with a pharmaceutically acceptable carrier, and, if desired, other pharmacologically active agents.

45. A method of treating a living animal body suffering from disorders responsive to treatment with anti-cancer agents and with immunosuppressive agents comprising administration of a therapeutically effective amount of a compound of claim 1 to said animal body.

46. Novel compounds having the general formula $$AR_n^3 \quad (II)$$

or functional derivatives thereof;
wherein $R^3$ is

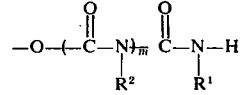

where $R^1$ is a β- or γ-halogen substituted alkyl group having 2 to 4 carbon atoms, inclusive; where the halogen of $R^1$ is selected from the group consisting of fluorine, chlorine and bromine; where m is an integer selected from the group consisting of zero and one; where $R^2$, when m is one, is selected from the group consisting of $R^1$, hydrogen, lower alkyl, 5- to 6-membered cycloalkyl, 5- to 6-membered cycloalkyl substituted with one or two substituents selected from the group consisting of halogen, lower alkyl and lower alkoxy, phenyl and phenyl substituted with one or two substituents selected from the group consisting of halogen, lower alkyl and lower alkoxy;
wherein n is one or two; and
wherein A is the radical of a steroid having a cyclopentanophenanthrene carbon-carbon skeleton containing up to a maximum of 40 carbon atoms, inclusive of substituents, said carbon-carbon skeleton including a nucleus selected from the group consisting of saturated and unsaturated gonane nuclei having up to a maximum of four double bonds, said steroid radical being attached to $R^3$ in at least one and not more than two of the 3-, 11-, 16-, 17- and 21-positions thereof when m is one, and at at least one and not more than two of the 3-, 11-, 16- and 17-positions thereof when m is zero, said positions being identified according to steroid nomenclature.

47. Novel compounds having the general formula

AR$_n^4$           (III)

or functional derivatives thereof;
wherein R$^4$ is

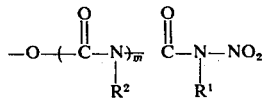

where R$^1$ is a β- or γ-halogen substituted alkyl group having 2 to 4 carbon atoms, inclusive; where the halogen of R$^1$ is selected from the group consisting of fluorine, chlorine and bromine; where m is an integer selected from the group consisting of zero and one; where R$^2$, when m is one, is selected from the group consisting of R$^1$, hydrogen, lower alkyl, 5- to 6-membered cycloalkyl, 5- to 6-membered cycloalkyl substituted with one or two substituents selected from the group consisting of halogen, lower alkyl and lower alkoxy, phenyl and phenyl substituted with one or two substituents selected from the group consisting of halogen, lower alkyl and lower alkoxy;
wherein n is one or two; and
wherein A is the radical of a steroid having a cyclopentanophenanthrene carbon-carbon skeleton containing up to a maximum of 40 carbon atoms, inclusive of substituents, said carbon-carbon skeleton including a nucleus selected from the group consisting of saturated and unsaturated gonane nuclei having up to a maximum of four double bonds, said steroid radical being attached to R$^4$ in at least one and not more than two of the 3-, 11-, 16-, 17- and 21 positions thereof, said positions being identified according to steroid nomenclature.

48. A compound according to claim 46, wherein said radical of a steroid has a carbon-carbon skeleton selected from the group consisting of:
estra-1,3,5(10)-triene, estra-1,3,5(10),16-tetraene, androstane, androst-4-ene, androst-5-ene, estr-4-ene, estr-5(10)-ene, pregn-4-ene, pregna-4,6-diene, pregn-5-ene, pregna-1,4-diene, cholestan, cholest-5-ene, cholesta-5,22-diene and cholesta-5,7,22-triene carbon-carbon skeleton; wherein any hydroxy group present in said radical may be free; esterified with a monocarboxylic acid selected from the group consisting of aliphatic carboxylic acids having at most 10 carbon atoms, alicyclic carboxylic acids having 6 or 7 carbon atoms, benzoic acid and arylaliphatic acids having at most 15 carbon atoms, or with a polybasic acid selected from the group consisting of aliphatic dicarboxylic acids having at most 4 carbon atoms, benzene dicarboxylic acids, mono lower alkyl and mono phenyl phosphoric acids and inorganic polybasic acids, and where one or more of the remaining free acid group or groups of said polybasic acids is in the free acid form or as a salt thereof with a phar-
maceutically acceptable organic or inorganic cation; or etherified with an alcohol selected from the group consistin of aliphatic and alicyclic alcohols having at most 6 carbon atoms.

49. A compound according to claim 47, wherein said radical of a steroid has a carbon-carbon skeleton selected from the group consisting of: estra-1,3,5(10)-triene, estra-1,3,5(10),16-tetraene, androstane, androst-4-ene, androst-5-ene, estr-4-ene, estr-5(10)-ene, pregn-4-ene, pregna-4,6-diene, pregn-5-ene, pregna-1,4-diene, cholestan, cholest-5-ene, cholesta-5,22-diene and cholesta-5,7,22-triene carbon-carbon skeletons; wherein any hydroxy group present in said radical may be free; esterified with a monocarboxylic acid selected from the group consisting of aliphatic carboxylic acids having at most 10 carbon atoms, alicyclic carboxylic acids having 6 or 7 carbon atoms, benzoic acid and arylaliphatic acids having at most 15 carbon atoms, or with a polybasic acid selected from the group consisting of aliphatic dicarboxylic acids having at most 4 carbon atoms, benzene dicarboxylic acids, mono lower alkyl and mono phenyl phosphoric acids and inorganic polybasic acids, and where one or more of the remaining free acid group or groups of said polybasic acids is in the free acid form or as a salt thereof with a pharmaceutically acceptable organic or inorganic cation; or etherified with an alcohol selected from the group consisting of aliphatic and alicyclic alcohols having at most 6 carbon atoms.

50. A compound according to claim 48, wherein said steroid has a nucleus selected from the group consisting of: estra-1,3,5(10),16-tetraen-3-ol, estra-1,3,5(10)-trien-3-ol-17one, estra-1,3,5(10)-triene-3,16-diol-17-ones, estra-1,3,5(10)-triene-3,17-diol-16-ones, estra-1,3,5(10)-triene-3,16,17-triols, estra-1,3,5(10)-triene-3,17-diols, androstan-3-ol-17-ones, androstan-17-ol-3-ones, androstane-3,17-diols, androstane-3,16-diol-17-ones, androst-4-en-3-ol-17-ones, androst-4-en-17-ol-3-ones, androst-4-ene-3,17-diols, androst-4-ene-11,17-diol-3-ones, androst-5-en-3-ol-17-ones, androst-5-en-17-ol-3-ones, androst-5-ene-3,17-diols, estr-4-en-17-ols, estr-4-en-17-ol-3-ones, estr-4-ene-3,17-diols, estr-5(10)-en-17-ol-3-ones, pregna-4-ene-17-ol-3,20-diones, pregna-4,6-dien-17-ol- 3,20-diones, pregna-4,6-dien-3,17-diol-20-ones, pregn-5-en-3-ol-20-ones, pregn-4-ene-11,21-diol-3,20-diones, pregn-4-ene-17,21-diol-3,11,20-triones, pregn-4-ene-11,17,21-triol-3,20-diones, pregn-4-ene-11,16,17,21-tetraol3,20-diones, pregna-1,4-diene-17,21-diol-3,11,20-triones, pregna-1,4-diene-11,17,21-triol-3,20-diones, pregna-1,4-diene-11,16,17,21-tetraol-3,20-diones, cholestan-3-ols, cholest-5-en-3-ols, cholesta-5,22-dien-3-ols and cholesta-5,7,22-trien-3-ols; and wherein said steroid radical has the said steroid nucleus with a hydroxy group removed from at least one and not more than two of the said 3-, 11-, 16-, 17- and 21-positions thereof; the said radical R$^3$ being attached to said steroid nucleus in at least one and not more than two of said positions; R$^3$ having the meaning given in claim 46 above.

51. A compound according to claim 49, wherein said steroid has a nucleus selected from the group consisting of: estra-1,3,5(10),16-tetraen-3-ol, estra-1,3,5(10)-trien-3-ol-17-one, estra-1,3,5(10)-triene-3,16-diol-17-ones, estra-1,3,5(10)-triene-3,17-diol-16-ones, estra-1,3,5(10)-triene-3,16,17-triols, estra-1,3,5(10)-triene-3,17-diols, androstan-3-ol-17-ones, androstan-17-ol-3-ones, androstane-3,17-diols, androstane-3,16- diol-17-ones, androst-4-en-3-ol-17-ones, androst-4-en-17-ol-3-ones, androst-4-ene-3,17-diols, androst-4-ene-11,17-diol-3-ones, androst-5-en-3-ol-17-ones, androst-5-en-17-ol-3-ones, androst-5-ene-3,17-diols, estr-4-en-17-ols, estr-4-en-17-ol-3-ones, estr-4-ene-3,17-diols, estr-5(10)-en-17-ol-3-ones, pregna-4-ene-17-ol-3,20-diones, pregna-4,6-dien-17-ol-3,20-diones, pregna-4,6-dien-3,17-diol-20-ones, pregn-5en-3-ol-20-ones, pregn-4-en-21-ol-3,20-diones, pregn-4-ene-11,21-diol-3,20-diones, pregn-4-ene-21-ol-3,11,20-triones, pregn-4-ene-17,21-diol-3,11,20-triones, pregn-4-ene-11,17,21-triol-3,20-diones, pregn-4-ene-11,16,17,21-tetraol-3,20-diones, pregna-1,4-diene-17,21-diol-3,11,20-triones, pregna-1,4-diene-11,17,21-triol-3,20-diones, pregna-1,4-diene-11,16,17,21-tetraol-3,20-diones, cholestan-3-ols, cholest-5-en-3-ols, cholesta-5,22-dien-3-ols and cholesta-5,7,22-trien-3-ols; and wherein said steroid radical has the said steroid nucleus with a hydroxy group removed from at least one and not more than two of the said 3-, 11-, 16-, 17- and 21-positions thereof; the said radical $R^4$ being attached to said steroid nucleus in at least one and not more than two of said positions; $R^4$ having the meaning given in claim 47 above.

52. A compound according to claim 50, wherein any further substitution in the carbon-carbon skeleton of said steroid nucleus is at most a tetra-substitution wherein the positions of the steroid carbon-carbon skeleton which are substituted are selected from the positions consisting of the 2-, 4-, 6-, 7-, 9-, 16-, 17-, 18- and 24- positions; where the substitution, if any, comprises at least one substituent selected from the group consisting of methyl, ethyl, methylene, ethynyl, allyl, fluoro and chloro.

53. A compound according to claim 51, wherein any further substitution in the carbon-carbon skeleton of said steroid nucleus is at most a tetra-substitution wherein the positions of the steroid carbon-carbon skeleton which are substituted are selected from the positions consisting of the 2-, 4-, 6-, 7-, 9-, 16-, 17-, 18- and 24- positions; where the substitution, if any, comprises at least one substituent selected from the group consisting of methyl, ethyl, methylene, ethynyl, allyl, fluoro and chloro.

54. A compound according to claim 52, wherein said steroid is selected from the group consisting of estra-1,3,5(10)-trien-3-ol-17-one, estra-1,3,5(10)-triene-3-17$\beta$-diol, estra-1,3,5(10)-triene-3,16$\alpha$,17$\beta$-triol, 17$\alpha\lambda$ ethynyl-estra-1,3,5(10)-triene-3,17$\beta$-diol, androstan-3$\alpha$-ol-17-one, androstan-3$\beta$-ol-17-one, androstan-17$\beta$-ol-3-one, androstane-3$\alpha$,17$\beta$-diol, etiocholan-3$\alpha$-ol-17-one, androst-4-en-17$\beta$-ol-3-one, 17$\alpha$-methylandrost-4-en-17$\beta$-ol-3-one, 17$\alpha$-methylandrost-4-ene-9$\alpha$-fluoro-11$\beta$,17$\beta$-dihydroxy-3-one, androst-5-en-3$\beta$-ol-17-one, androst-5-ene-3$\beta$,17$\beta$-diol, estr-4-en-17$\beta$-ol-3-one, 17$\alpha$-ethynyl-estr-4-ene-3$\beta$,17$\beta$-diol, 17$\alpha$-ethynyl-estr-4-en-17$\beta$-ol-3-one, 17$\alpha$-ethynyl-estr-5(10)-en-17$\beta$-ol-3-one, pregn-4-en-17$\alpha$-ol-3,20-dione, 6-chloro-pregna-4,6-diene-3$\beta$,17$\alpha$-diol-20-one, pregn-5-en-3$\beta$-ol-20-one, pregn-4-en-21-ol-3,20-dione, pregn-4-ene-11$\beta$,17$\alpha$,21-triol-3,20-dione, pregna-1,4-diene-11$\beta$,17$\alpha$,21-triol-3,20-dione,9$\alpha$-fluoro-16$\alpha$-methyl-pregna-1,4-diene-11$\beta$, 17$\alpha$,21-triol-3,20-dione, 9$\alpha$-fluoro-16$\beta$-methyl-pregna-1,4-diene-11$\beta$, 17$\alpha$,21-triol-3,20-dione, 9$\alpha$-fluoro-pregna-1,4-diene-11$\beta$, 16$\alpha$,17$\alpha$,21-tetrol-3,20-dione and cholest-5-en-3$\beta$-ol.

55. A compound according to claim 53, wherein said steroid is selected from the group consisting of estra-1,3,5(10)-trien-3-ol-17-one, estra-1,3,5(10)-triene-3-17$\beta$-diol, estra-1,3,5(10)-triene-3,16$\alpha$,17$\beta$-triol, 17$\alpha$-ethynyl-estra-1,3,5(10)-triene-3,17$\beta$-diol, endrostan-3$\alpha$-ol-17-one, androstan-3$\beta$-ol-17-one, androstan-17$\beta$-ol-3-one, androstane-3$\alpha$,17$\beta$-diol, etiocholan-3$\alpha$-ol-17-one, androst-4-en-17$\beta$-ol-3-one, 17$\alpha$-methylandrost-4-en-17$\beta$-ol-3-one, 17$\alpha$-methylandrost-4-ene-9$\alpha$-fluoro-11$\beta$,17$\beta$-dihydroxy-3-one, androst-5-en-3$\beta$-ol-17-one, androst-5-ene-3$\beta$,17$\beta$-diol, estr-4-en-17$\beta$-ol-3-one, 17$\alpha$-ethynyl-estr-4-ene-3$\beta$,17$\beta$-diol, 17$\alpha$-ethynyl-estr-4-en-17$\beta$-ol-3-one, 17$\alpha$-ethynyl-estr-5(10)-en-17$\beta$-ol-3-one, pregn-4-en-17$\alpha$-ol-3,20-dione, 6-chloro-pregna-4,6-diene-3$\beta$,17$\alpha$-diol-20-one, pregn-5-en-3$\beta$-ol-20-one, pregn-4-en-21-ol-3,20-dione, pregn-4-ene-11$\beta$,17$\alpha$,21-triol-3,20-dione, pregna-1,4-diene-11$\beta$,17$\alpha$,21-triol-3,20-dione,9$\alpha$-fluoro-16$\alpha$-methyl-pregna-1,4-diene-11$\beta$, 17$\alpha$,21-triol-3,20-dione, 9$\alpha$-fluoro-16$\beta$-methyl-pregna-1,4-diene-11$\beta$, 17$\alpha$,21-triol-3,20-dione, 9$\alpha$-fluoro-pregna-1,4-diene-11$\beta$, 16$\alpha$,17$\alpha$,21-tetrol-3,20-dione and cholest-5-en-3$\beta$-ol.

56. A compound according to claim 54, wherein $R^1$ is a $\beta$-halogen substituted alkyl group, said alkyl group being selected from the group consisting of ethyl, n-propyl and n-butyl; and wherein $R^2$, when $m$ is one, is selected from the group consisting of $R^1$; lower alkyl; cyclohexyl; cyclohexyl substituted in 4-position with a substituent selected from the group consisting of halogen, lower alkyl and lower alkoxy; phenyl; and phenyl substituted in 4-position with a substituent selected from the group consisting of halogen, lower alkyl and lower alkoxy.

57. A compound according to claim 55, wherein $R^1$ is a $\beta$-halogen substituted alkyl group, said alkyl group being selected from the group consisting of ethyl, n-propyl and n-butyl; and wherein $R^2$, when m is one, is selected from the group consisting of $R^1$; lower alkyl; cyclohexyl; cyclohexyl substituted in 4-position with a substituent selected from the group consisting of halogen, lower alkyl and lower alkoxy; phenyl; and phenyl substituted in 4-position with a substituent selected from the group consisting of halogen, lower alkyl and lower alkoxy.

58. A compound according to claim 56, wherein $m$ is one and $n$ is one.

59. A compound according to claim 57 selected from the group consisting of
androstenediol-3$\beta$,17$\beta$-bis-/N-(2-chloroethyl)-N-nitro carbamate,
androstanediol-3$\alpha$,17$\beta$-bis-/N-(2-chloroethyl)-N-nitro carbamate,
androstenediol-3$\beta$-/N-(2-chloroethyl)-N-nitro carbamate/-17$\beta$-dihydrogen phosphate,
androstenediol-17$\beta$-hemisuccinate-3$\beta$-N-(2-chloroethyl)N-nitro carbamate,
ethynodiol-17$\beta$-N-(2-chloroethyl)-N-nitro carbamate-3$\beta$-ethyl hydrogen phosphate,
cholesterol-3$\beta$-N-(2-chloroethyl)-N-nitro carbamate,
cholesterol-3$\beta$-N-(2-fluoroethyl)-N-nitro carbamate.

60. A compound according to claim 56 selected from the group consisting of
estrone-3-N-(2-chloroethyl) carbamate,
estradiol-3-N-(2-chloroethyl) carbamate-17$\beta$-(p-propoxyphenylpropionate),
estradiol-17$\beta$-N-(2-chloroethyl) carbamate-3-cyclopentyl ether,
estriol-3-N-(2-chloroethyl) carbamate-16$\alpha$,17$\beta$-bishemisuccinate, 17α-ethynylestradiol-17β-acetate-3-N-(2-chloroethyl) carbamate,
17α-ethynylestradiol-3-acetate-17β-N-(2-chloroethyl) carbamate,
androsterone-3α-N-(2-chloroethyl) carbamate,
epiandrosterone-3β-N-(2-chloroethyl) carbamate,
dihydrotestosterone-17β-N-(2-chloroethyl) carbamate,
testosterone-17β-N-(2-chloroethyl) carbamate,
19-nortestosterone-17β-N-(2-chloroethyl) carbamate,
androstenediol-3β,17β-bis/N-(2-chloroethyl) carbamate,
androstenediol-3β-/N-(2-chloroethyl) carbamate-17β-dihydrogen phosphate,
dehydroepiandrosterone-3β-N-(2-chloroethyl) carbamate,
dehydroepiandrosterone-3β-N-(2-bromoethyl) carbamate,
dehydroepiandrosterone-3β-N-(2-chloropropyl) carbamate,
dehydroepiandrosterone-3β-N-(2-fluoroethyl) carbamate,
17α-hydroxi-progesterone,17α-N-(2-chloroethyl) carbamate,
17α-ethynyl-19-nortestosterone-17β-N-(2-chloroethyl) carbamate,
norethynodrel-17β-N-(2-chloroethyl) carbamate,
6-chloropregna-4,6-diene-3β,17α-diol-20-one-3β-N-(2-chloroethyl) carbamate,
ethynodiol-17β-N-(2-chloroethyl) carbamate-3β-oenanthate,
pregnenolone-3β-N-(2-chloroethyl) carbamate,
prednisolone-11β-N-(2-chloroethyl) carbamate,
cholesterol-3β-N-(2-chloroethyl) carbamate.

61. A compound according to claim 57 selected from the group consisting of
androstenediol-3β-/N$^2$-methyl-N$^4$-(2-chloroethyl)-N$^4$-nitro allophanate/-17β-dihydrogen phosphate,
ethynodiol-17β-acetate-3β-/N$^2$-cyclohexyl-N$^4$-(2-chloroethyl)-N$^4$-nitro allophanate,
cholesterol-3β-/N$^2$,N$^4$-bis (2-chloroethyl)-N$^4$-nitro allophanate/.

62. A compound according to claim 58 selected from the group consisting of
estradiol-17β-acetate-3-/N$^2$, N$^4$-bis (2-chloroethyl) allophanate/,
estriol-3,16α-diacetate-17β-/N-cyclohexyl-N$^4$-(2-chloroethyl) allophanate,
17α-ethynylestradiol-17β-acetate-3-/N$^2$,N$^4$-bis (2-chloroethyl) allophanate,
estrone-3-/N$^2$-(4-methylphenyl)-N$^4$-(2-chloroethyl) allophanate/,
estradiol-3-methylether-17β-/N$^2$-methyl-N$^4$-(2-chloroethyl) allophanate,
dihydrotestosterone-17β-N$^2$-cyclohexyl-N$^4$-(2-chloroethyl) allophanate/,
testosterone-17β-/N$^2$-cyclohexyl-N$^4$-(2-chloroethyl) allophanate/,
19-nortestosterone-17β-/N$^2$-cyclohexyl-N$^4$-(2-chloroethyl) allophanate/,
androstenediol-3β-/N$^2$-methyl-N$^4$-(2-chloroethyl) allophanate/17β-dihydrogen phosphate,
dehydroepiandrosterone-3β-/N$^2$-methyl-N$^4$-(2-chloroethyl) allophanate/,
dehydroepiandrosterone-3β-/N$^2$-cyclohexyl-N$^4$-(2-chloroethyl) allophanate/,
dehydroepiandrosterone-3β-/N$^2$-(p-chlorophenyl)-N$^4$-(2-chloroethyl) allophanate/,
dehydroepiandrosterone-3β-/N$^2$-(p-methoxyphenyl)-N$^4$-(2-chloroethyl) allophanate/,
17α-ethynyl-19-nortestosterone-17β-/N$^2$,N$^4$-bis (2-chloroethyl) allophanate/,
ethynodiol-17β-acetate-3β-/N$^2$-n-butyl-N$^4$-(2-chloroethyl) allophanate/,
prednisolone-21-N$^2$,N$^4$-bis (2-chloroethyl) allophanate/,
pregnenolone-3β-/N$^2$-(4-methylcyclohexyl)-N$^4$-(2-chloroethyl) allophanate,
cholesterol-3β-N$^2$-phenyl-N$^4$-(2-chloroethyl) allophanate/.

* * * * *

UNITED STATES PATENT OFFICE
CERTIFICATE OF CORRECTION

Patent No. 3,963,707   Dated September 1, 1976

Inventor(s)   Knut Bertil Högberg, et al.

It is certified that error appears in the above-identified patent and that said Letters Patent are hereby corrected as shown below:

Col. 4, line 58 - "teroid"  --- steroid ---

Col. 7, line 35 - "pregn-5-en-3β-ol-2-one"  --- pregn-5-en-3β-ol-20-one ---

Col. 12, line 12 - "+ n H-N-C$\frac{1}{m}$ N"  --- + n H $(N-C\frac{1}{m}$ N ---

Col. 13, line 20 - "A-O-C-N$\frac{1}{m}$ C-NH)$_n$"--- A$(O(C-N\frac{1}{m}$ C-NH)$_n$ ---

Col. 19, line 9 - "-acetate-3-$N^2$,"  --- -acetate-3-/$N^2$, ---

Col. 19, line 11 - "-acetate-3-N/$N^2$,$N^4$-"  --- -acetate-3-/$N^2$,$N^4$- ---

Col. 19, line 33 - "androstanediol-[3a-"  --- androstanediol-3a- ---

Col. 19, line 40 - "-3βn(2-"  --- -3β-N-(2- ---

Col. 20, line 63 - "-acetate-3-$N^2$-"  - --- -acetate-3-/$N^2$- ---

Col. 22, line 15 - "-3β-N/$^2$-"  --- -3β-/$N^2$- ---

Col. 27, line 20 - "prednisolone-b-21-"  --- prednisolone-21- ---

Col. 27, line 32 - "-21N-(2-"  --- -21-N-(2- ---

Col. 30, line 14 - "17β"  --- 17α ---

Col. 30, line 43 - "IIβ-"  --- 11β- ---

Col. 31, line 15 - "3β-$N^2$"  --- 3β-/$N^2$ ---

UNITED STATES PATENT OFFICE
CERTIFICATE OF CORRECTION

Patent No. 3,963,707             Dated September 1, 1976

Inventor(s)  Knut Bertil Högberg, et al.

It is certified that error appears in the above-identified patent and that said Letters Patent are hereby corrected as shown below:

Col. 36, line 11 - "17β-diacetate-3-diacetate-3-"   --- 17β-diacetate-3- ---

Cols. 39/40 (IN TABLE) (Line 26) - UNDER RESULTS - "carbamate"   --- carbamate/ ---

Col. 43, line 3 - "-16β-"   --- -17β- ---

Col. 46, line 21 - "$N/N^2$-"   --- $3β-/N^2$- ---

Col. 48, line 7 - " formula ti"   --- formula ---

Col. 51, line 39 - "17β-ethynyl-18-"   --- 17α-ethynyl-18- ---

Col. 60, line 3 - "endrostan"   --- androstan ---

Col. 62, line 35 - "$-21-N^2$,"   --- $-21-/N^2$ ---

Col. 62, line 39 - "$3β-N^2$-"   --- $3β-/N^2$- ---

Signed and Sealed this

Sixteenth Day of November 1976

[SEAL]

Attest:

RUTH C. MASON
Attesting Officer

C. MARSHALL DANN
Commissioner of Patents and Trademarks